US010080517B2

United States Patent
Chen et al.

(10) Patent No.: US 10,080,517 B2
(45) Date of Patent: Sep. 25, 2018

(54) METHODS AND STRUCTURES FOR ASSEMBLING LANCET HOUSING ASSEMBLIES FOR HANDHELD MEDICAL DIAGNOSTIC DEVICES

(71) Applicant: Roche Diagnostics Operations, Inc., Indianapolis, IN (US)

(72) Inventors: Guangqun Max Chen, San Francisco, CA (US); Chris Fruhauf, San Anselmo, CA (US); Steven N Roe, San Mateo, CA (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 990 days.

(21) Appl. No.: 14/515,659

(22) Filed: Oct. 16, 2014

(65) Prior Publication Data

US 2015/0039007 A1 Feb. 5, 2015
US 2017/0360343 A9 Dec. 21, 2017

Related U.S. Application Data

(63) Continuation of application No. PCT/EP2013/001101, filed on Apr. 15, 2013.
(Continued)

(51) Int. Cl.
*A61B 5/15* (2006.01)
*A61B 5/151* (2006.01)
(Continued)

(52) U.S. Cl.
CPC ...... *A61B 5/150374* (2013.01); *A61B 5/1411* (2013.01); *A61B 5/14532* (2013.01); *A61B 5/157* (2013.01); *A61B 5/150022* (2013.01); *A61B 5/15113* (2013.01); *A61B 5/15117* (2013.01); *A61B 5/15151* (2013.01); *A61B 5/15161* (2013.01); *A61B 5/150175* (2013.01); (Continued)

(58) Field of Classification Search
CPC ............ A61B 5/1411; A61B 5/150022; A61B 5/150282; A61B 5/150297; A61B 5/150412–5/150465; A61B 5/15149–5/15155; A61B 5/15159; A61B 5/15161
See application file for complete search history.

(56) References Cited

U.S. PATENT DOCUMENTS

| 2009/0099477 A1* | 4/2009 | Hoenes | A61B 5/15146 600/583 |
| 2010/0010375 A1* | 1/2010 | Haar | A61B 5/14532 600/583 |

(Continued)

FOREIGN PATENT DOCUMENTS

| EP | 2226007 A1 | 9/2010 |
| EP | 2384699 A1 | 11/2011 |
| WO | 2011006913 A1 | 1/2011 |

*Primary Examiner* — Adam J Eiseman

(57) ABSTRACT

A method of assembling a lancet housing assembly comprising multiple lancets for use in a portable handheld medical diagnostic device for sampling bodily fluids from a skin site of a patient is disclosed. The method includes forming a plurality of lancet structures in a lancet sheet. The lancet sheet has a removable ledge for releasing the lancet structures. The removable ledge of the lancet sheet is flexed for releasing the lancet structures from the removable ledge.

10 Claims, 44 Drawing Sheets

Related U.S. Application Data

(60) Provisional application No. 61/624,591, filed on Apr. 16, 2012, provisional application No. 61/624,594, filed on Apr. 16, 2012, provisional application No. 61/624,599, filed on Apr. 16, 2012, provisional application No. 61/624,601, filed on Apr. 16, 2012, provisional application No. 61/624,603, filed on Apr. 16, 2012, provisional application No. 61/624,625, filed on Apr. 16, 2012, provisional application No. 61/624,628, filed on Apr. 16, 2012, provisional application No. 61/624,631, filed on Apr. 16, 2012, provisional application No. 61/624,565, filed on Apr. 16, 2012, provisional application No. 61/624,558, filed on Apr. 16, 2012, provisional application No. 61/624,632, filed on Apr. 16, 2012.

(51) Int. Cl.
*A61B 5/145* (2006.01)
*A61B 5/157* (2006.01)

(52) U.S. Cl.
CPC ...... *A61B 5/15176* (2013.01); *A61B 5/15178* (2013.01); *A61B 5/150282* (2013.01); *A61B 5/150358* (2013.01); *A61B 5/150419* (2013.01); *A61B 5/150435* (2013.01); *A61B 5/150503* (2013.01); *Y10T 29/49826* (2015.01)

(56) References Cited

U.S. PATENT DOCUMENTS

| 2010/0234869 A1* | 9/2010 | Sacherer ............ A61B 5/15146 606/182 |
| 2011/0230905 A1 | 9/2011 | Roe et al. |
| 2012/0039772 A1* | 2/2012 | Hoenes .................. A61B 5/15 422/535 |
| 2012/0063970 A1 | 3/2012 | List et al. |

* cited by examiner

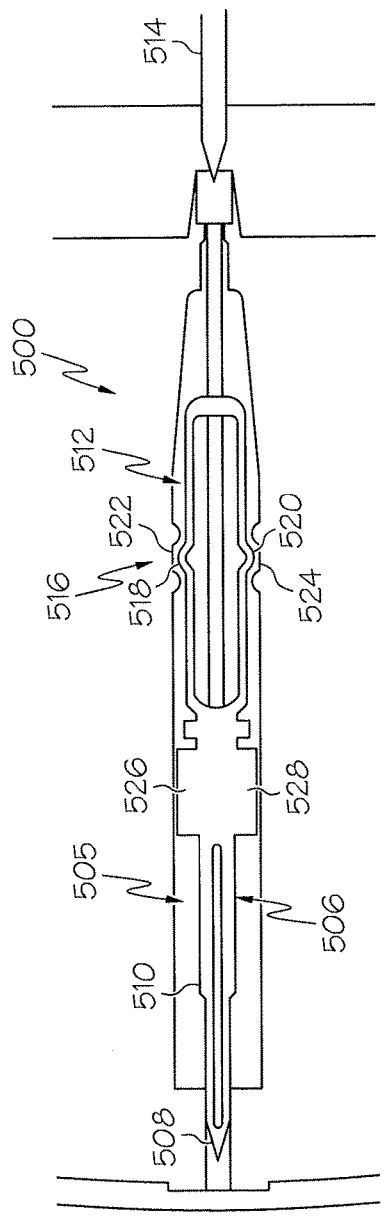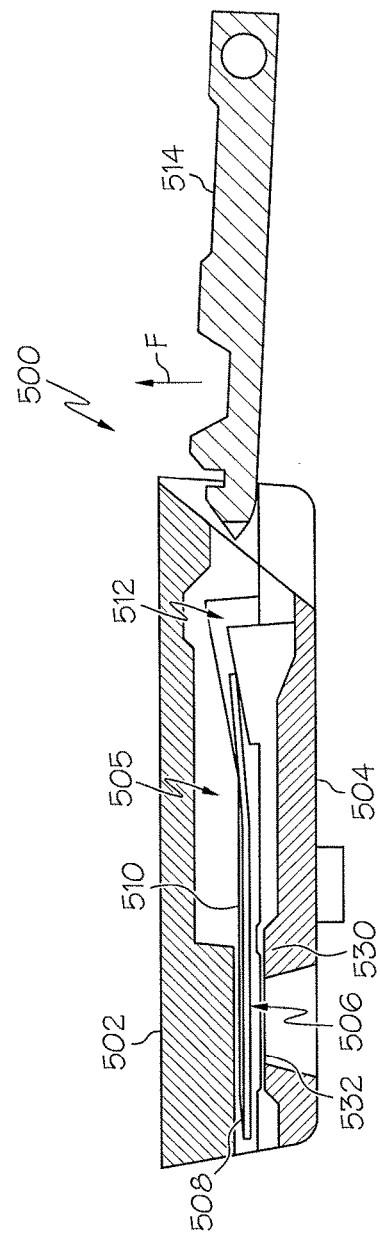

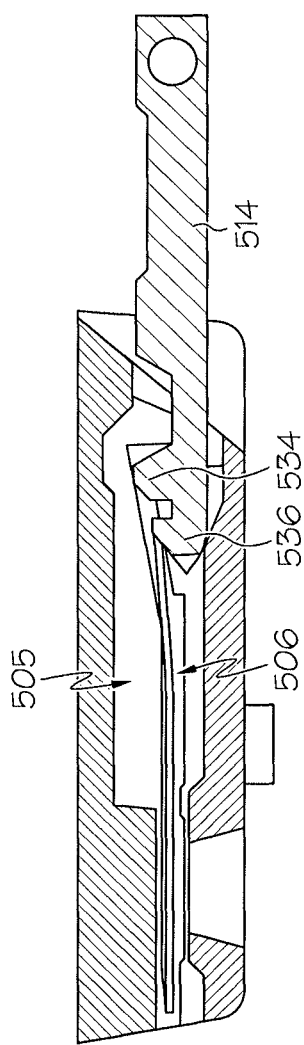
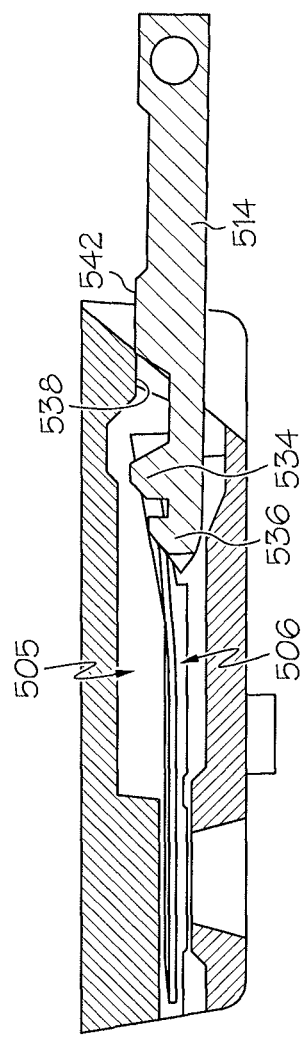

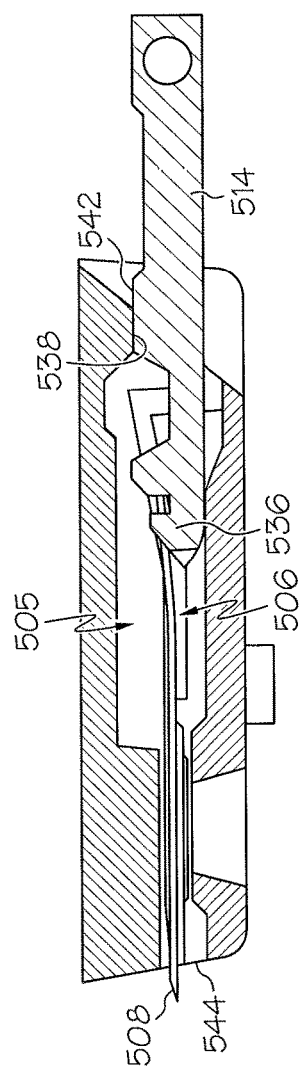
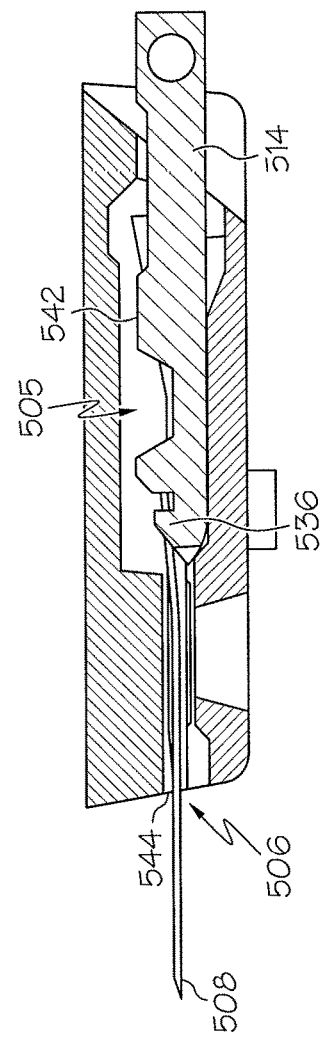

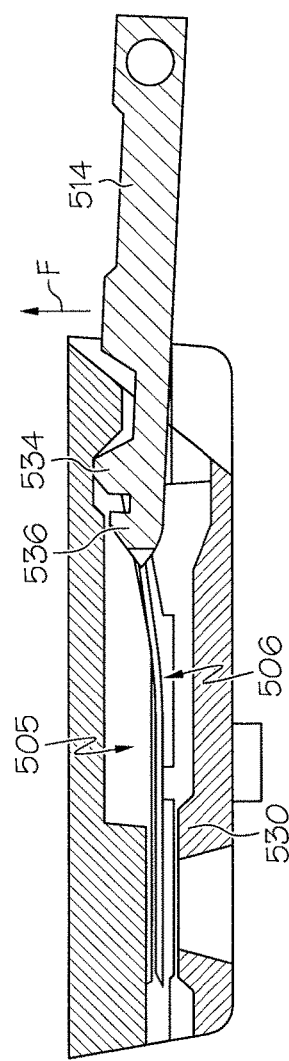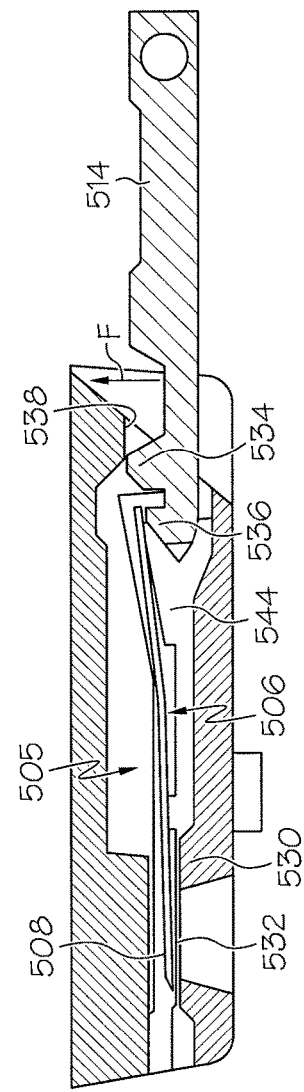

METHODS AND STRUCTURES FOR ASSEMBLING LANCET HOUSING ASSEMBLIES FOR HANDHELD MEDICAL DIAGNOSTIC DEVICES

CROSS-REFERENCE TO RELATED APPLICATIONS

This application is a continuation of PCT Application No. PCT/EP2013/001101, filed Apr. 15, 2013, and claims the benefit of priority to U.S. Provisional Application Ser. Nos. 61/624,632, 61/624,631, 61/624,628, 61/624,625, 61/624,603, 61/624,601, 61/624,599, 61/624,594, 61/624,591, 61/624,558 and 61/624,565, all filed Apr. 16, 2012, and the details of all of the foregoing applications are incorporated herein by reference as if fully set forth herein.

TECHNICAL FIELD

The present disclosure relates generally to lancet housing assemblies for handheld medical devices, and in particular, to a lancet housing assembly for a handheld medical diagnostic device that can reduce steps needed to measure concentrations of biologically significant components of bodily fluids.

BACKGROUND

Portable handheld medical diagnostic devices are often employed to measure concentrations of biologically significant components of bodily fluids, such as, for example, glucose concentration in blood. The portable handheld medical diagnostic devices and their accessories may work together to measure the amount of glucose in blood and be used to monitor blood glucose in one's home, healthcare facility or other location, for example, by persons having diabetes or by a healthcare professional.

For people with diabetes, regular testing of blood glucose level can be an important part of diabetes management. Thus, it is desirable to provide medical diagnostic devices that are portable and easy to use. Various medical diagnostic devices have been introduced for testing blood sugar that are portable. However, there continues to be a need for improved portability and ease of use for medical diagnostic devices.

Often times, self-monitoring of blood glucose may require the patient to first load a lancet into a lancer and a separate test strip into a blood glucose meter. The lancer and lancet are then used to prick the finger and a small drop of blood is squeezed to the surface. The sample port on the strip is brought into contact with the blood and the sample may be transported to the reaction zone on the strip via capillary action. This can be a labor-intensive, uncomfortable process that requires multiple steps and devices. Patients may need to repeat this process several times a day.

SUMMARY

In one embodiment, a method of assembling a lancet housing assembly comprising multiple lancets for use in a portable handheld medical diagnostic device for sampling bodily fluids from a skin site of a patient is provided. The method includes forming a plurality of the lancet structures in a lancet sheet. The lancet sheet has a removable ledge for releasing the lancet structures. The removable ledge of the lancet sheet is flexed for releasing the lancet structures from the removable ledge.

In another embodiment, a lancet sheet provides multiple lancets for a lancet housing assembly for use in a portable handheld medical diagnostic device for sampling bodily fluids from a skin site of a patient. The lancet sheet includes a removable ledge formed of material forming the lancet sheet. A plurality of lancet structures is formed of material forming the lancet sheet. The plurality of lancet structures comprises a skin penetrating end and a blood transport portion adjacent the skin penetrating end. The skin penetrating end is shaped and sized to penetrate the patient's skin at the skin site to provide an amount of blood. A plurality of spring components is formed of material that forms the lancet sheet that releasably connect the plurality of lancet structures to the removable ledge.

In another embodiment, a lancet housing pre-assembly for forming a lancet housing assembly including multiple lancet structures for use in a portable handheld medical diagnostic device for sampling bodily fluids from a skin site of a patient is provided. The lancet housing pre-assembly includes an upper disk member and a lower disk member that connects to the upper disk member for forming a plurality of lancet compartments therebetween for housing a plurality of lancet structures. A lancet sheet provides the plurality of lancets for the lancet housing assembly. The lancet sheet includes a removable ledge formed of material forming the lancet sheet. A plurality of lancet structures is formed of material forming the lancet sheet. The plurality of lancet structures comprise a skin penetrating end and a blood transport portion adjacent the skin penetrating end. The skin penetrating end is shaped and sized to penetrate the patient's skin at the skin site to provide an amount of blood. A plurality of spring components is formed of material that forms the lancet sheet that releasably connects the plurality of lancet structures to the removable ledge.

These and other advantages and features of the various embodiments of the invention disclosed herein, will be made more apparent from the description, drawings and claims that follow.

BRIEF DESCRIPTION OF THE DRAWINGS

The following detailed description of the exemplary embodiments of the present invention can be best understood when read in conjunction with the following drawings, where like structure is indicated with like reference numerals, and in which:

FIG. 30 illustrates another embodiment of lancet housing assembly;

FIG. 31 illustrates the lancet housing assembly of FIG. 30 in operation;

FIG. 34 illustrates the lancet housing assembly of FIG. 30 in operation;

FIG. 35 illustrates the lancet housing assembly of FIG. 30 in operation;

FIG. 36 illustrates the lancet housing assembly of FIG. 30 in operation;

FIG. 37 illustrates the lancet housing assembly of FIG. 30 in operation;

FIG. 38 illustrates the lancet housing assembly of FIG. 30 in operation;

FIG. 39 illustrates the lancet housing assembly of FIG. 30 in operation;

DETAILED DESCRIPTION

The following description of the preferred embodiment is merely exemplary in nature and is in no way intended to limit the invention or its application or uses.

Embodiments described herein generally relate to handheld medical diagnostic devices that are used to acquire and measure concentrations of biologically significant components of bodily fluids. In particular, the handheld medical diagnostic device may be used to acquire a blood sample and measure a blood glucose level of the sample. As will be described below, the medical diagnostic device may include a lancet housing assembly with multiple lancet structures inside the medical diagnostic device, which can be used to generate a prick wound in a body part. The lancet structures can also be used to take up blood emerging from the prick wound using capillary action and deliver the blood to a reagent material. A measuring system located in the medical diagnostic device may be used to determine a blood glucose concentration value of the acquired blood.

Figure 1:
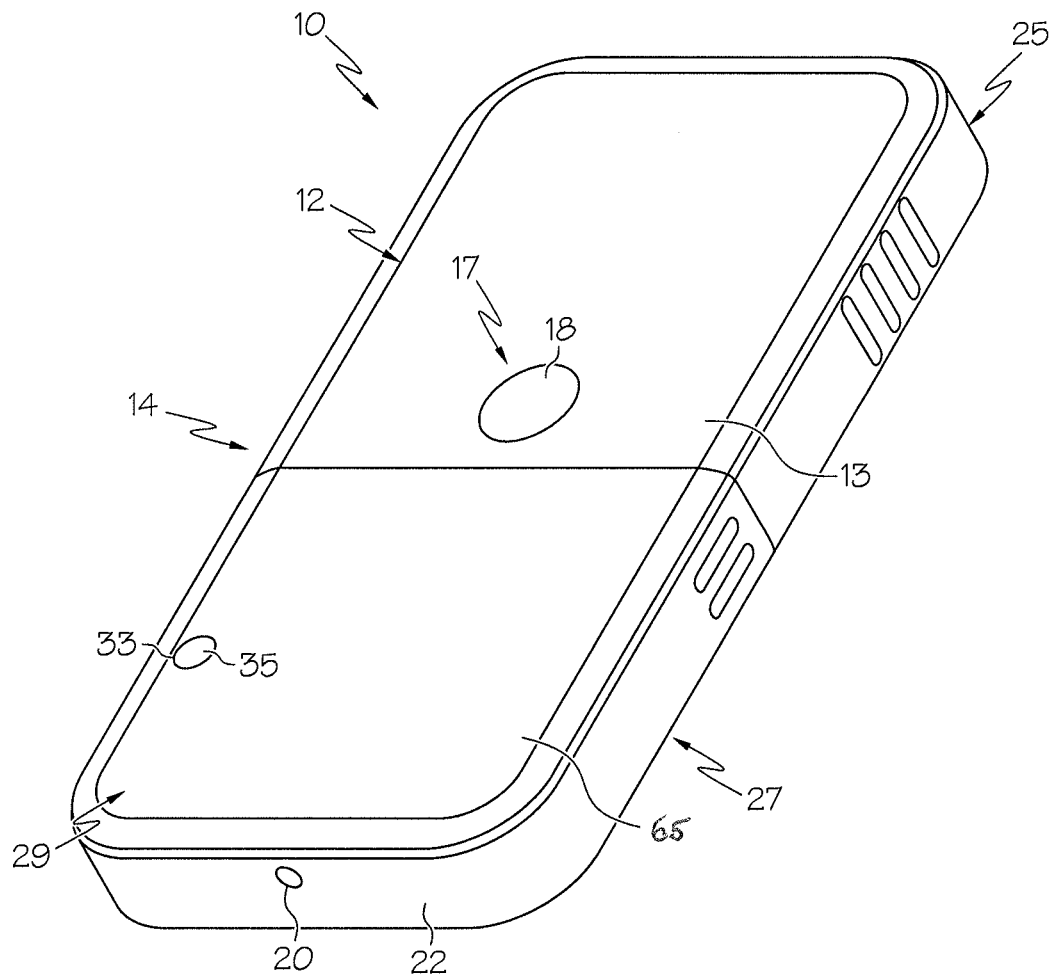
FIG. 1 is a perspective view of an embodiment of a portable handheld medical diagnostic device.

Referring to FIG. 1, a portable, handheld medical diagnostic device 10 with a display device 12 behind a transparent, protective lens 13 includes a protective enclosure, generally indicated by element 14 that protects electronics and other mechanical components therein. The protective enclosure 14 is somewhat rectangular in shape, however, any other suitable shapes may be used for the protective enclosure, such as circular shapes, etc. The display device 12 may be any suitable display device used in a portable, handheld electronic device, such as, for example, but not limited to LCD display devices, LED display devices, OLED display devices, and other types of display devices which may be heretofore developed. Further, display device 12 may be any other variety of indicators, including, but not limited to a series of lights and/or other types of light devices as opposed to a single integrated display screen. In the illustrated embodiment, the display device 12 includes an electronic paper component such as an electrophoretic display, which may be an information display that forms visible images by rearranging charged pigment particles using an electric field. The display device 12 may be used for electronically displaying graphics, text, and other elements to a user. In some embodiments, the display device 12 may be a touch-screen user interface that is used with the tip of a finger of the user and/or a stylus or other touching device to select elements from the screen, to draw figures, and to enter text with a character recognition program running on the device 10. In some embodiments, the medical diagnostic device 10 may also include other types of output devices such as for example, sound devices, vibration devices, etc.

The medical diagnostic device 10 further includes a user interface (generally referred to as element 17), which may include a button 18. More than one button may also be used. The button 18 may be used by an operator, for example, to view memory of the medical diagnostic device 10, adjust settings of the device and scroll through test results. The button 18 may be manually actuated, such as by pressing the button 18. The button 18 may include touch sensors (e.g., resistive or capacitive touch sensors, surface acoustic wave sensors, infrared LED, photodetectors, piezoelectric transducers, etc.) that can be actuated by placing and/or pressing a tip of the finger on the button area. In these embodiments, the button 18 may not move. Instead, the button 18 may be indicated visually to identify where to place the finger. In other embodiments utilizing touch sensors, the button 18 may move, for example, to bring the finger or touching device into close proximity to the touch sensor. In some embodiments, the medical diagnostic device 10 may provide other button or input types such as an OK button and/or joy stick/track ball, which a user may utilize to navigate through a software drive menu provided on the display device 12. Additional buttons may be used as shortcut buttons, for example, to call up a certain program on the medical diagnostic device 10, as a method of scrolling, to select items from a list, or to provide any function that the software designer of the device may assign to the button or set of buttons. Each button size, layout, location, and function may vary for each manufacturer and model of the medical diagnostic device 10.

A lancet port 20 is located at a bottom 22 of the medical diagnostic device 10. The lancet port 20 provides an opening through which the lancet structure can extend outwardly from the protective enclosure 14. The lancet structure may extend outwardly from the lancet port 20 to make an incision at a skin site of the patient and produce an amount of bodily fluid from the skin site of the patient. In one embodiment, the medical diagnostic device 10 is an in vitro diagnostic device that is used to test blood and other body fluids and tissues to obtain information for the diagnosis, prevention and treatment of a disease. The medical diagnostic device 10 may be a self-testing blood glucose meter for people with diabetes. In one embodiment, the medical diagnostic device 10 is a handheld reagent-based blood glucose meter, which measures glucose concentration by observing some aspect of a chemical reaction between a reagent and the glucose in a fluid sample. The reagent may be a chemical compound that is known to react with glucose in a predictable manner, enabling the monitor to determine the concentration of glucose in the sample. For example, the medical diagnostic device 10 may be configured to measure a voltage or a current generated by the reaction between the glucose and the reagent in one embodiment, electrical resistance in another embodiment, as well as a color change of the reagent in still another embodiment.

In some embodiments, the medical diagnostic device 10 is a mechanically-driven device where the protective enclosure 14 includes a winding assembly (not shown) that is operated using telescoping housing portions 25 and 27. FIG. 1 illustrates the telescoping housing portions 25 and 27 in their initial, uncocked positions. As will be described in greater detail below, the housing portions 25 and 27 may be moved relative to each other manually to place a lancet actuator assembly (not shown) in a wound, triggerable configuration. The lancet actuator assembly may be used to drive a lancet structure through the lancet port 20 to make an incision at a skin site of the patient and produce an amount of bodily fluid that can then be carried from the skin site of the patient. In some embodiments, the housing portion 27 includes a cartridge housing 29 with a removable door 65 for holding a lancet housing assembly (not shown) that includes multiple lancet structures. In other embodiments, the door 65 may be hinged to the housing portion 27, such that it can be rotated relative to the housing portion 27 to permit access to the cartridge housing 29 for removing or loading the lancet housing assembly. An indicator device 33 may be provided that provides the patient with information regarding the number of unused lancet structures available in the lancet housing assembly. In this embodiment, the indicator device 33 includes a window 35 in the removable door 65 that allows viewing of numbers provided on the lancet housing assembly as the lancet housing assembly is indexed within the cartridge housing 29.

Figure 2:
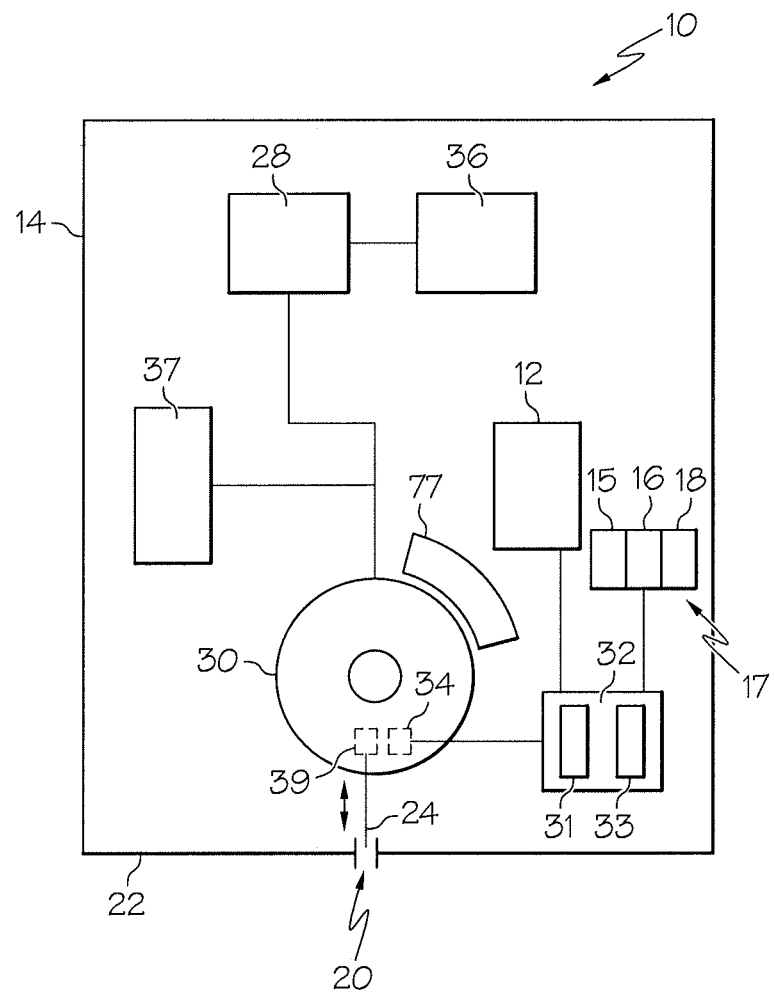
FIG. 2 is a schematic representation of the portable handheld medical diagnostic device of FIG. 1.

Referring to FIG. 2, a simplified, schematic view of the medical diagnostic device 10 includes a number of features that allow for improved comfort and ease of use for a patient. In general, the medical diagnostic device 10 may include a lancet housing assembly 30 in the form of a cartridge or disk that is used to house multiple lancet structures 24 for use in the medical diagnostic device 10, a lancet actuator assembly 28 for extending and/or retracting the lancet structures 24 and a speed control mechanism 36 that engages the lancet actuator assembly 28 for adjusting the speed at which the lancet structure 24 is extended and/or retracted by the lancet actuator assembly 28. A depth adjustment mechanism 37 may also be provided that allows for adjustment of a penetration depth of the lancet structure 24 before extending the lancet structure 24. A disk indexing system 77 may be provided for indexing or rotating the lancet housing assembly 30 from one used lancet structure to another unused lancet structure.

A measurement system 32 may be provided that measures glucose concentration in a blood sample delivered to a test material 39, for example, using an optical device 34 in one embodiment for detecting a color change in a reagent or other suitable device in other embodiments, such as electrical contacts if measuring a change in an electrical characteristic/property of the reagent. The test material 39 may be employed to hold the reagent and to host the reaction between the glucose and the reagent mentioned above. In one embodiment, the test material 39 and the optical device 34 may be located such that the reaction between the glucose and the reagent may be read electronically in order for the measurement system 32 to determine the concentration of glucose in the sample and display the results to a user using the display device 12. These embodiments enable both health care professionals and patients to perform reliable decentralized testing in hospitals, clinics, offices or patients' homes.

In one embodiment, after the test material 39 is provided with the blood sample, the test material 39 is illuminated by the measurement system 32 such that any color change due to the chemical reaction between the sample and the reagent of the test material 39 is detected by the optical device 34, e.g., a photo-diode detector. A resulting detection signal from the optical device 34 is then provided to and processed by the processor 31 of the measurement system 32. The result(s) of the processing by the processor 31 on the received detection signal to determine a characteristic(s) and/or a property(ies) of the provided blood sample may be displayed on the display device 12 and/or stored in memory 33 of the device 10 (or measurement system 32) or maintained by the display device 12 until updated by a next measurement result, as is the case if the display device 12 is an electronic paper based display. In one embodiment, the user interface 17 may be used by the user to select and display testing results stored in memory 33 as well as to communicate with the processor 31 to perform any of the device functions discussed previously above in earlier sections. It is to be appreciated that in other embodiments, the processor 31 and memory 33 as well as the measurement system 32 along with other system components (not shown) such as a display controller and/or display driver, a clock, an analog to digital convertor(s), light(s), power (battery) management controller/functions may be provided as an application specific integrated chip (ASIC), as individual (discrete) components in still other embodiments, or in combinations thereof in still other embodiments. Such components are electrically connected to the processor 31 and all of which are powered by a portable power supply (not shown), such as a battery which may or may not be rechargeable by an A/C adapter, such as in the embodiment of the device 10 being a limited use and disposable device. Other features of a suitable medical diagnostic device are described in co-pending and commonly owned U.S. patent application Ser. No. 12/981,677, filed Dec. 30, 2010, and entitled HANDHELD MEDICAL DIAGNOSTIC DEVICES, the disclosure of which is herein incorporated fully by reference.

Figure 3:
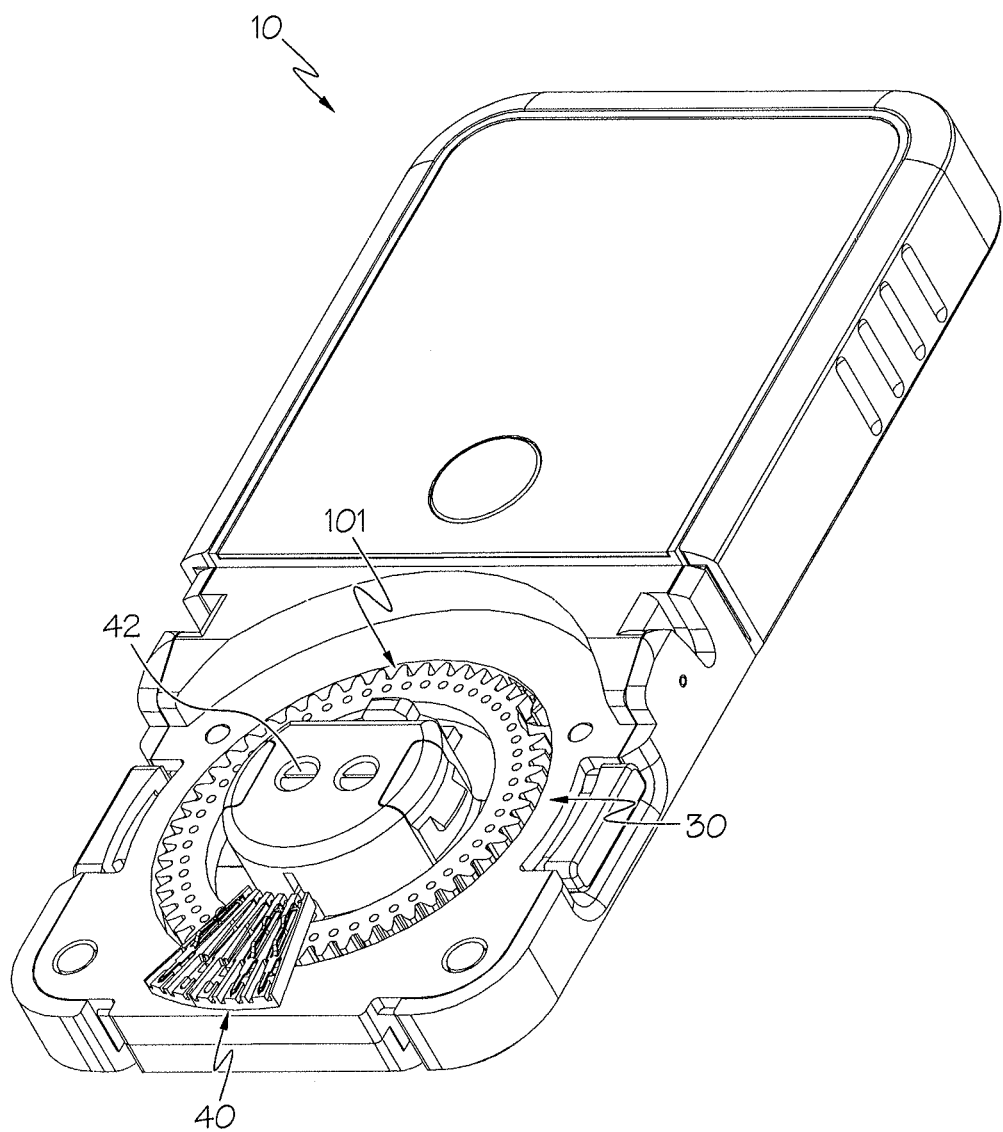
FIG. 3 is another perspective view of the portable handheld medical diagnostic device of FIG. 1 with an embodiment of a lancet housing assembly exposed.

Referring to FIG. 3, in some embodiments, multiple lancet structures are housed in the lancet housing assembly in the form of a disk 30 (only portions of disk 30 are shown in FIG. 3 for illustration) that includes multiple lancet compartments 40 arranged in a radial fashion about a central axis 42. The disk 30 may have an outer protective housing (not shown) formed of any one or more suitable materials, such as plastics, foils, metals, and the like. Materials with sterile moisture barriers may be used to provide lancet compartments 40 with protected environments.

Figure 4:
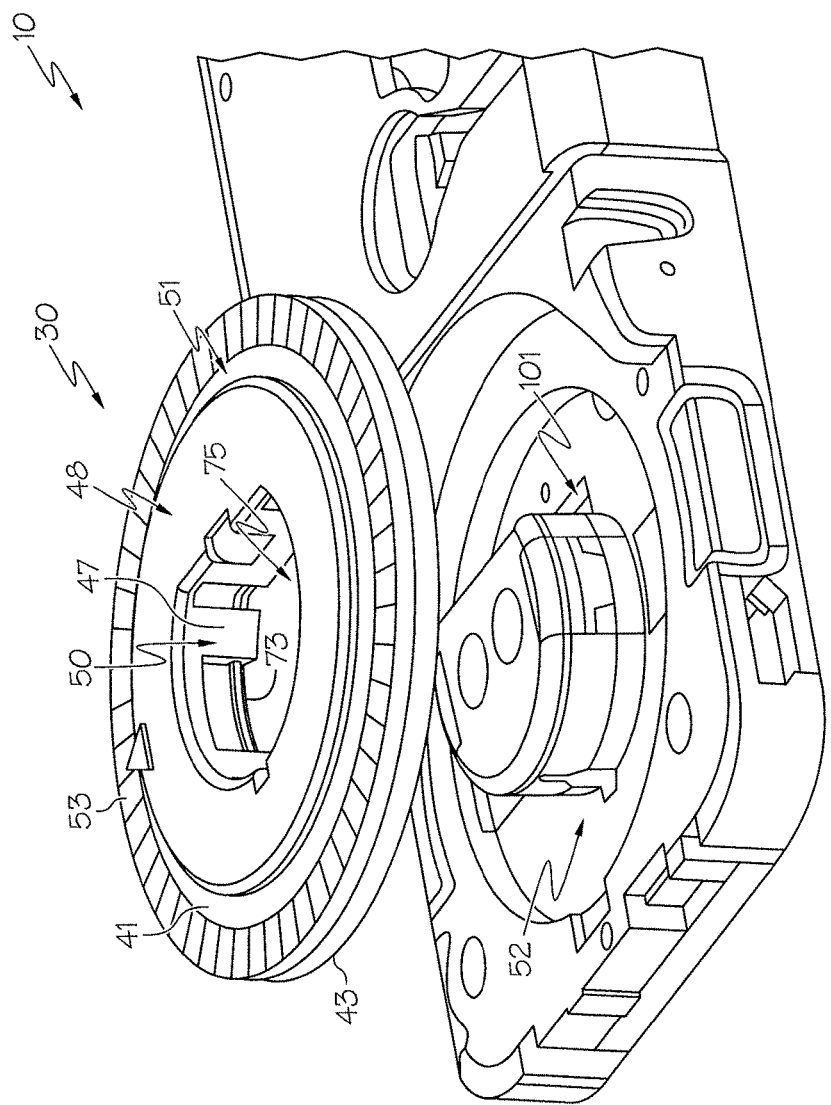
FIG. 4 is another perspective view of the portable handheld medical diagnostic device of FIG. 1 with an embodiment of a lancet housing assembly exposed.

Referring to FIG. 4, in some embodiments, the disk 30 may be formed by a center hub 48 and a disk component 51 that is configured to rotate relative to the center hub 48. In some embodiments, the disk component 51 includes an upper disk member 41 and a lower disk member 43 that is connected to the upper disk member 41. Any suitable connection may be used between the upper and lower disk members 41 and 43, such as laser welding, snap fit, press fit, adhesives, fasteners, and the like.

Figure 5:
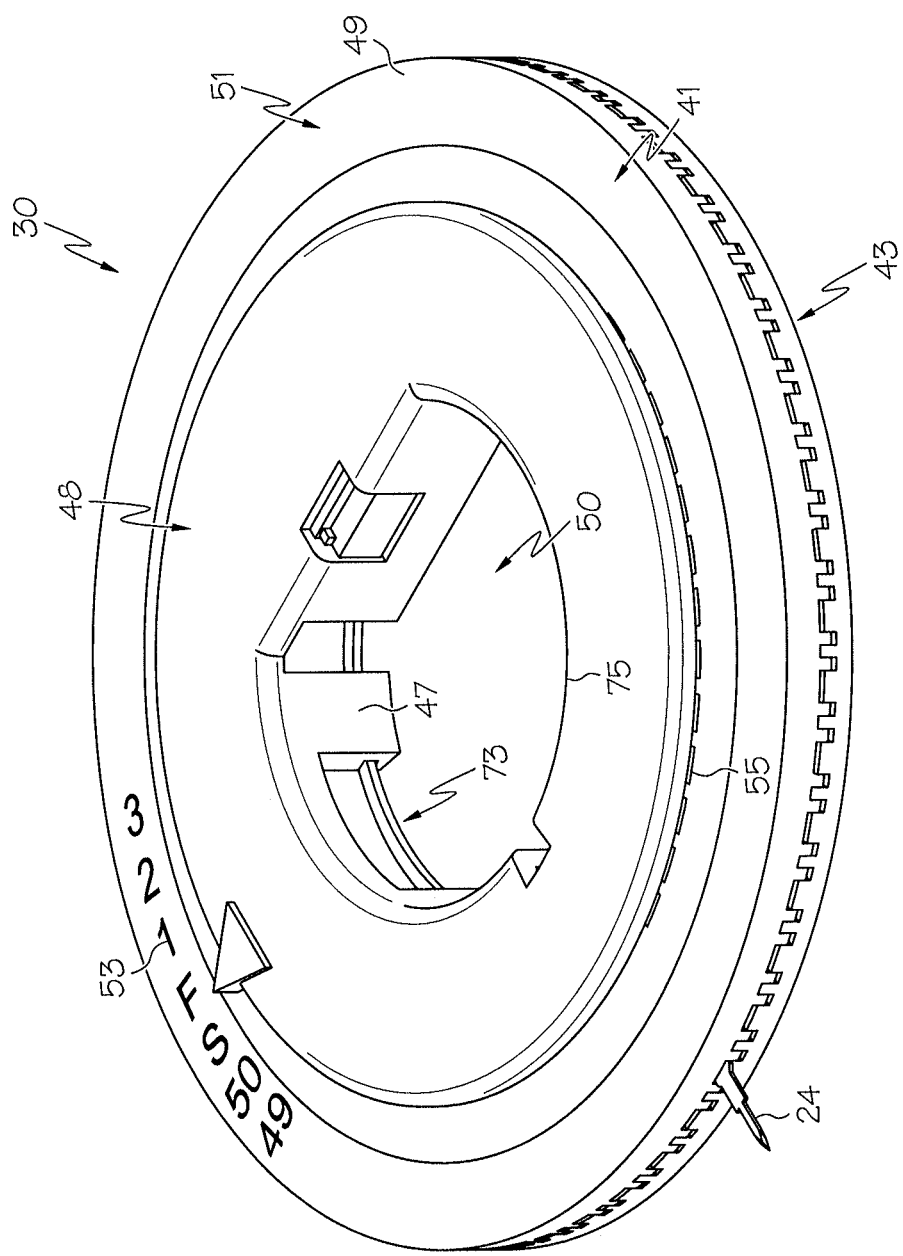
FIG. 5 is a perspective view of the lancet housing assembly of FIG. 4 in isolation.
Figure 6:
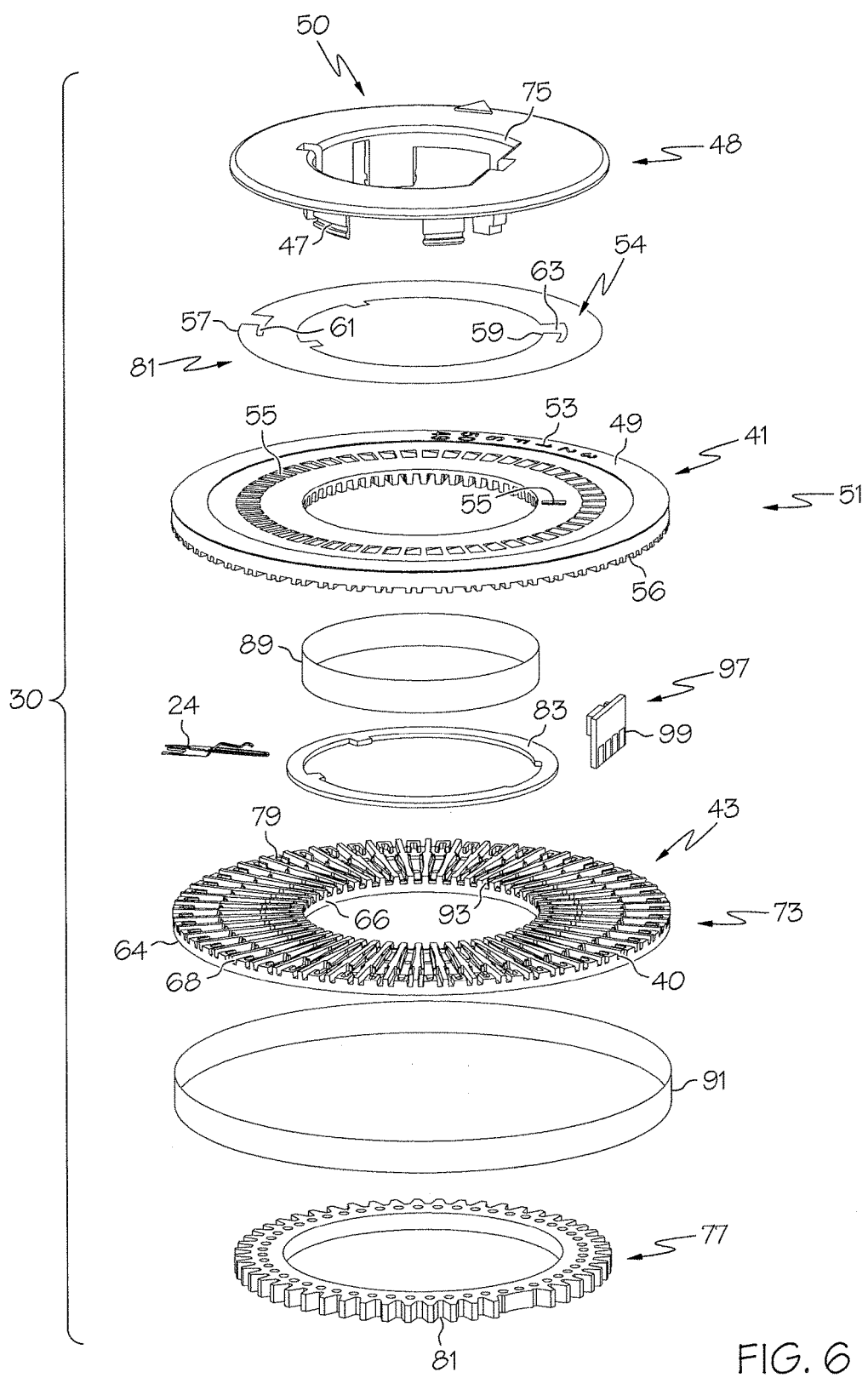
FIG. 6 is an exploded view of the lancet housing assembly of FIG. 5.

Referring also to FIGS. 5 and 6, the center hub 48 may be provided within a central bore 50 of the disk 30 such that it may rotate relative to the disk component 51. In one embodiment, the center hub 48 may be provided such that it may snap fit into place within the central bore 50 of the disk 30. For example, the center hub 48 may include fastening structures 47 in the form of hook-like projections that engage a bottom surface 73 of the disk component 51. Although the center hub 48 may be mounted rotatably within the central bore 50 of the disk 30 such that it may be removably retained therein, such as via the snap fit arrangement depicted in FIG. 5, or via a fastener(s) in another embodiment which provides a nut or clip (not shown) which engages a threaded or shaped end (not shown) of the center hub 48 adjacent the bottom surface 73, in other embodiments the center hub 48 may be provided rotatably therein but also retained permanently therein, such as via laser welding in another embodiment which provides a deformed free end (not shown) of the center hub 48 that flairs outwardly about the bottom surface 73. The center hub 48 may have a non-circular or irregular-shaped (e.g., D-shaped) key or opening 75 that allows for automatic alignment of the disk 30 in only one or more orientations for insertion into a disk compartment 52 of the medical diagnostic device 10. For example, in the illustrated embodiment, the D-shaped key may allow for automatic alignment of the disk 30 in only one orientation for insertion into the disk compartment 52.

The upper disk member 41 includes a top surface 49 and a bottom surface 56 opposite the top surface 49. Numbered indicia 53 (FIG. 4) may be printed, molded, etched, machined, etc. onto the top surface 49 for providing the user an indication of the number of unused lancet structures 24 are remaining or have been used. The numbered indicia 53 may be viewed through the window 35 of the removable door 65 (FIG. 1).

Referring particularly to FIG. 6, the top surface 49 of the upper disk member 41 may include a plurality of notches 55 that extend inwardly from the top surface 49 of the upper disk member 41. The notches 55 are spaced angularly from adjacent notches 55 and are located substantially equidistant from the center of the upper disk member 41. The notches 55 may each be associated with a respective lancet compartment 40 and provide engagement structure for preventing over rotation of the disk 30 relative to the center hub 48.

A spring component 81 located between the center hub 48 and the upper disk member 41 may include rotation limiting structure 54 that cooperates with rotation limiting structure (e.g., the notches 55) of the upper disk member 41. The spring component 81 may be an annular flat spring that also facilitates rotation of the disk component 51 relative to the center hub 48. The spring component 81 may include arm members 57 and 59, each having a downward protruding projection 61 and 63 that is sized and arranged to be removably received by the notches 55 as the disk component 51 rotates relative to the center hub 48. The projections 61 and 63 may each be formed by a bent portion of the arm members 57. The arm members 57 and 59 may be formed of spring steel of other somewhat resiliently flexible material to allow the arm members 57 and 59 to resiliently bend so that the projections 61 and 63 may move out of one notch 55 and be received by an adjacent notch 55 for locking the upper disk member 41 in an angular relationship relative to the center hub 48.

The lower disk member 43 includes a top surface 79, a bottom surface 73 opposite the top surface 79, an outer facing side 64 and an inner facing side 66. The lancet compartments 40 extend in a generally radial direction from the inner facing side 66 to the outer facing side 64. The lancet compartments 40 may be equally spaced an angular distance apart from one another and about the periphery of the lower disk member 43. As will be described in greater detail below, each lancet compartment 40 may include a lancet structure 24 that can extend through an opening 68 in each lancet compartment 40 and through the lancet port 20 of the medical diagnostic device 10. Extending downwardly from the bottom surface 73 of the lower disk member 43 is a disk indexing structure 77, which, in the illustrated embodiment, is in the form of a gear profile having teeth 81. The disk indexing structure 77 may be used to rotate the disk component 51 relative to the center hub 48, for example, after each operation of the lancet structures 24. A snap ring 83 may be used in connecting the upper disk member 41 and the lower disk member 43. Foil strips in the form of foil rings 89 and 91 may be used to cover inner and outer openings 68 and 93 leading into and out of individual lancet compartments 40.

Figure 7:
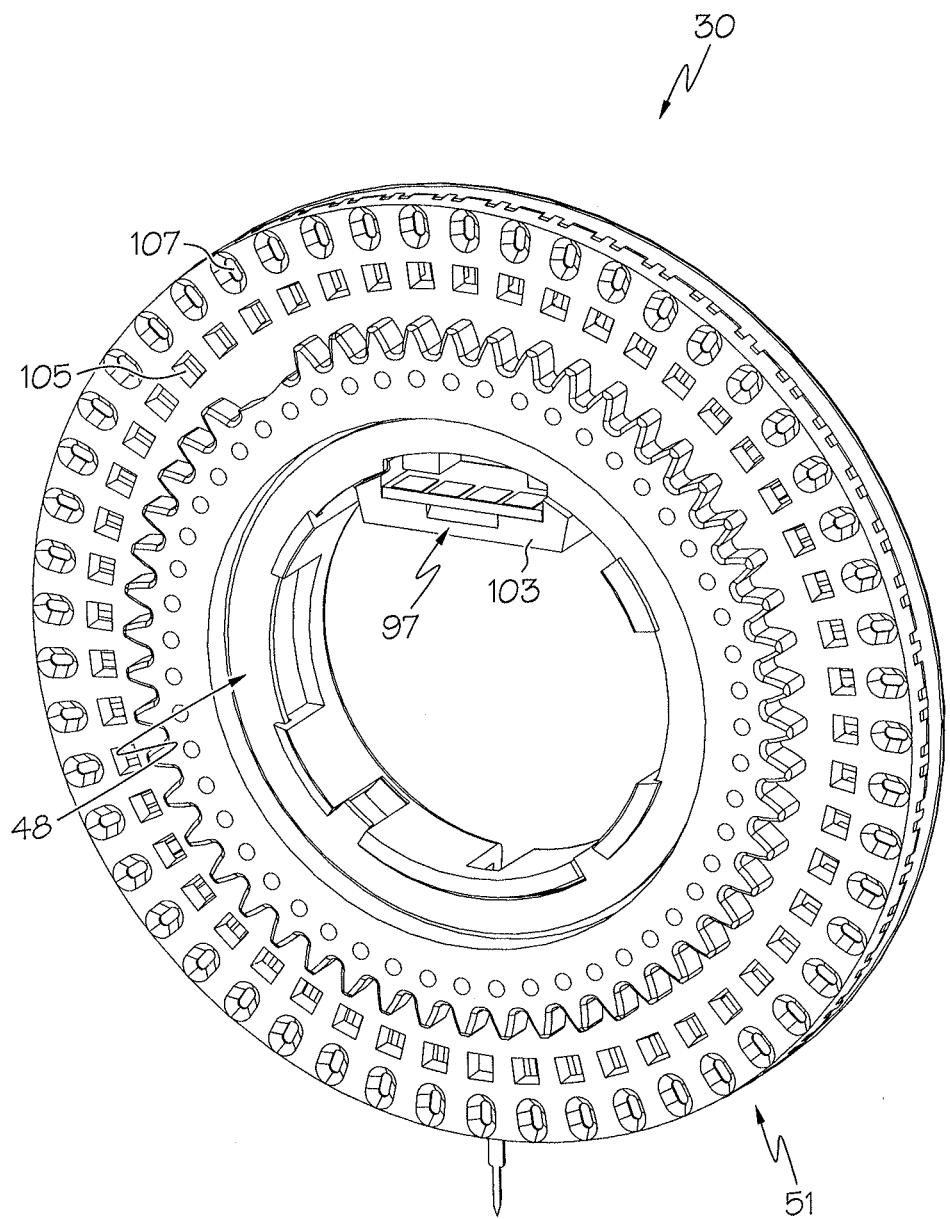
FIG. 7 is a perspective, bottom view of the lancet housing assembly of FIG. 5.

The disk 30 may also include a memory chip 97 having data stored in its memory. Such data may include chemistry data, expiration date and the like for the disk components housed in disk 30. The memory chip 97 may include contacts 99 that mate with contacts 101 located in the cartridge housing 29. Referring briefly to FIG. 7, the memory chip 97 may be snap fit into a chip-receiving hub 103 located on the center hub 48. The contacts 99 and 101 allow the data to be processed by the processor 31. In other embodiments, the disk 30 may include an optional RFID tag, and the medical diagnostic device 10 may include an RFID reader. In these embodiments, the medical diagnostic device 10 can download the data from the RFID tag. As can also be seen, the disk 30 further includes windows 105 that allows measurement system 32 (FIG. 2) access to the reagent material for making a measurement and alignment features 107 for use in controlling the indexing motion of the disk 30 to align the windows 105 with the measurement system 32.

Figure 8:
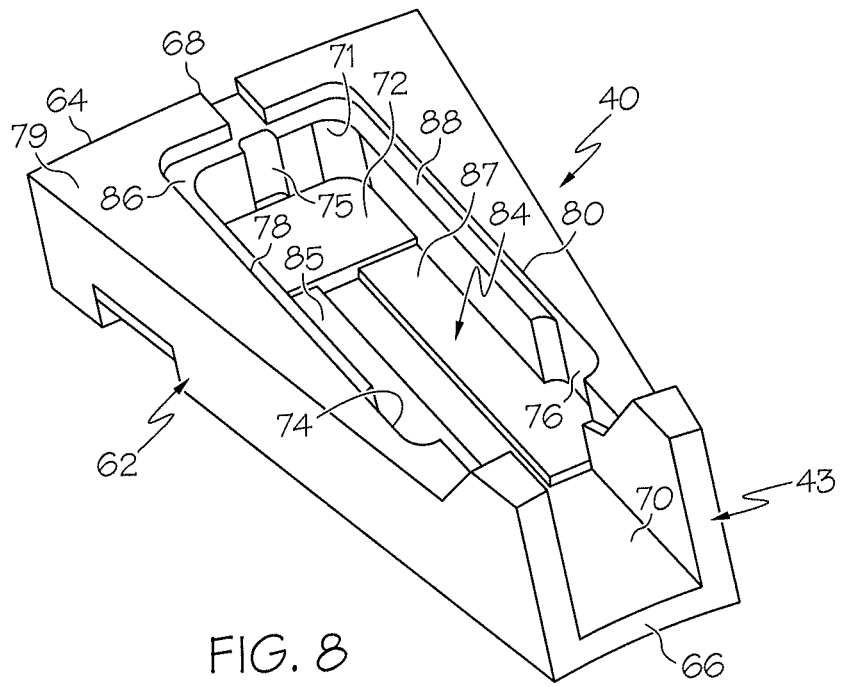
FIG. 8 is an embodiment of a lancet compartment for use with the lancet housing assembly of FIG. 5 without a lancet structure.
Figure 9:
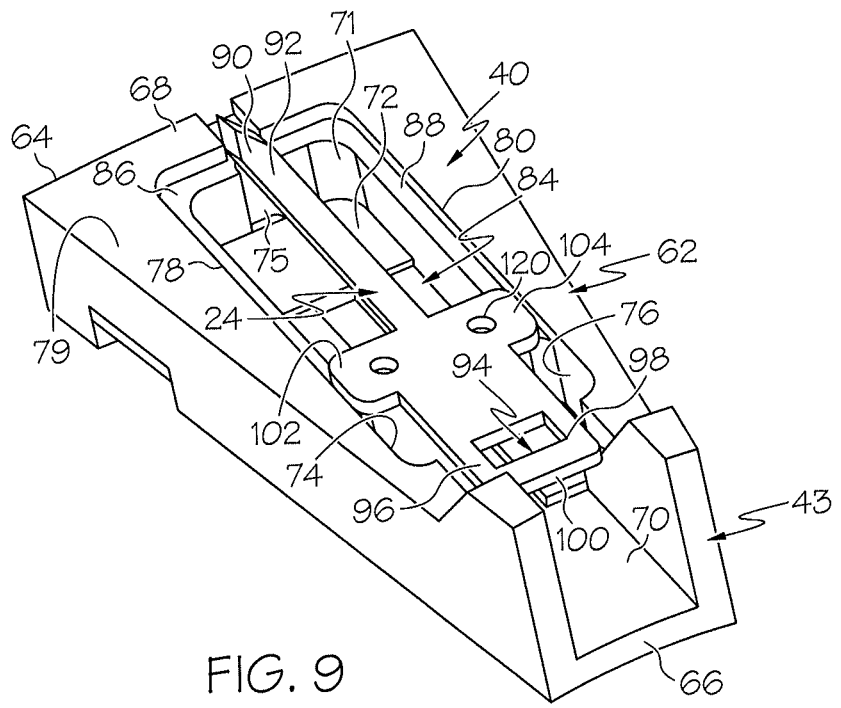
FIG. 9 illustrates the lancet compartment of FIG. 8 with an embodiment of a lancet structure.

Referring to FIGS. 8 and 9, an exemplary empty lancet compartment 40 and a lancet compartment 40 with an unused lancet structure 24 are shown, respectively. Referring first to FIG. 8, the lancet compartment 40 is formed, in part, by a compartment section 62 of the lower disk member 43. The upper disk member 41 is removed in FIGS. 8 and 9 for clarity. The compartment section 62 includes the outer facing side 64 and the inner facing side 66. The opening 68 is located at the outer facing side 64 that can align with the lancet port 20 located at the bottom 22 of the medical diagnostic device 10 (FIG. 1). Sidewalls 78 and 80 extend between the outer facing side 64 and the inner facing side 66. A clearance floor 70 extends from an inner wall 71 at the outer facing side 64 within the lancet compartment 40 to the inner facing side 66 and forms a lowermost floor of the lancet compartment 40. Adjacent the inner wall 71 of the lancet compartment 40 is a reagent material 72, which is located on the clearance floor 70 and within the lancet compartment 40. The reagent material 72 may be a test strip such as electrochemical type test strips, colorimetric or optical type test strips, etc. to name a few.

Drop down slots 74 and 76 are located in sidewalls 78 and 80 and extend vertically from the top surface 79 of the compartment section 62 to a lancet floor 84. Another drop down slot 75 is located in the inner wall 71 and extends vertically from the opening 68 to the reagent material 72. The lancet floor 84 extends along the clearance floor 70, in a raised relationship thereto, from the reagent material 72 back toward the inner facing side 66 and within the drop down slots 74 and 76. In some embodiments, the lancet floor 84 may be formed by a pair of strips 85 and 87 that extend along their respective sidewall 78 and 80 and spaced-apart from each other thereby exposing part of the clearance floor 70 therebetween. In some embodiments, the lancet floor 84 and the clearance floor 70 may both be part of the same floor structure. The lancet floor 84 provides clearance between the clearance floor 70 and the lancet structure 24 when the lancet structure is dropped down against the reagent material 72 and seated against the lancet floor 84. Lancet guide rails 86 and 88 extend along the sidewalls 78 and 80 and recessed vertically below the top surface 79 of the compartment section 62. In some embodiments, the lancet guide rails 86 and 88 extend substantially parallel to the lancet floor 84 and/or clearance floor 70 from the drop down slots 74 and 76 to the opening 68 with the drop down slot 75 intersecting the lancet guide rails 86 and 88 at the inner wall 71 and the drop down slots 74 and 76 intersecting the guide rails 86 and 88, respectively, at the sidewalls 78 and 80.

Referring to FIG. 9, the lancet compartment 40 is illustrated with a lancet structure 24. The lancet structure 24, in this exemplary embodiment, includes a skin penetrating end 90 and a blood transport portion 92 adjacent the skin penetrating end 90. In some embodiments, the blood transport portion 92 may include one or more capillary structures that facilitate movement of the bodily fluid away from the skin penetrating end to the blood transport portion 92. The skin penetrating end 90, when extended through the opening 68, is shaped and sized to penetrate the patient's skin at a skin location in order to provide an amount of blood. The blood transport portion 92 can receive the amount of blood from the skin penetrating end 90 and be used to carry the amount of blood away from the skin location.

A drive member connecting structure 94 is located at an end 96 that is opposite the skin penetrating end 90. In this embodiment, the drive member connecting structure 94 is a closed opening 98 having a rear ledge 100 that is used to engage the drive member 95 (e.g., in the form of a drive hook). Rail riding structure in the form of outwardly extending wings 102 and 104 are located between the drive connecting structure 94 and the blood transport portion 92. The wings 102 and 104 extend outwardly in the widthwise direction to ride along the lancet guide rails 86 and 88 when extending and retracting the lancet structure 24.

Figure 10:
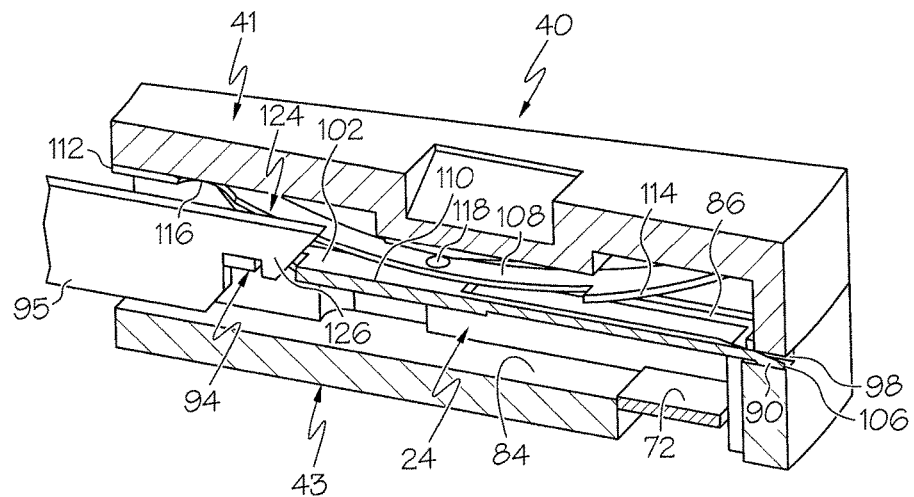
FIG. 10 illustrates the lancet compartment of FIG. 8 with the lancet structure in operation.

Referring to FIG. 10, a cross-section of the lancet compartment 40 is illustrated in an assembled configuration with the upper disk member 41 connected to the lower disk member 43 thereby providing the lancet compartment 40 therebetween. The drive member 95 extends into the lancet compartment 40 and is illustrated releasably engaged with the drive member connecting structure 94 of the lancet structure 24. The skin penetrating end 90 of the lancet structure 24 is illustrated as resting on a bottom surface 106 of the opening 68 while the wings (only wing 102 is partially shown) rest on the lancet guide rails (only guide rail 86 is partially shown).

A biasing mechanism 108 (e.g., a flat spring) extends into the lancet compartment 40, toward the lancet floor 84 and engages a surface 110 of the lancet structure 24. The biasing mechanism 108 may be connected at opposite ends 112 and 114 to a ceiling 116 of the upper disk member 41. A projection 118 formed in the biasing mechanism 108 may be provided that mates with a corresponding detent 120 of the lancet structure 24 (FIG. 9). In another embodiment, the lancet structure 24 may include the projection 118 and the biasing mechanism 108 may include the detent 120. Any other suitable mating arrangement can be used, such as opposing ramp structures. This mating arrangement can provide added resistance to unintended movement of the of the skin penetrating end 90 of the lancet structure 24 through the opening 68.

Figure 11:
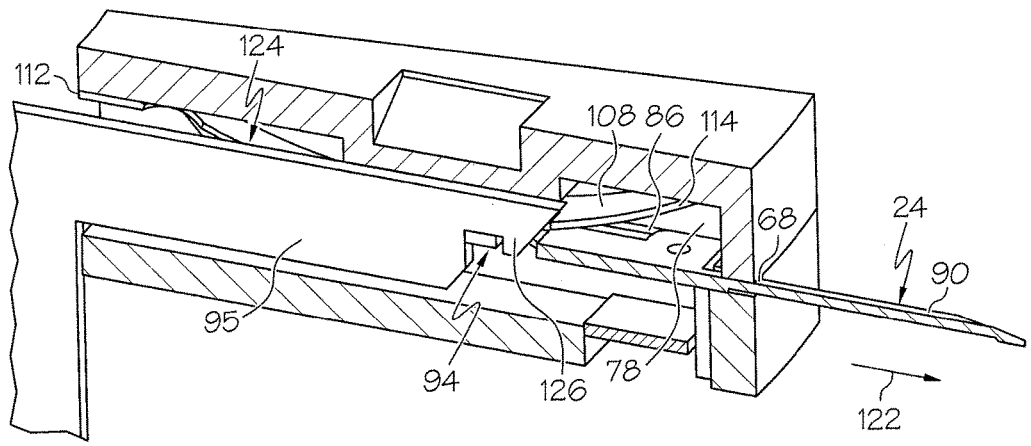
FIG. 11 illustrates the lancet compartment of FIG. 8 with the lancet structure in operation.

Referring to FIG. 11, the lancet structure 24 may be extended through the opening 68 in the direction of arrow 122 using the drive member 95 that is connected to the drive member connecting structure 94. As can be seen by FIGS. 10 and 11, the biasing mechanism 108 may include a slot 124 that is formed along a length of the biasing mechanism 108, between the ends 112 and 114. The slot 124 may be sized to receive a hook portion 126 of the drive member 95 and to allow movement of the drive member 95 through the slot 124 and toward the opening 68. In some embodiments, the hook portion 126 of the drive member 95 is received within the slot 124 such that the biasing mechanism 108 maintains contact with the lancet structure 24 as the lancet structure 24 is being driven toward the opening 68. As the lancet structure 24 is driven toward the opening 68, the outwardly extending wings 102 and 104 ride along the lancet guide rails 86 and 88 of the sidewalls 78 and 80.

Figure 12:
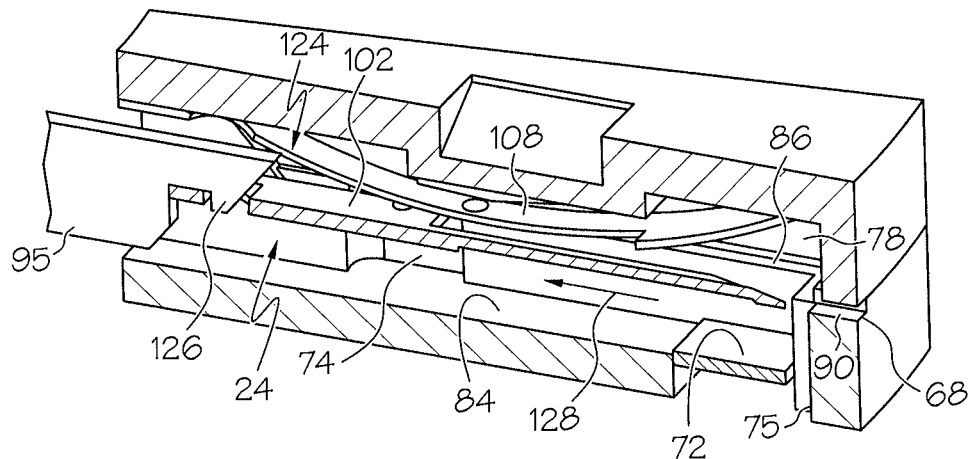
FIG. 12 illustrates the lancet compartment of FIG. 8 with the lancet structure in operation.

Referring to FIG. 12, the lancet structure 24 may be retracted from the opening 68 in the direction of arrow 128 using the drive member 95. The hook portion 126 of the drive member 95 may be received within the slot 124 such that the biasing mechanism 108 maintains contact with the lancet structure 24 as the lancet structure 24 is being driven away from the opening 68. As shown in FIG. 12, once the outwardly extending wings 102 and 104 that ride along the lancet guide rails 86 and 88 of the sidewalls 78 and 80 align with the drop down slots 74 and 76, and the skin penetrating end 90 aligns with or moves beyond the drop down slot 75, the biasing mechanism 108 forces the lancet structure 24 in a direction substantially transverse to the retract direction 128, toward the lancet floor 84 and the reagent material 72. Thus, the biasing mechanism 108 can be used to automatically deliver the lancet structure 24 to the reagent material 72 as the lancet structure 24 is retracted by the drive member 95.

Figure 13:
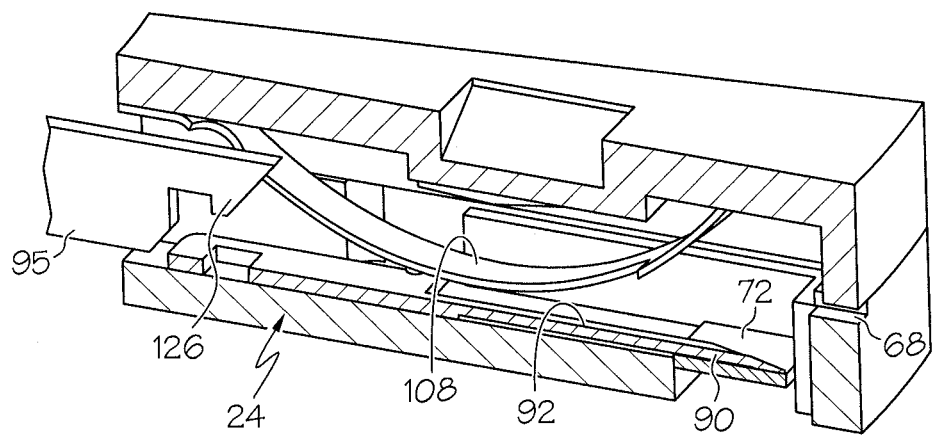
FIG. 13 illustrates the lancet compartment of FIG. 8 with the lancet structure in operation.

Referring to FIG. 13, the lancet structure 24 is illustrated fully retracted and directed toward the reagent material 72. In this position, the skin penetrating end 90 and the blood transport portion 92 of the lancet structure 24 are offset from the opening 68 (i.e., out of alignment with the opening 68) and in contact with the reagent material 72 such that blood can be transferred to the reagent material 72. In addition to delivering the lancet structure 24 to the reagent material 72, the offset arrangement of the skin penetrating end 90 out-of-alignment with the opening 68 can also inhibit unintended extension of the skin penetrating end 90 through the opening 68 by the drive member 95, which no longer can engage and extend the lancet structure 24. In particular, in the illustrated embodiment should the drive member 95 once again move towards the opening 68 of the lancet compartment 40 containing a used lancet structure 24, the drive member 95 will pass over the lancet structure 24 due to the offset arrangement also placing the drive member connecting structure 94 of the lancet structure 24 out-of-alignment with drive member 95. Accordingly, the biasing mechanism 108 providing the lancet structure 24 in the offset arrangement after the transfer of blood from the blood transport portion 92 of the lancet structure 24 to the reagent material 72, provides a convenient fail safe.

Figure 14:
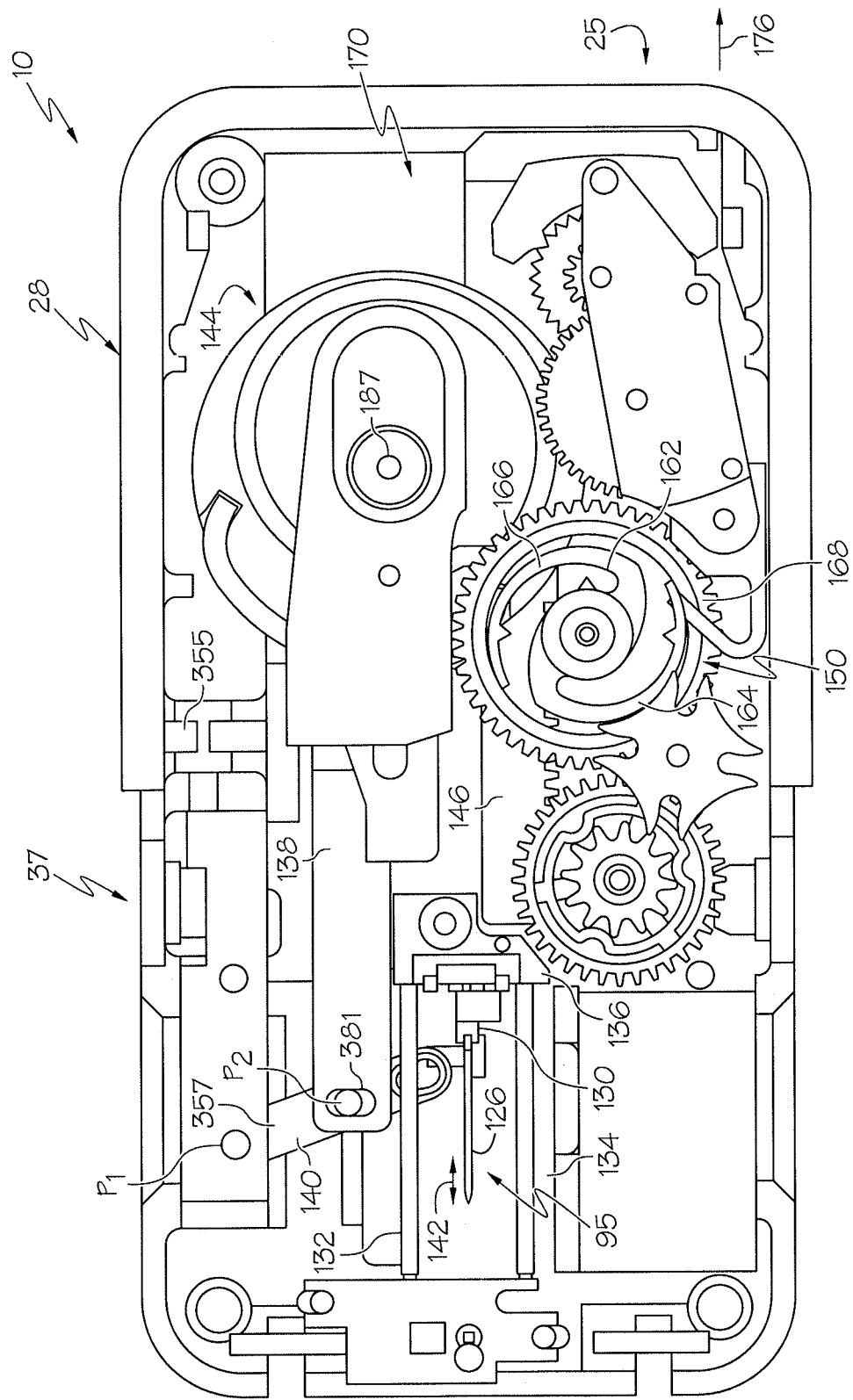
FIG. 14 illustrates the portable handheld medical diagnostic device of FIG. 1 with a portion of the housing removed.

Referring to FIG. 14, the drive member 95 including the hook portion 126 is operatively connected to the lancet actuator assembly 28, which is used to extend and retract the drive member 95. The drive member 95 is connected to a hook arm 130. The hook arm 130 can slide along a pair of guide rails 132 and 134, which are used to accurately guide the drive member 95 toward extended and retracted positions. The guide rails 132 and 134 are fixedly connected to the housing portion 27 by an anchor 136. The hook arm 130 is connected to a follower arm 138 by an adjustable linkage 140. The follower arm 138 is driven in opposite directions (represented by arrows 142) by a clockwork spring drive assembly 144, which, in turn, moves the hook arm 130 and drive member 95 between their extended and retracted positions.

Figure 15:
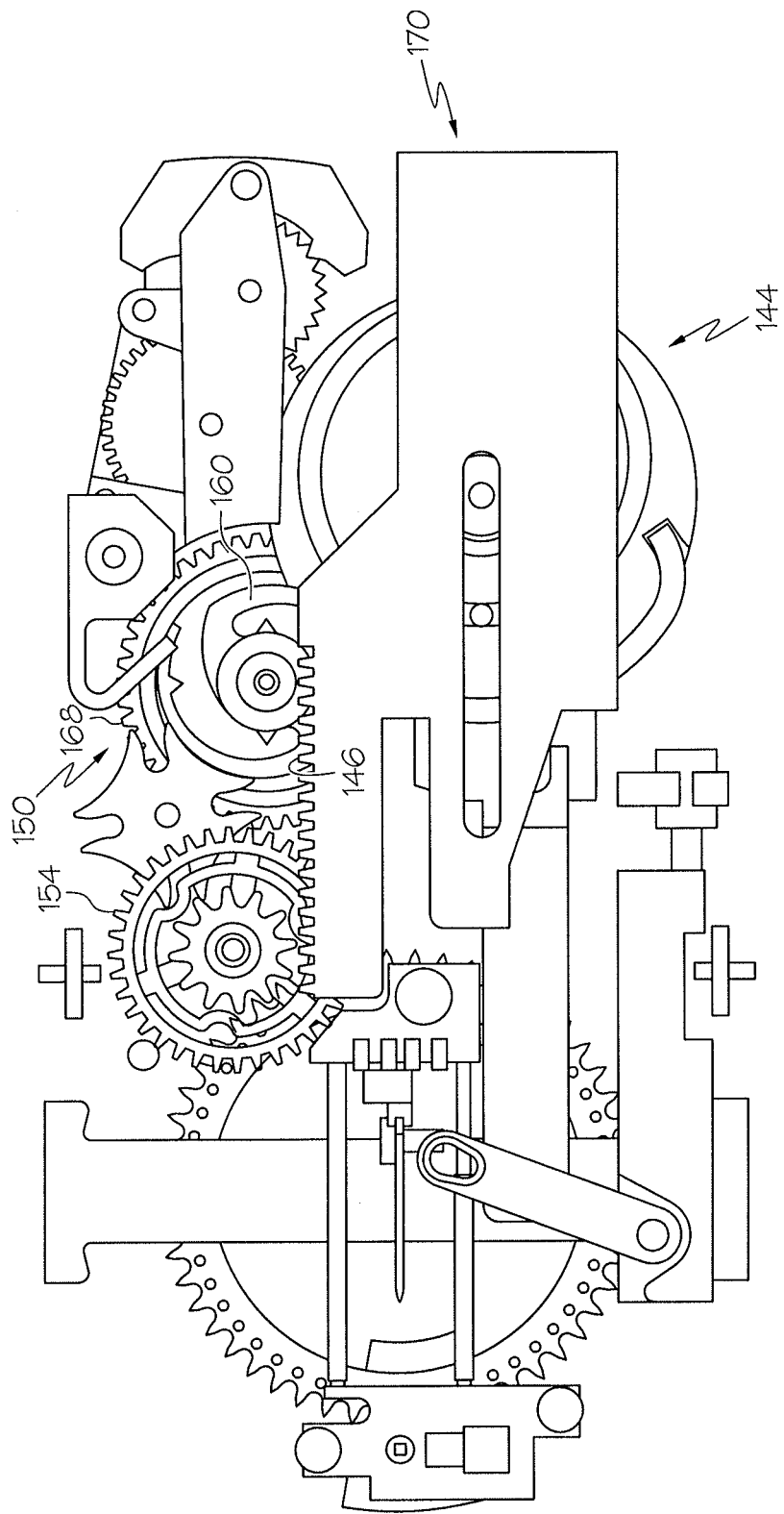
FIG. 15 is an isolated view of an embodiment of a spring-drive motor for use in the portable handheld medical diagnostic device of FIG. 14.

Referring also to FIG. 15, the rack member 146 is used to wind the clockwork spring drive assembly 144 via a gear wind assembly 150. The rack member 146 includes teeth 154 extending along its length that are meshed with teeth 160 (FIG. 14) of a cam gear 162 having arms 164 and 166 that can engage a drive gear 168 (e.g., when rotating in only one direction, such as clockwise) for rotating the drive gear 168.

The rack member 146 is connected to a slidable cam assembly 170 (e.g., using any suitable connection, such as fasteners or by forming the rack member 146 and slidable cam assembly 170 together as one integral component such as by molding). The slidable cam assembly 170 is connected to the telescoping housing portion 25 such that movement of the telescoping housing portion 25 relative to the telescoping portion 27 moves the rack member 146 relative to the gear wind assembly 150. As can be appreciated from FIG. 15 and from the description below, movement of the rack member 146 in the direction of arrow 176 causes the cam gear 162 to rotate in the clockwise direction. Rotating clockwise, the cam gear 162 may not engage the drive gear 168 and may rotate relative thereto. Thus, moving the telescoping portion 27 outwardly in the direction of arrow 176 places the rack member 146 in a preload or pre-primed position that is ready to wind or prime the clockwork spring drive assembly 144 during its return stroke. Movement of the rack member 146 in a direction opposite arrow 176 causes the cam gear 162 to rotate in the counterclockwise direction. Rotating counterclockwise, the cam gear 162 engages the drive gear 168, which, in turn, winds the adjacent clockwork spring drive assembly 144, as will be described in greater detail below.

Figure 16:
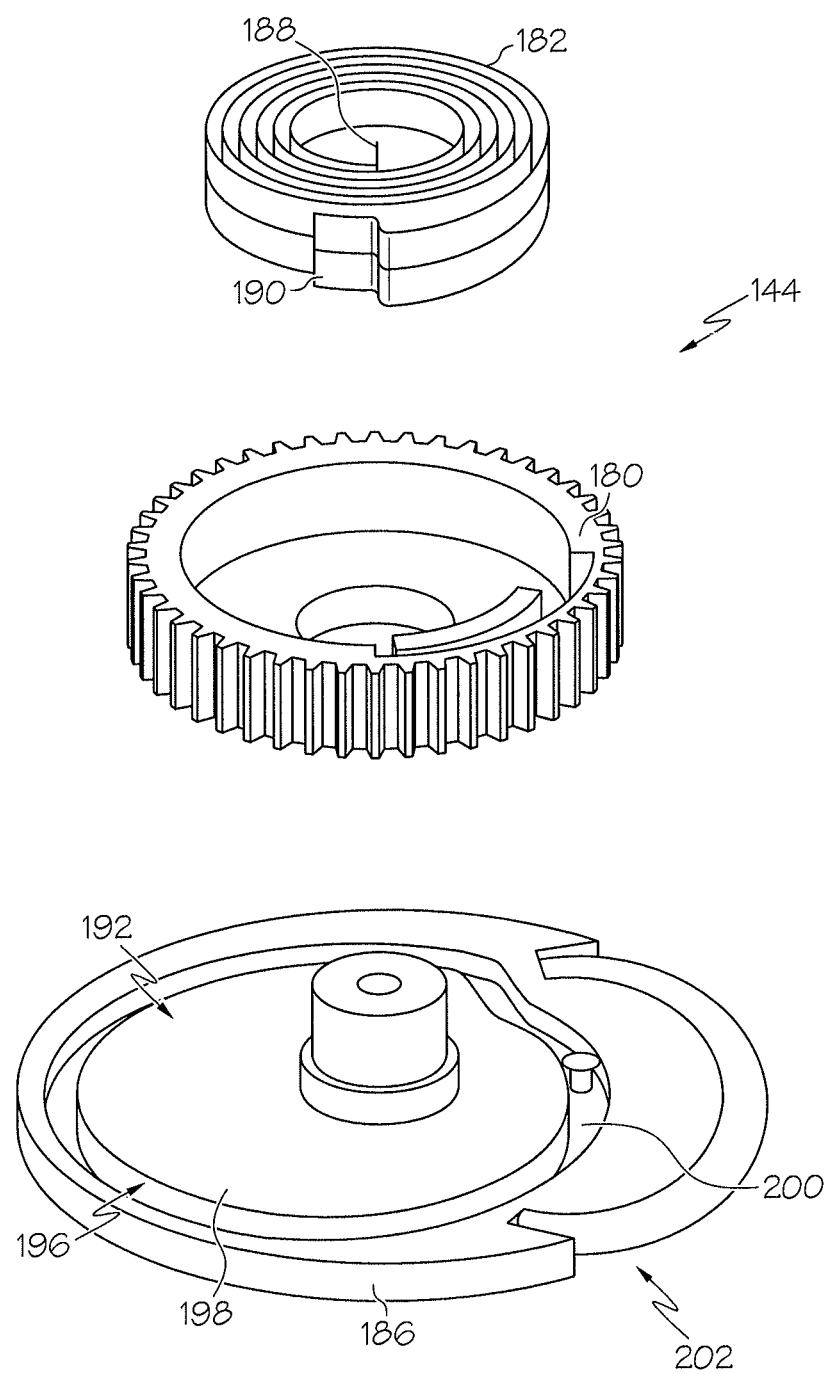
FIG. 16 is an exploded view of an embodiment of a clockwork spring drive assembly for use in the spring-drive motor of FIG. 15.

FIG. 16 illustrates an exploded view of the exemplary clockwork spring drive assembly 144 in isolation. The clockwork spring drive assembly 144 includes a spring wheel 180, a torsion spring 182 and a roller wheel 186. The spring 182 connects the spring wheel 180 to the roller wheel 186. At an inner end 188, the spring 182 is connected to the roller wheel 186, while at an outer end 190, the spring 182 is connected to the spring wheel 180. Rotation of the spring wheel 180 relative to the roller wheel 186 about a pivot axle causes the spring 182 to wind thereby increasing the stored energy in the spring 182.

The roller wheel 186 includes a face cam portion 192 including a groove 196 that is provided at a face 198 of the roller wheel 186. The groove 196 provides a track that is followed by the follower arm 138 (FIG. 14) such that the follower arm 138 is moved a fixed distance between extended and retracted positions as the roller wheel 186 rotates. A follower pin 200 is provided at an opposite face 202 of the roller wheel 186. Rotation of the roller wheel 186 (and thus movement of the follower arm) is controlled through interaction between the follower pin 200 and a cam track portion of the slidable cam assembly 170.

Figure 17:
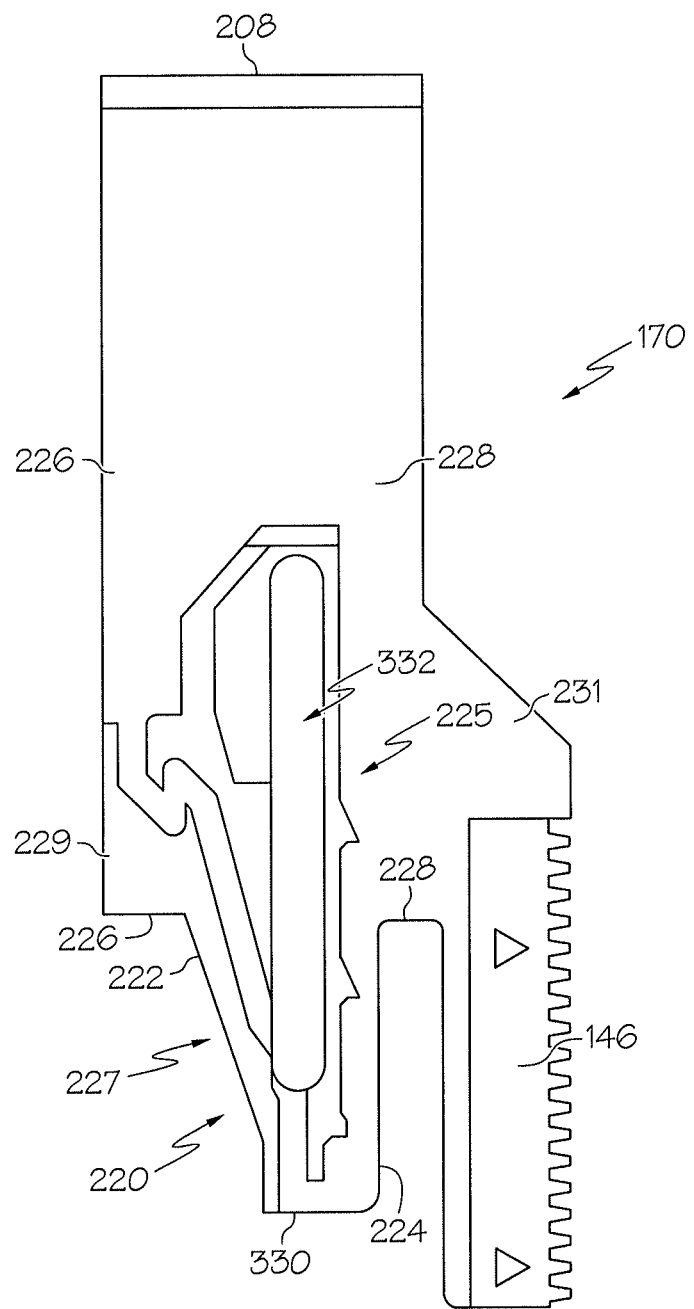
FIG. 17 is a top view of an embodiment of a slidable cam assembly for use with the spring-drive motor of FIG. 15.

Referring to FIG. 17, the slidable cam assembly 170 is depicted in isolation and includes a track portion 220 that extends outwardly from an end 208 and generally parallel to the rack member 146. The track portion 220 is formed by a pair of track support members 222 and 224 that are cantilevered at one end 226 and 228 to the end 208 and extend outwardly to a joined free end 330. A slot 332 extends along a length of the track portion 220 that is sized to receive the pivot axle 187 (FIG. 14) of the clockwork spring drive assembly 144 such that the slidable cam housing assembly 170 can slide by the pivot axle 187. Carried by each of the track support members 222 and 224 is a respective elongated guide track element 225 and 227 that extends upwardly from top surfaces 229 and 231 of each track support member 222 and 224. The guide track elements 225 and 227 are used to control winding and releasing of the clockwork spring drive assembly 144 by controlling (i.e., allowing and disallowing) rotation of the roller wheel 186.

Figure 18:
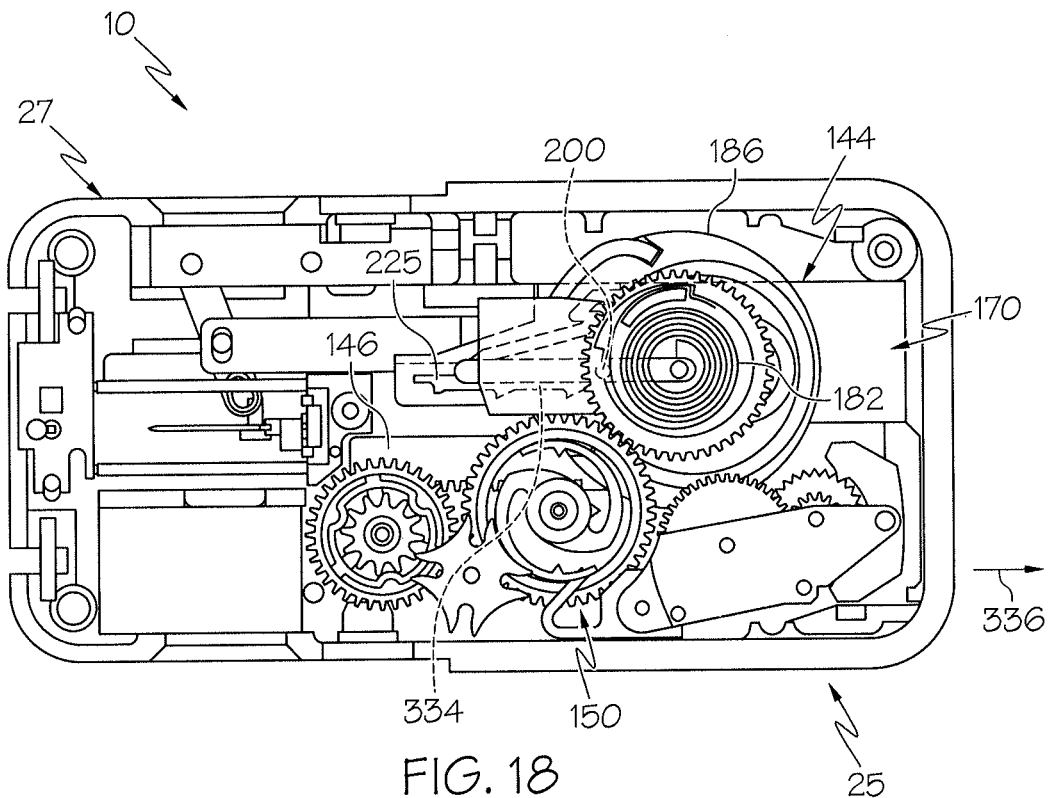
FIG. 18 illustrates the slidable cam assembly of FIG. 17 in operation with the spring-drive motor of FIG. 16.
Figure 19:
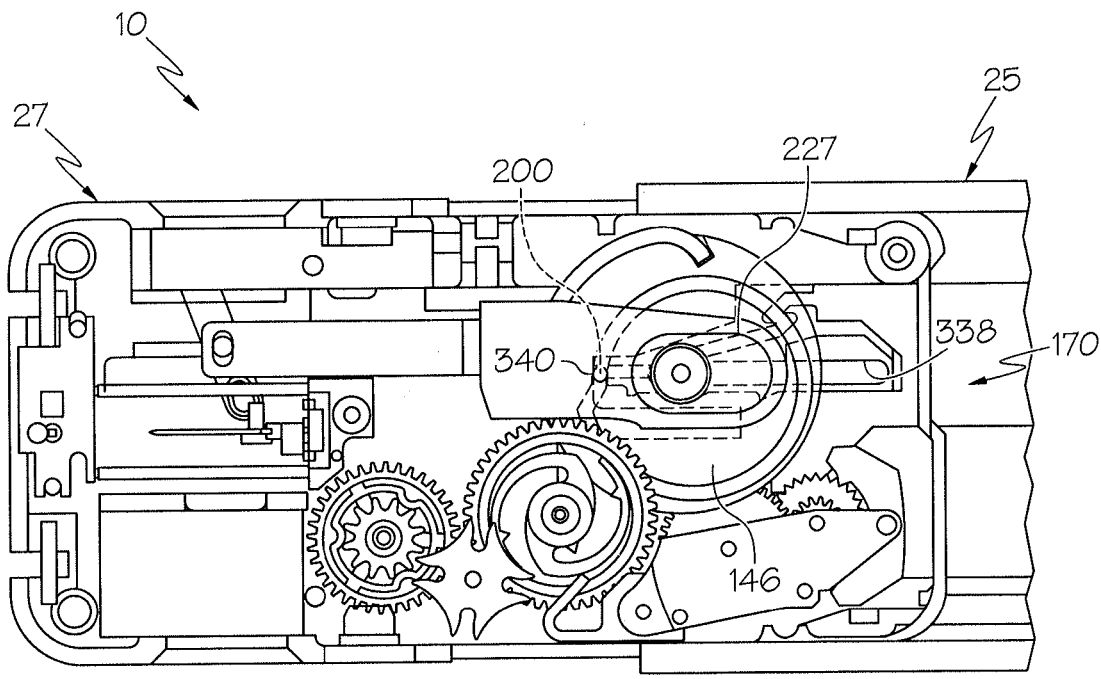
FIG. 19 illustrates the slidable cam assembly of FIG. 17 in operation with the spring-drive motor of FIG. 16.

FIGS. 18-22 illustrate a priming and firing sequence utilizing the clockwork spring drive assembly 144, the gear wind assembly 150, the rack member 146 and the slidable cam assembly 170. The roller wheel 186 is shown somewhat transparent such that the follower pin 200 can be seen as it interacts with the track portion 220 and the guide track elements 225 and 227. FIG. 18 illustrates the roller wheel 186 and the slidable cam assembly 170 in a start position with the follower pin 200 biased clockwise against a wall portion 334 of the guide track element 225 by the spring 182. In this position, the slidable cam assembly 170 can be pulled in the direction of arrow 336 relative to the clockwork spring drive assembly 144 through the connection of the slidable cam assembly 170 with the housing portion 25 and due to the clockwork spring drive assembly 144 being rotatably connected to the housing portion 27. FIG. 19 illustrates the slidable cam housing assembly 170 in a fully pre-primed position with the follower pin 200 biased against a wall portion 338 of the guide track element 227. As indicated above, movement of slidable cam housing assembly 170 and the rack member 146 connected thereto (FIG. 14) in the direction of arrow 336 causes the cam gear 162 to rotate in the clockwise direction. Rotating clockwise, the cam gear 162 may not engage the drive gear 168 and may rotate relative thereto without winding the spring 182. However, the spring 182 may be preloaded an amount such that the follower pin 200 moves against the guide track element 225, over an edge 340 of the guide track element 225 and to the wall portion 338 of the guide track element 227 in the fully pre-primed position.

Figure 20:
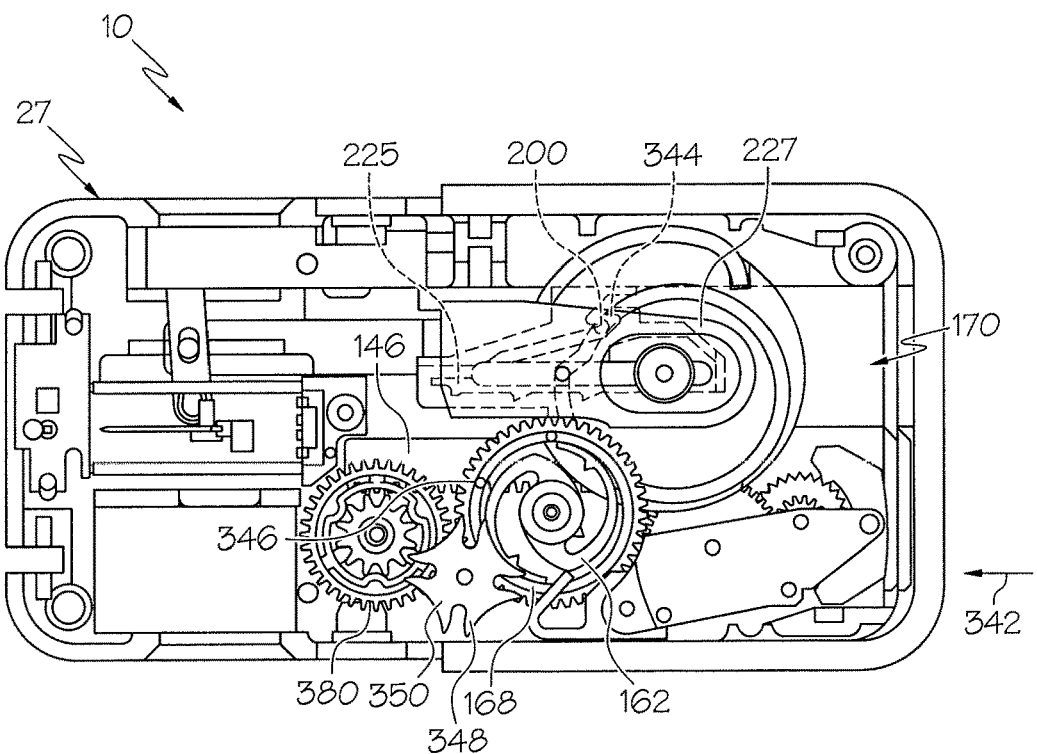
FIG. 20 illustrates the slidable cam assembly of FIG. 17 in operation with the spring-drive motor of FIG. 16.

Referring now to FIG. 20, the slidable cam assembly 170 may be pushed in the direction of arrow 342 toward a wound, triggerable position (or primed position) once placed in the fully pre-primed position with the follower pin between the guide track elements 225 and 227. As the slidable cam assembly 170 is pushed in the direction of arrow 342, the movement of slidable cam assembly 170 and the rack member 146 connected thereto (FIG. 14) in the direction of arrow 342 causes the cam gear 162 to rotate in the counterclockwise direction. Rotating counterclockwise, the cam gear 162 engages the drive gear 168 thereby rotating the spring wheel 180 and winding the spring 182 (FIG. 14). The guide track element 227 prevents rotation of the roller wheel 186, which allows the spring 182 to wind relative to the roller wheel 186 as the spring wheel 180 rotates.

As the drive gear 168 rotates counterclockwise, a gear engaging pin 346 moves toward a slot 348 of a Geneva wheel gear 350. The Geneva wheel gear 350 is a gear mechanism that translates a continuous rotation of the drive gear 168 into an intermittent rotary motion as the gear engaging pin 346 travels through the slot 348. The Geneva wheel gear 350 is engaged with a disk drive gear 380 that, in turn, is engaged with the teeth 81 of the disk indexing structure 66 (FIG. 7). The intermittent rotary motion of the Geneva wheel gear 350 causes an indexing motion of the disk component 51 to bring an adjacent lancet compartment 40 in line with the lancet port 20.

The follower pin 200 follows along the guide track element 227 until the follower pin 200 reaches an initial stop 344. The follower pin 200 may then be rotated into the initial stop 344 due to the bias force provided on the roller wheel 186 by the spring 182. With the follower pin 200 in this position, the slidable cam assembly 170 is in a primed, safety-ready position. An actuating motion causes the slidable cam housing assembly 170 to move a relatively short distance in the pull direction of arrow 336, which allows the follower pin 200 to move to a final stop 345 past an edge 352 of the guide track element 227 and into the wound, triggerable position illustrated by FIG. 21.

Figure 21:
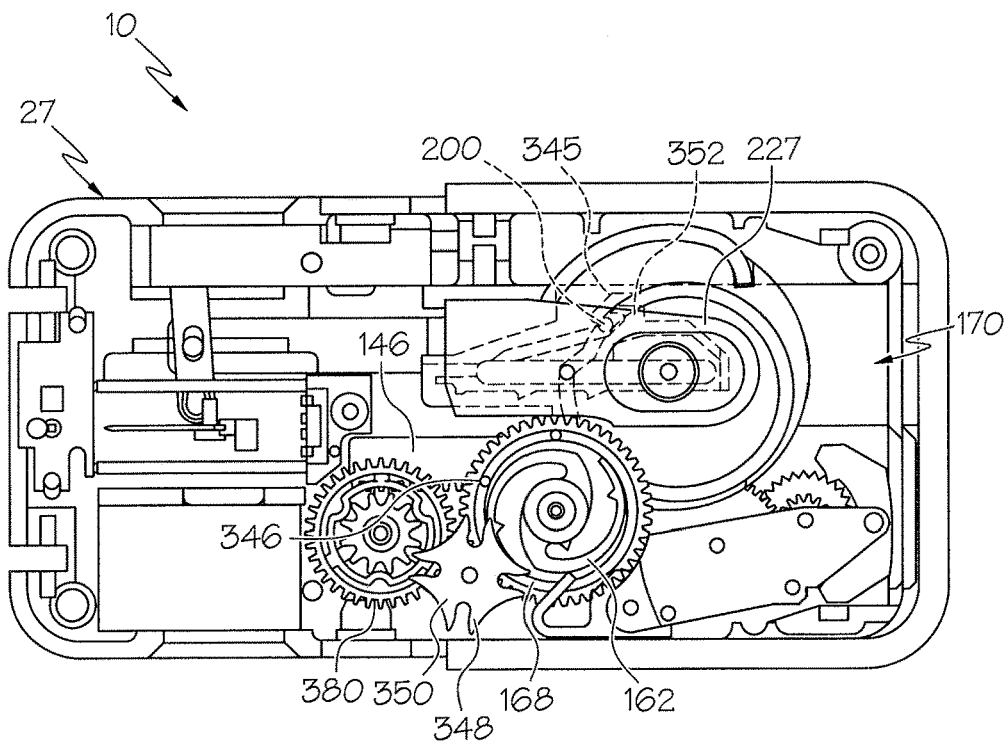
FIG. 21 illustrates the slidable cam assembly of FIG. 17 in operation with the spring-drive motor of FIG. 16.
Figure 22:
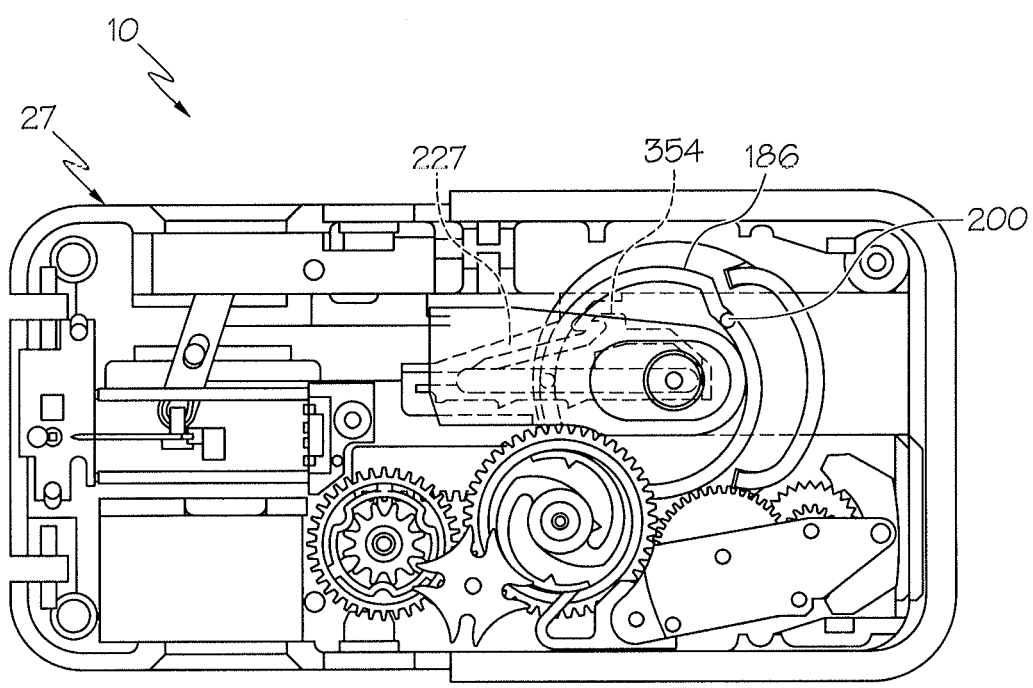
FIG. 22 illustrates the slidable cam assembly of FIG. 17 in operation with the spring-drive motor of FIG. 16 and an embodiment of a speed control mechanism.

Once the follower pin 200 is in the wound, triggerable position of FIG. 21, the medical diagnostic device 10 is ready to fire the lancet structure 24 through the lancet port 20. Triggering the medical diagnostic device 10 may be accomplished by placing the finger or other body part on the lancet port 20, pushing the housing portion 25 toward the housing portion 27. Referring to FIG. 22, the roller wheel 186 rotates due to the bias provided by the spring 182 once the follower pin 200 moves beyond a release point 354 provided by the guide track element 227. Rotation of the roller wheel 186 causes the lancet structure 24 to extend outwardly from the lancet port 20 and retract back into the lancet port 20.

In some embodiments, an illustrative velocity over time profile of the lancet structure 24 is illustrated. As can be seen, portion A shows engagement of the drive member with the lancet structure 24 and portion B shows relatively rapid acceleration of the lancet structure 24 as the skin penetrating end 90 approaches and penetrates a skin site. Portion C shows relatively slow acceleration of the lancet structure 24 as the skin penetrating end exits the skin site. Such slower acceleration can allow for drawing of the fluid sample (e.g., 100 nL) from the skin site. Portion D shows a higher acceleration after portion B during retraction of the lancet structure 24. In some embodiments, a ratio of time during the extending phase to time during the retracting phase is at least about 1:25. Deceleration is adjustable by, for example, increasing or decreasing spring bias on the ratchet mechanism 368 and/or by changing the gear ratio.

Figure 23:
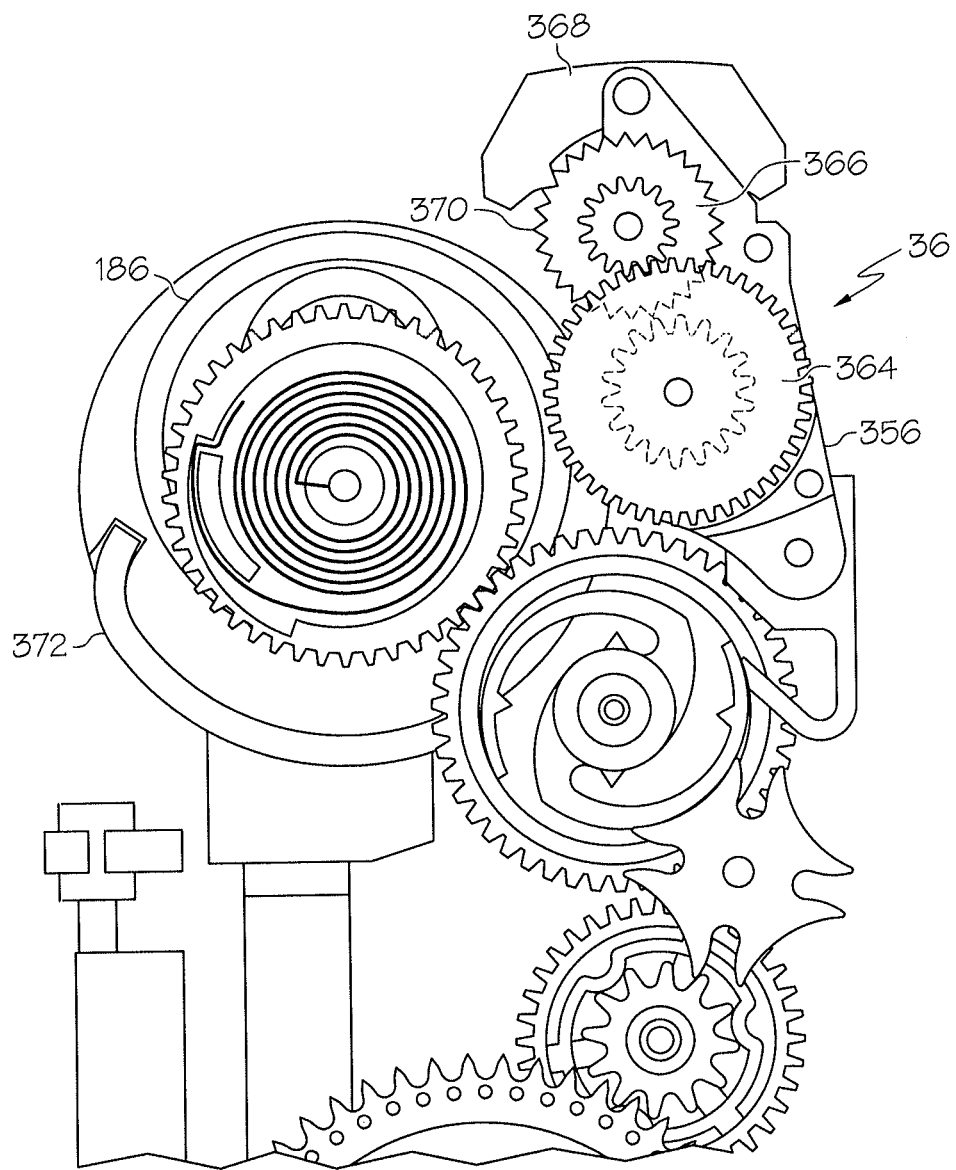
FIG. 23 illustrates components of the speed control mechanism of FIG. 22 in isolation.

Referring again to FIG. 14 and also to FIG. 23, the speed control mechanism 36 may be a gearbox and includes a housing 356, gears 364 and 366 and ratchet mechanism 368. The gear 364 is an engagement gear and engages the clockwork spring drive assembly 144 as the roller wheel 186 rotates. In one embodiment, the roller wheel 186 includes an eccentric ring member 372 (e.g., formed of rubber or plastic) that increases the diameter of the roller wheel 186 at a particular location at the periphery of the roller wheel 186. As the roller wheel 186 rotates during the return stroke of the lancet structure 24, the eccentric ring member 372 frictionally engages the gear 364 thereby rotating the gear 364 and slowing the roller wheel 186. As the gear 364 rotates, it causes the gear 366 to rotate. The ratchet mechanism 368 engages outer teeth 370 of the gear 366 thereby slowing or otherwise controlling speed that the speed control mechanism 36 rotates.

Figure 24:
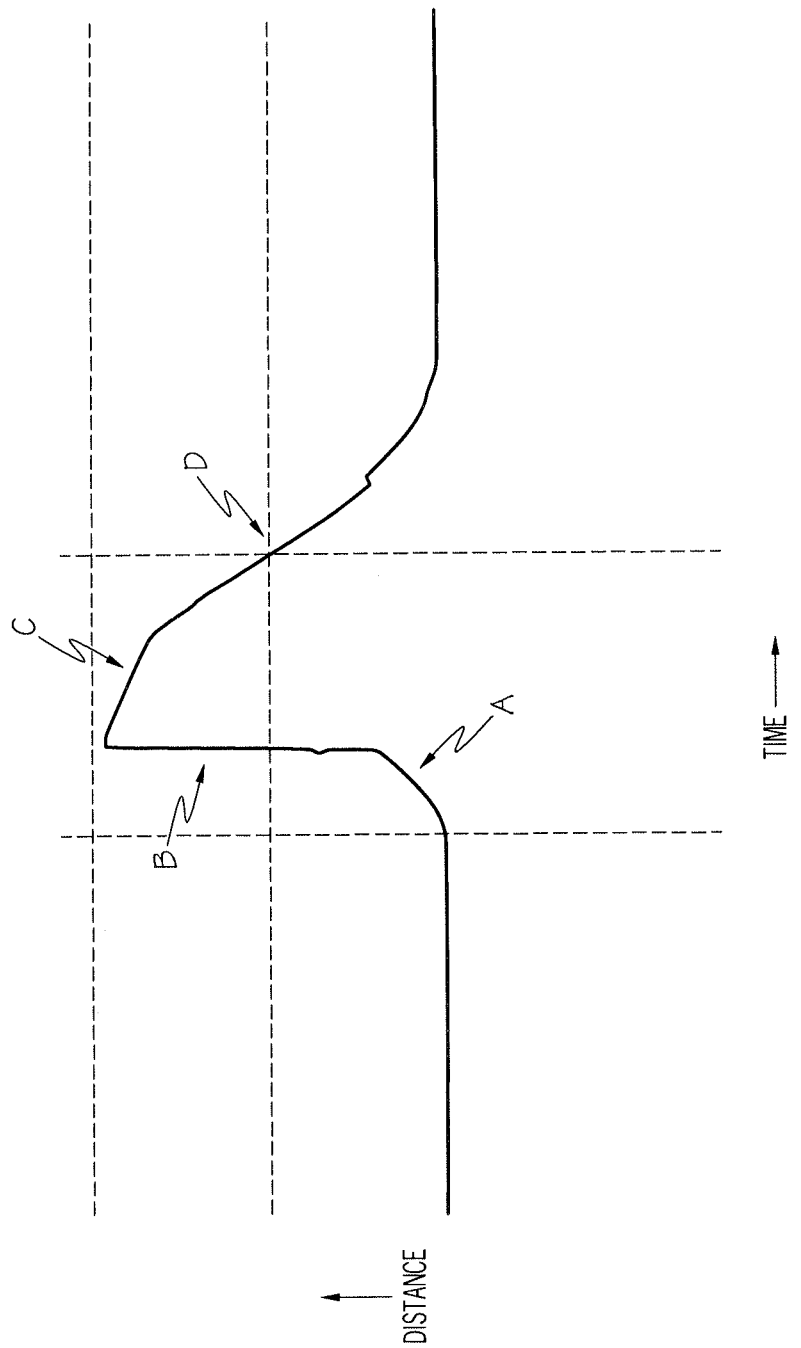
FIG. 24 illustrates an example of a velocity control profile using the speed control mechanism of FIG. 22.

Referring to FIG. 24, an illustrative velocity over time profile of the lancet structure 24 is illustrated. As can be seen, portion A shows relatively rapid acceleration of the lancet structure 24 as the skin penetrating end 90 approaches and penetrates a skin cite. Portion B shows relatively slow deceleration of the lancet structure 24 as the skin penetrating end exits the skin cite. In some embodiments, a ratio of time during the extending phase to time during the retracting phase is at least about 1:25. Deceleration is adjustable by, for example, increasing or decreasing spring bias on the ratchet mechanism 368 and/or by changing the gear ratio.

Referring again to FIG. 14, as noted above, the medical diagnostic device 10 may further include the depth adjustment mechanism 37. The depth adjustment mechanism 37 may include a thumb wheel 355 that is adjustably connected to the adjustable linkage 140 at a pivot location P1. Rotation of the thumb wheel 355 causes movement of an end 357 of the adjustable linkage 140, which, in turn, causes the adjustable linkage to pivot about pivot location P2 and adjusts the start position of the hook portion 126 of the drive member 95. Movement of the hook portion 126 of the drive member 95 toward the lancet port 20 can increase the penetration depth of the skin penetrating end 90 of the lancet structure 24 due to the fixed stroke length of the follower arm 138 and roller wheel 186. Movement of the hook portion 126 of the drive member 95 away from the lancet port 20 can decrease the penetration depth of the skin penetrating end 90 of the lancet structure 24. As one exemplary embodiment, the penetration depth (e.g., the distance the skin penetrating end 90 extends beyond the lancet port 20) may be adjustable from about 0.8 mm to about 2.3 mm. Additionally, because the follower arm 138 is connected to the adjustable linkage 140 (e.g., at slot 381) for extending and retracting the drive member 95, the adjustable linkage 140 may act to amplify movement of the drive member 95 relative to movement of the follower arm 138. In some embodiments, the adjustable linkage 140 provides a multiplier of 1.8:1 ratio of the drive member 95 to the follower arm 138.

Figure 25:
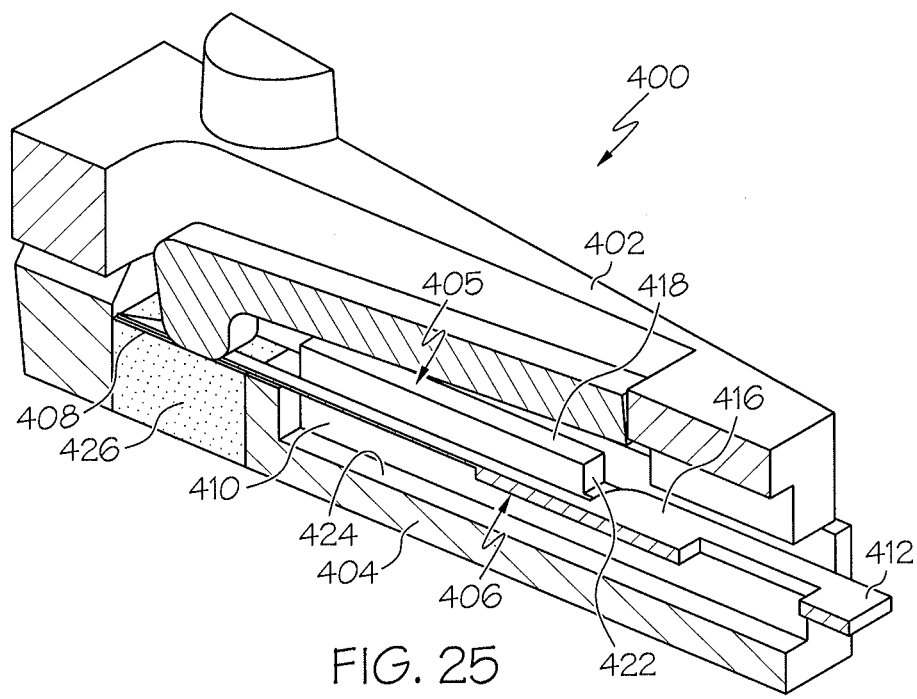
FIG. 25 illustrates another embodiment of a lancet housing assembly.

Referring now to FIG. 25, an alternative embodiment of a lancet housing assembly 400 (e.g., in the form of a disk) includes an upper disk member 402 and a lower disk member 404 defining a lancet compartment 405. A lancet structure 406 includes a skin penetrating end 408, a blood transfer portion 410 and engagement structure 412 for engaging a drive member 414. Similar to the embodiments described above, the lancet structure 406 includes a laterally extending wing 416 that can ride along a side rail 418 extending along a side wall 420 of the lancet compartment 405. In this embodiment, the side rail 418 includes a step 422 that causes the lancet structure 406 to move (i.e., snap down) toward a lancet floor 424, release the driver member and bring the skin penetrating end 408 in contact with a reagent material 426. In the illustrated embodiment, the step 422 is substantially parallel to vertical (i.e., perpendicular to the side rail 418), however, the step may be at other angles to vertical.

Figure 26:
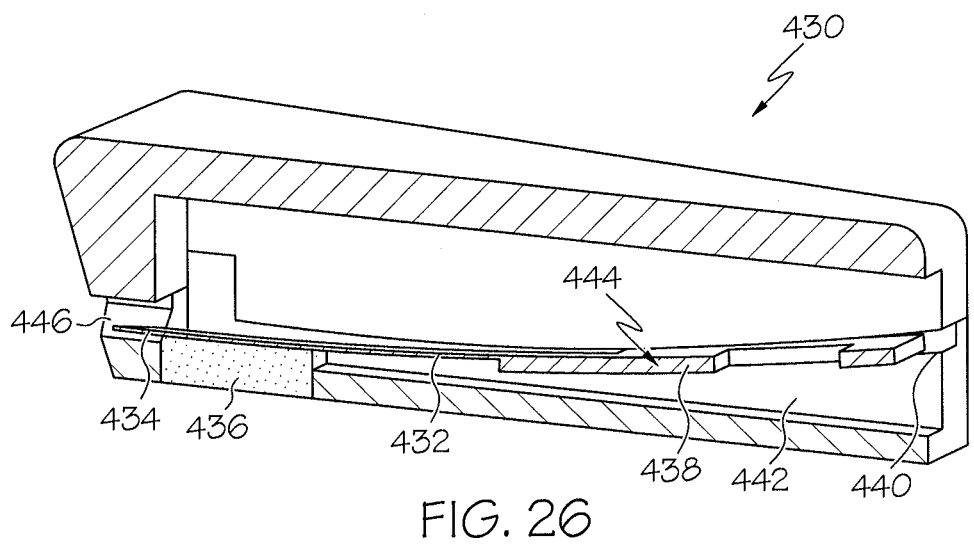
FIG. 26 illustrates another embodiment of a lancet housing assembly.

Referring to FIG. 26, another embodiment of a lancet housing assembly 430 may utilize a curvature of a lancet structure 432 to bring a skin penetrating end 434 of the lancet structure 432 in contact with a reagent material 436. In this embodiment, the lancet structure 432 includes a laterally extending wing 438 that can ride along a curved side rail 440 extending along a side wall 442 of the lancet compartment 444. When the skin penetrating end 434 is pulled by the opening 446, the curvature of the lancet structure 432 causes the skin penetrating end 434 to come into contact with the reagent material 436.

Figure 27:
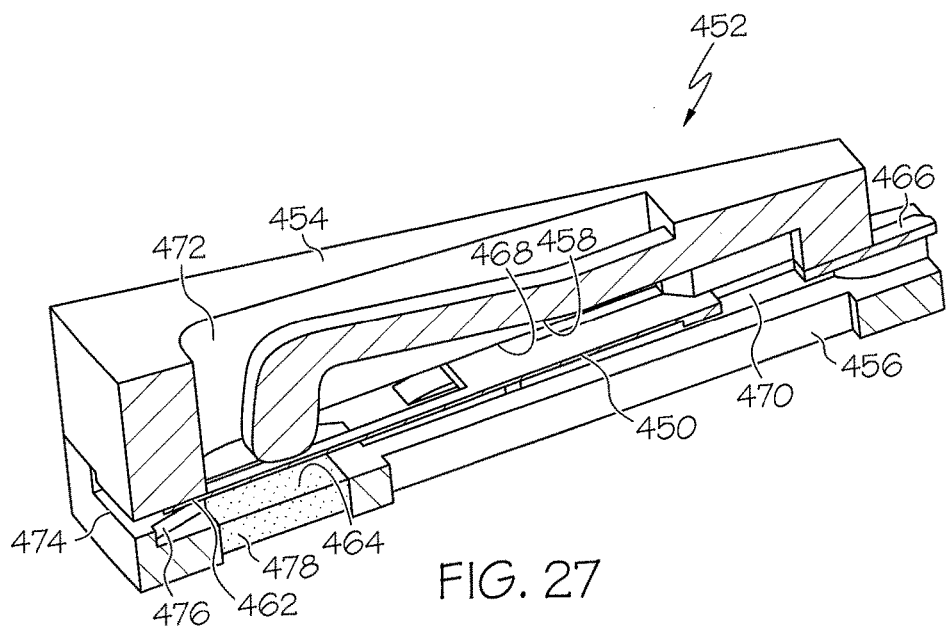
FIG. 27 illustrates another embodiment of lancet housing assembly.
Figure 28:
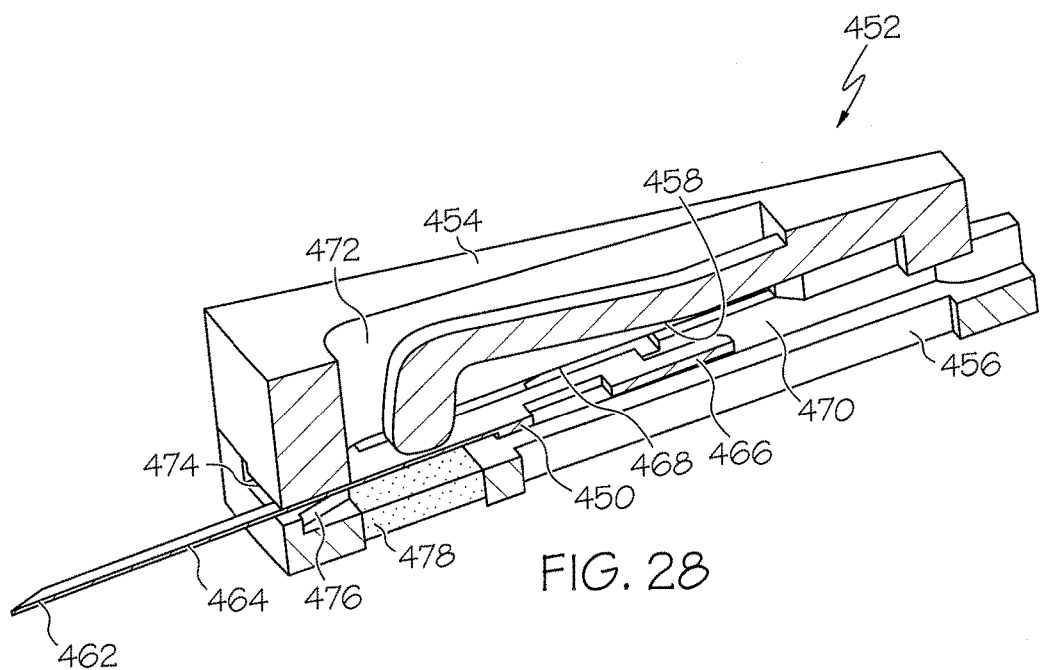
FIG. 28 illustrates the lancet housing assembly of FIG. 27 in operation.
Figure 29:
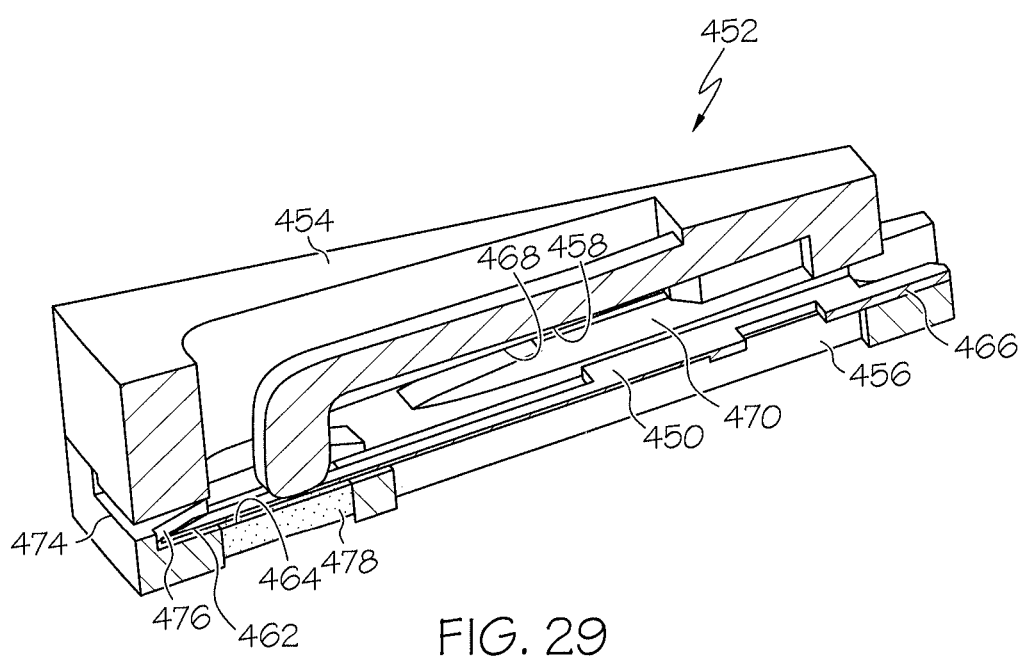
FIG. 29 illustrates the lancet housing assembly of FIG. 27 in operation.

Referring to FIGS. 27-29, movement of a lancet structure 450 may have a lateral or sideways component (i.e., angular movement toward an adjacent lancet compartment). A lancet housing assembly 452 (e.g., in the form of a disk) includes an upper disk member 454 and a lower disk member 456 defining the lancet compartment 458. The lancet structure 450 includes a skin penetrating end 462, a blood transfer portion 464 and engagement structure 466 for engaging a drive member. Similar to the embodiments described above, the lancet structure 450 includes a laterally extending wing 468 that can ride along a side rail 470 extending along a side wall 472 of the lancet compartment 458. In this embodiment, the opening 474 includes a horizontal wall component 476 that forces the skin penetrating end 462 laterally toward an adjacent lancet compartment to bring the lancet structure 450 into contact with a reagent material 478.

FIGS. 30-42 illustrate another embodiment of a lancet housing assembly 500 including an upper disk member 502 and a lower disk member 504 defining a lancet compartment 505. A lancet structure 506 includes a skin penetrating end 508, a blood transfer portion 510 and engagement structure 512 for engaging a drive member 514. Referring first to FIG. 30, securing structure 516 is provided for securing the lancet structure 506 within the lancet compartment 505. The securing structure 516 allows some force to be placed on the lancet structure 506 during engagement of the drive member 514 therewith without longitudinal displacement of the lancet structure 506. Yet, the securing structure 516 may allow for longitudinal displacement of the lancet structure 506 in response to a force above a preselected threshold force.

The securing structure 516 may include spring elements 518 and 520 that extend outwardly from the extended axis of the lancet structure 506. The spring elements 518 and 520 may each be received within a respective notch 522 and 524, which are sized to receive the spring elements 518 and 520. The locking strength of the securing structure 516 can be selected using the spring strength of the spring elements 518 and 520 and the exit angle of the notches 522 and 524. In this embodiment, the exit angles of the notches 522 and 524 are less than about 90 degrees.

FIG. 31 illustrates a starting position including the drive member 514 with the lancet structure 506 engaged with the securing structure 516. Wing structures 526 and 528 may be provided (FIG. 30) that rest upon support structures 530 to space the lancet structure 506 from a reagent material 532. The drive member 514 may be inserted into the lancet compartment 505 and pushed forwards, in a manner similar to that described above. In some embodiments, the drive member 514 is subjected to an upward spring force F (e.g., using a spring), which also is shown by FIG. 32.

Figure 32:
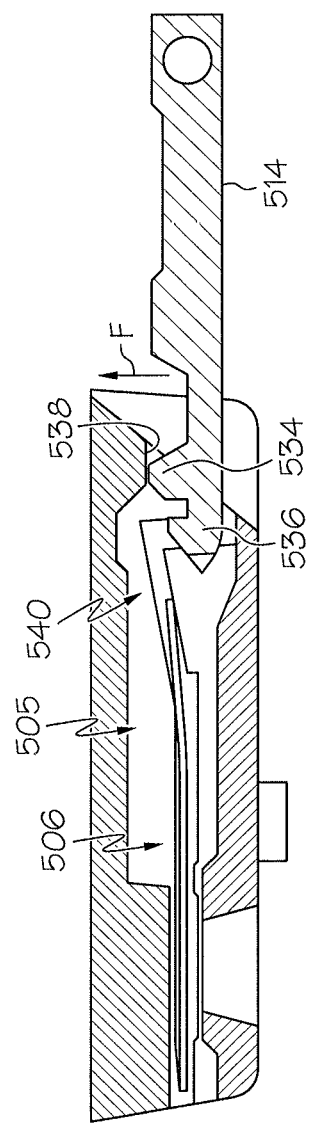
FIG. 32 illustrates the lancet housing assembly of FIG. 30 in operation.
Figure 33:
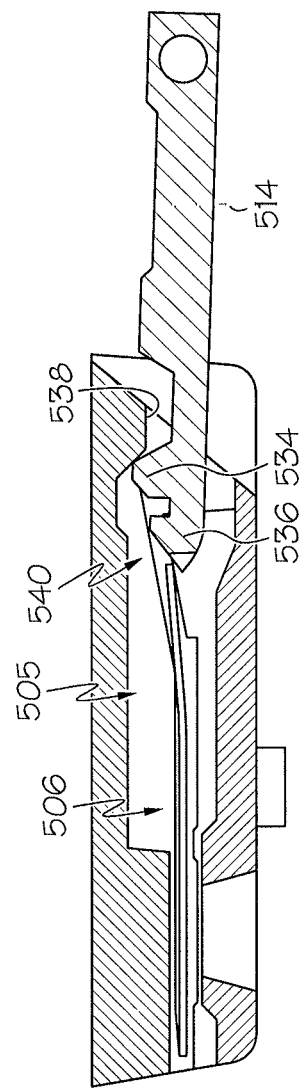
FIG. 33 illustrates the lancet housing assembly of FIG. 30 in operation.

In FIG. 32, the drive member 514 includes a guide projection 534 having a rounded outer periphery and extending upwardly from the hook portion 536. The guide projection 534 may engage a downwardly extending cam surface 538 to force the hook portion 536 downward to position the hook portion 536 for engagement with engagement structure 540 of the lancet structure 506. Referring to FIG. 33, as the guide projection 534 moves past the cam surface 538, the hook portion 536 raises due to the bias F and engages the engagement structure 540 of the lancet structure 506.

In FIG. 34, the spring elements 518 and 520 (FIG. 30) may free from the notches 522 and 524 and at FIG. 35, a landing member 542 may engage the cam surface 538 to limit upward movement of the hook portion 536. At FIGS. 36 and 37, an incision may be made by moving the skin penetrating end 508 through the opening 544 followed by decelerated return movement, in a fashion similar to that described above.

Figure 40:
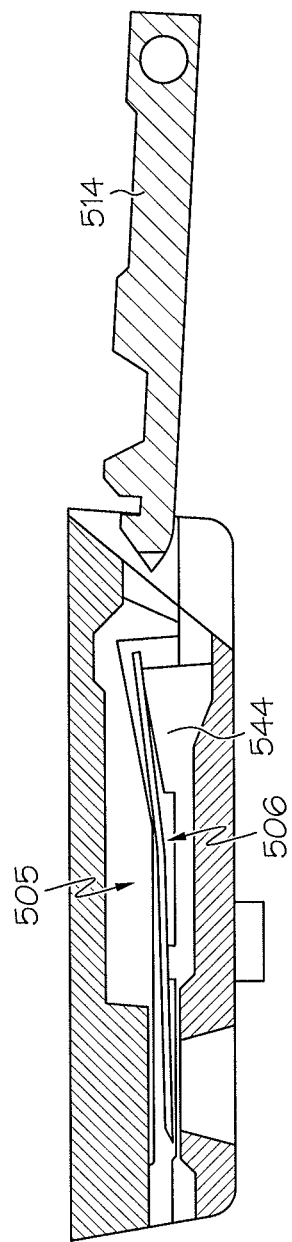
FIG. 40 illustrates the lancet housing assembly of FIG. 30 in operation.

Referring to FIG. 38, at the end of the return movement of the lancet structure 506, the bias force F acts on the lancet structure 506 thereby tensioning the lancet structure 506. With the wing structures 526 and 528 (FIG. 30) resting upon support structures 530, a gap remains between the lancet structure 506 and the reagent material 532 as shown by FIG. 38. Referring to FIG. 39, with further return movement of the drive member 514, the wing structures 526 and 528 (FIG. 30) disengage the support structures 530 and the skin penetrating end 508 contacts the reagent material 532. The bias force F facilitates contact between the skin penetrating end 508 and the reagent material 532 such that a liquid contact takes place. Upon further return of the drive member 514, the guide projection 534 engages the cam surface 538 forcing the hook portion 536 to disengage the lancet structure 506 as shown by FIG. 39. Referring to FIG. 40, ribs 544 may be provided to maintain spring tension within the lancet structure 506.

Figure 41:
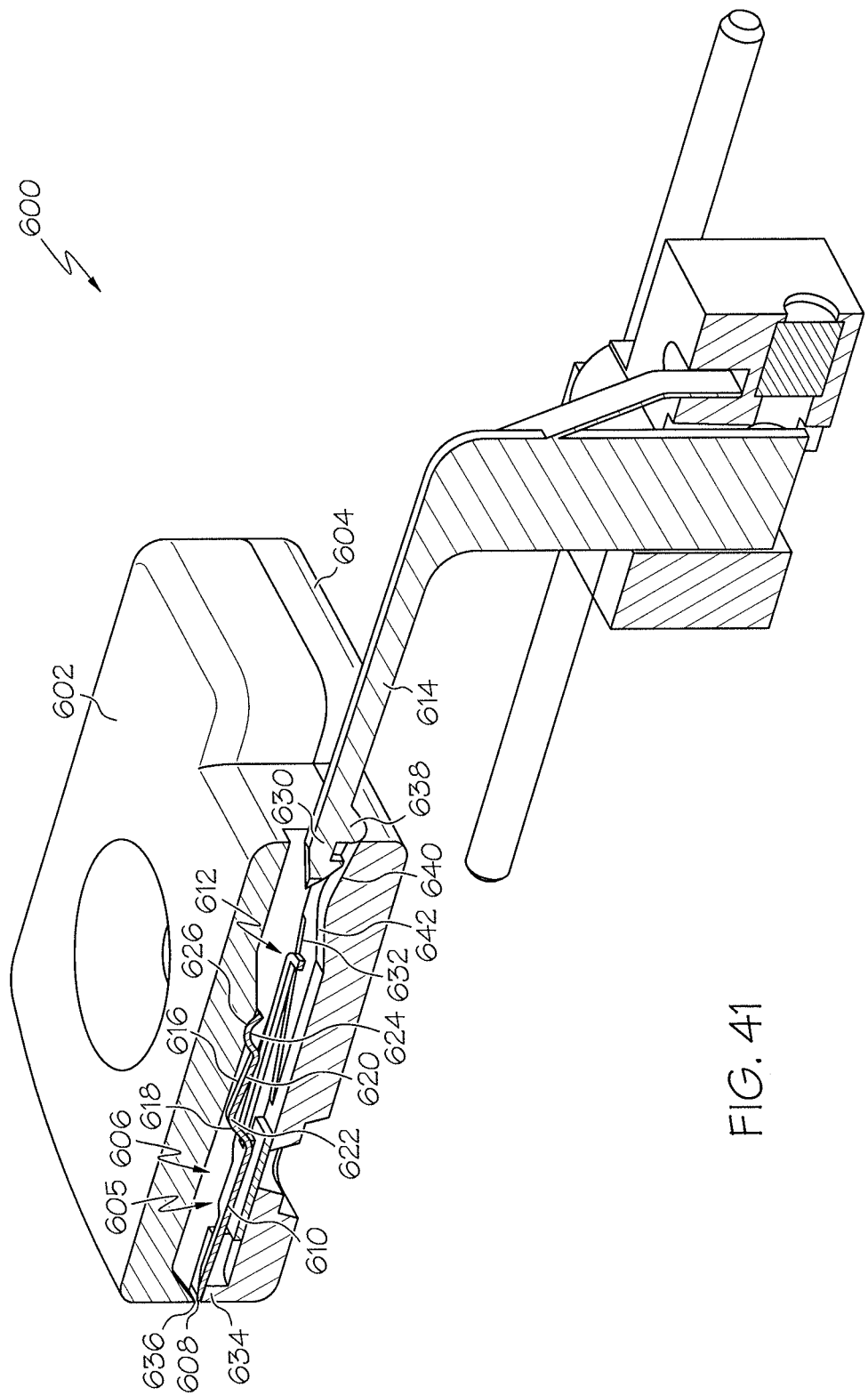
FIG. 41 illustrates another embodiment of lancet housing assembly.

FIGS. 41-48 illustrate another embodiment of a lancet housing assembly 600 including an upper disk member 602 and a lower disk member 604 defining a lancet compartment 605. A lancet structure 606 includes a skin penetrating end 608, a blood transfer portion 610 and engagement structure 612 for engaging a drive member 614. Referring first to FIG. 41, an initial position of the lancet structure 606 and the drive member 614 is illustrated. In this embodiment, the lancet structure 606 includes an outwardly extending spring finger 616 that extends upwardly at portion 618 and longitudinally at portion 620. A bend 622 connects the upwardly extending portion 618 and longitudinally extending portion 620. The longitudinally extending portion 620 includes a hump-shaped portion 624 that is received within a notch 626 thereby providing securing structure for the lancet structure 606 within the lancet compartment 605.

The lancet structure 606 includes engagement structure 612 that is used to engage the lancet structure 606 with a hook portion 630 of the drive member 614. In the illustrated initial position, the engagement structure 612 rests on a decline guide ramp or rail 632 that is used to support the lancet structure 606 during its extending and retracting phases. The skin penetrating end 608 of the lancet structure 606 rests on a support surface 634 at opening 636 through which the skin penetrating end 608 extends.

Figure 42:
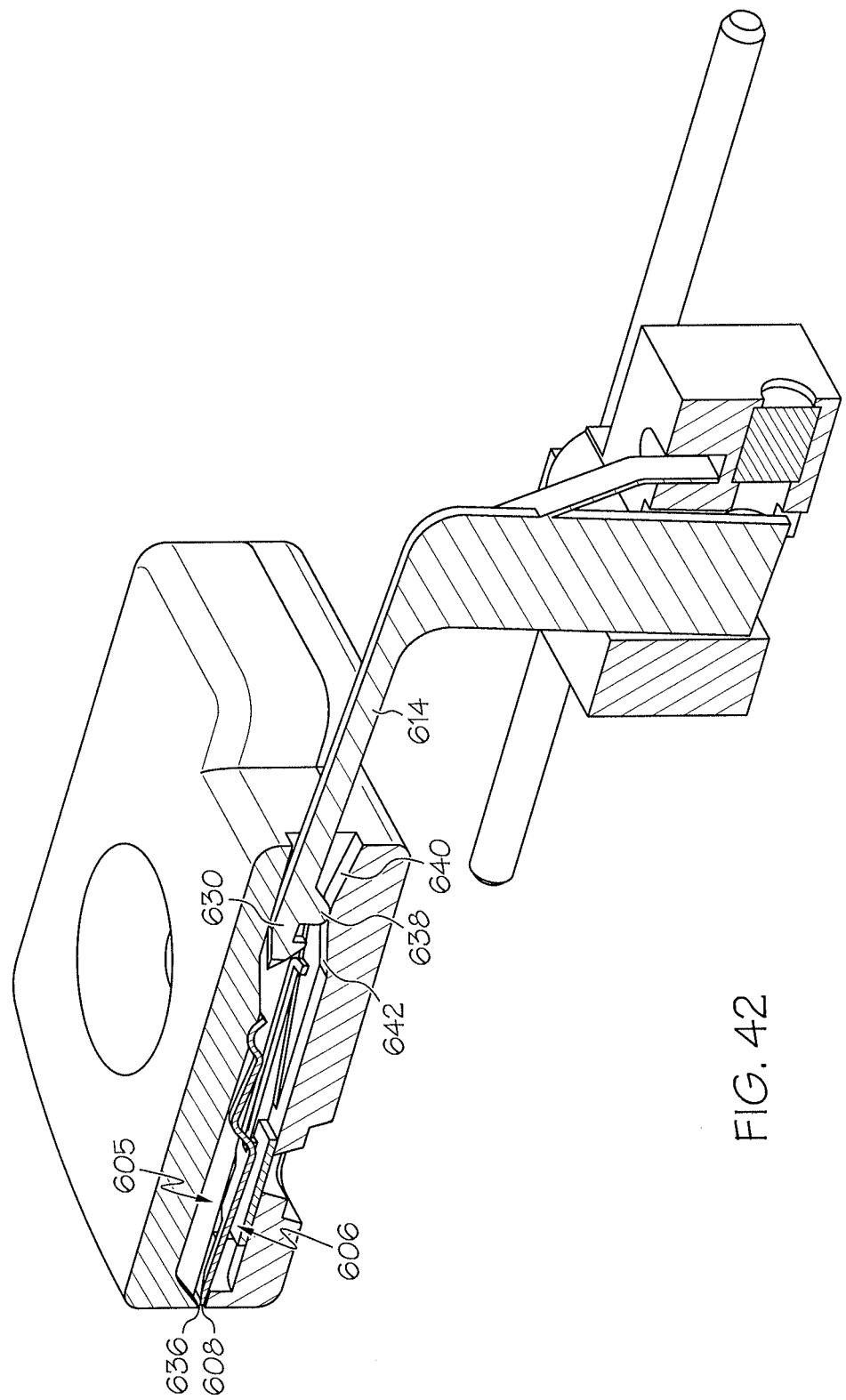
FIG. 42 illustrates the lancet housing assembly of FIG. 41 in operation.
Figure 43:
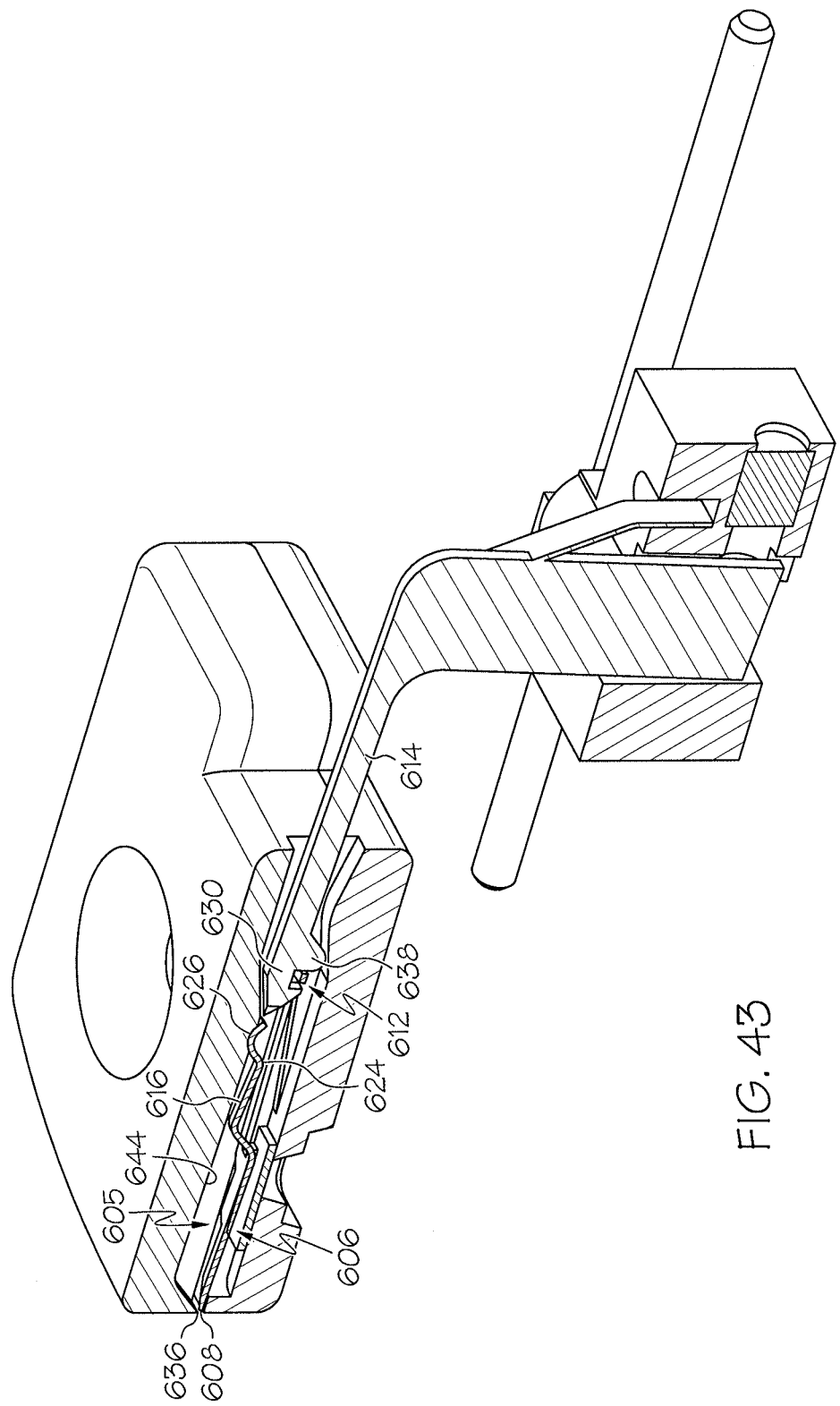
FIG. 43 illustrates the lancet housing assembly of FIG. 41 in operation.
Figure 44:
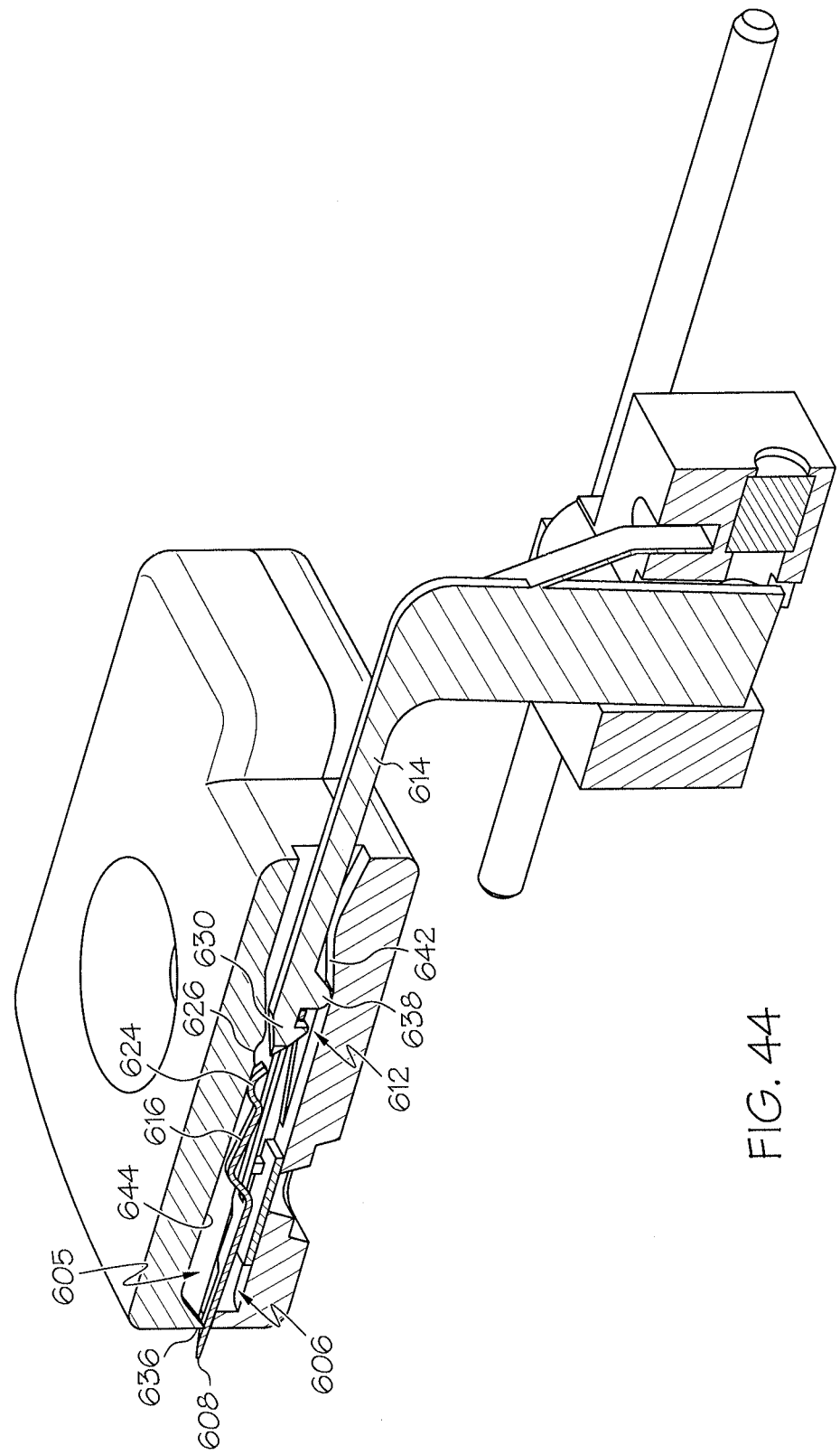
FIG. 44 illustrates the lancet housing assembly of FIG. 41 in operation.
Figure 45:
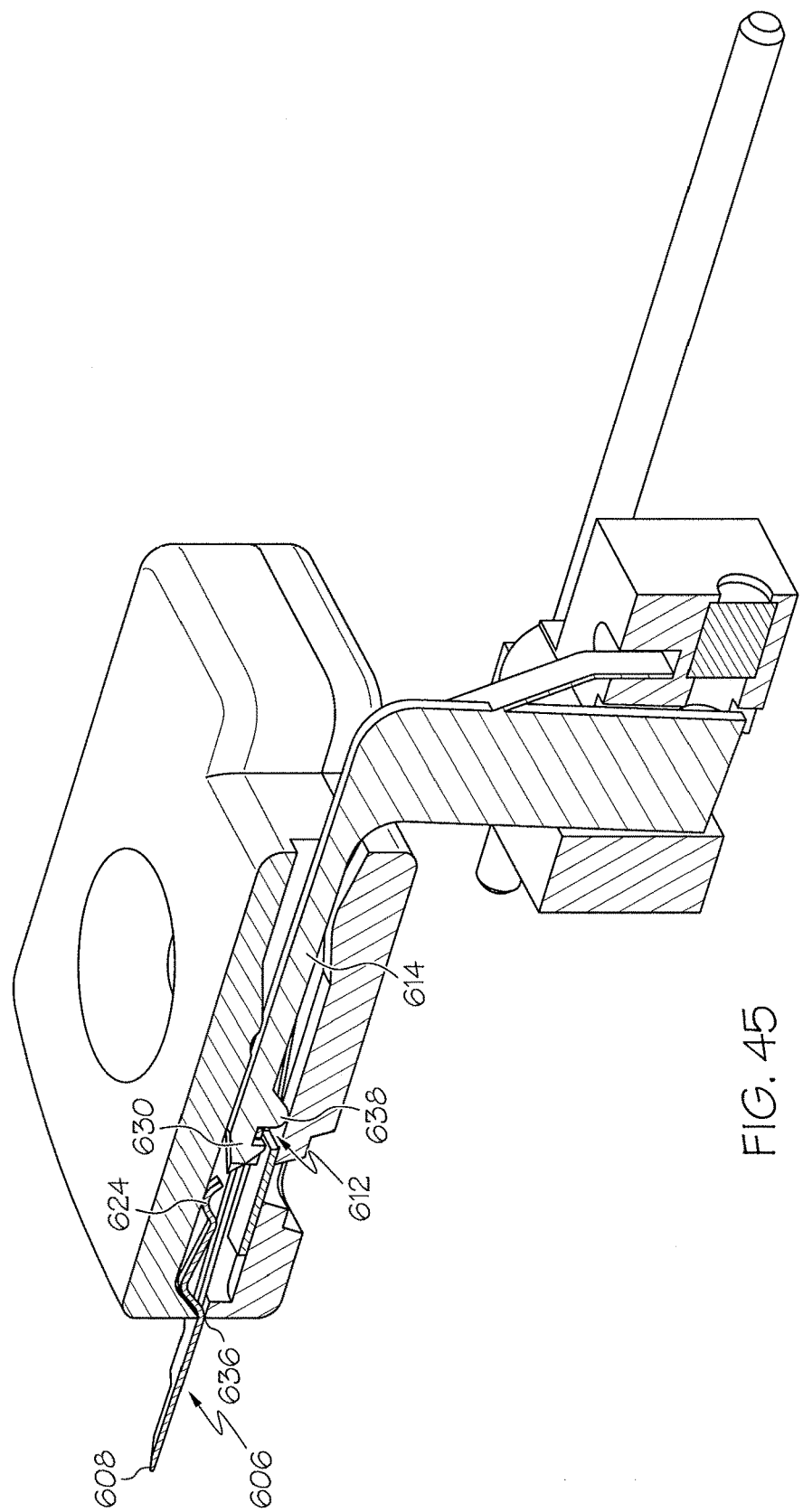
FIG. 45 illustrates the lancet housing assembly of FIG. 41 in operation.

Referring to FIG. 42, during a priming and firing sequence, the drive member 614 enters the lancet compartment 605 and a guide projection 638 engages an incline ramp surface 640, which forces the hook portion 630 upward as the drive member 614 enters the lancet compartment 605. Referring to FIG. 43, as the drive member 614 continues to move toward the opening 636, the guide projection 638 engages a decline ramp surface 642 and the hook portion 630 travels downward and engages the engagement structure 612 of the lancet structure 606. Referring to FIG. 44, the hook portion 630 continues to travel down the decline ramp surface 642 thereby fully engaging the engagement structure 612 and extending the skin penetrating end 608 of the lancet structure 606 through the opening 636. As can be seen by FIGS. 43 and 44, the hump-shaped portion 624 is forced out of the notch 626 by deflecting the spring finger 616 upon application of a sufficient force by the drive member 614. The amount of force needed to release the hump-shaped portion 624 from the notch 626 can be selected based on the spring force and the shapes of the notch 626 and hump-shaped portion 624. In some embodiments, the hump-shaped portion 624 continues to contact an upper wall surface 644 thereby biasing the lancet structure 606 in a downward direction as the skin penetrating end 608 is extended. FIG. 45 illustrates the lancet structure 606 fully extended.

Figure 46:
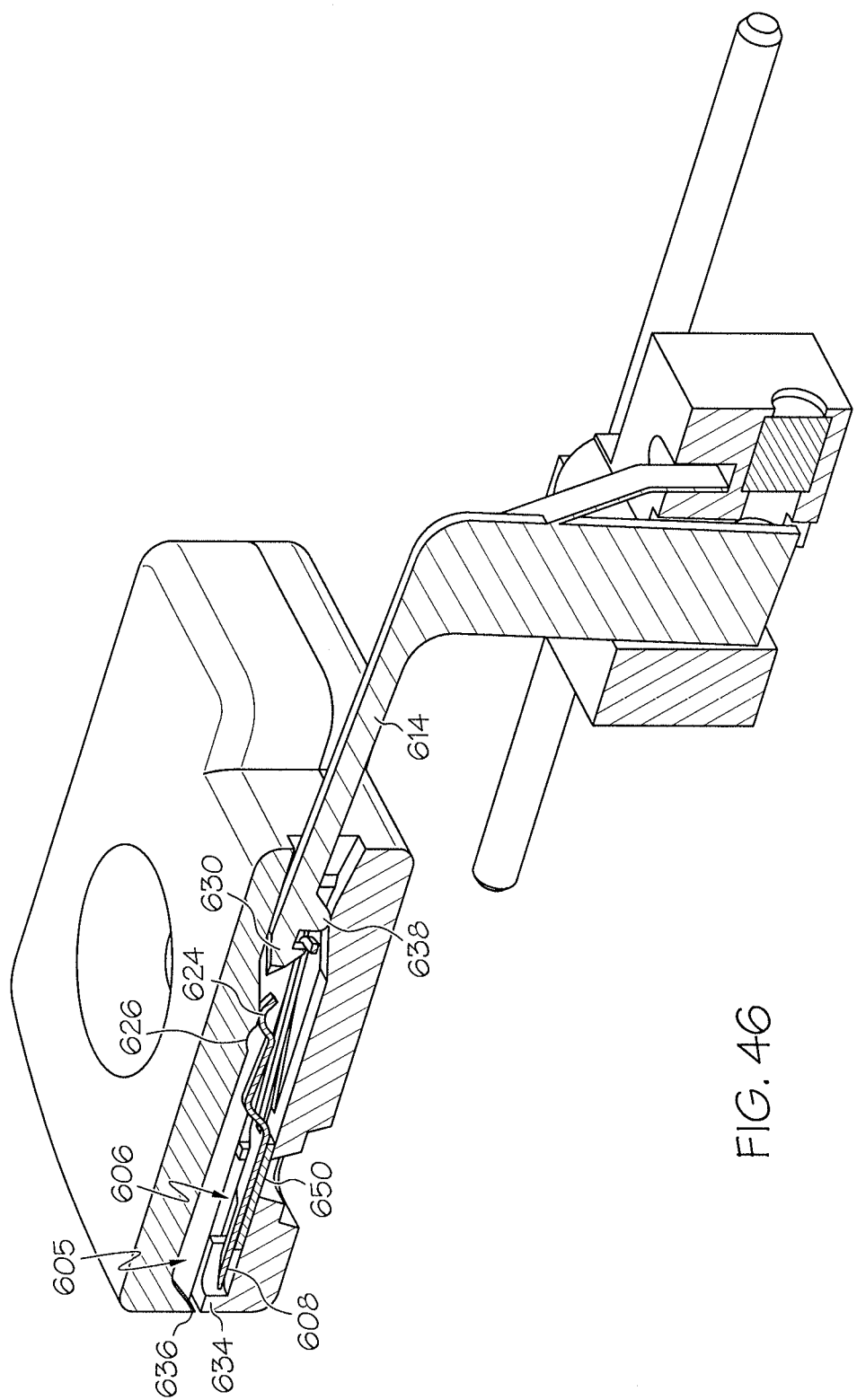
FIG. 46 illustrates the lancet housing assembly of FIG. 41 in operation.
Figure 47:
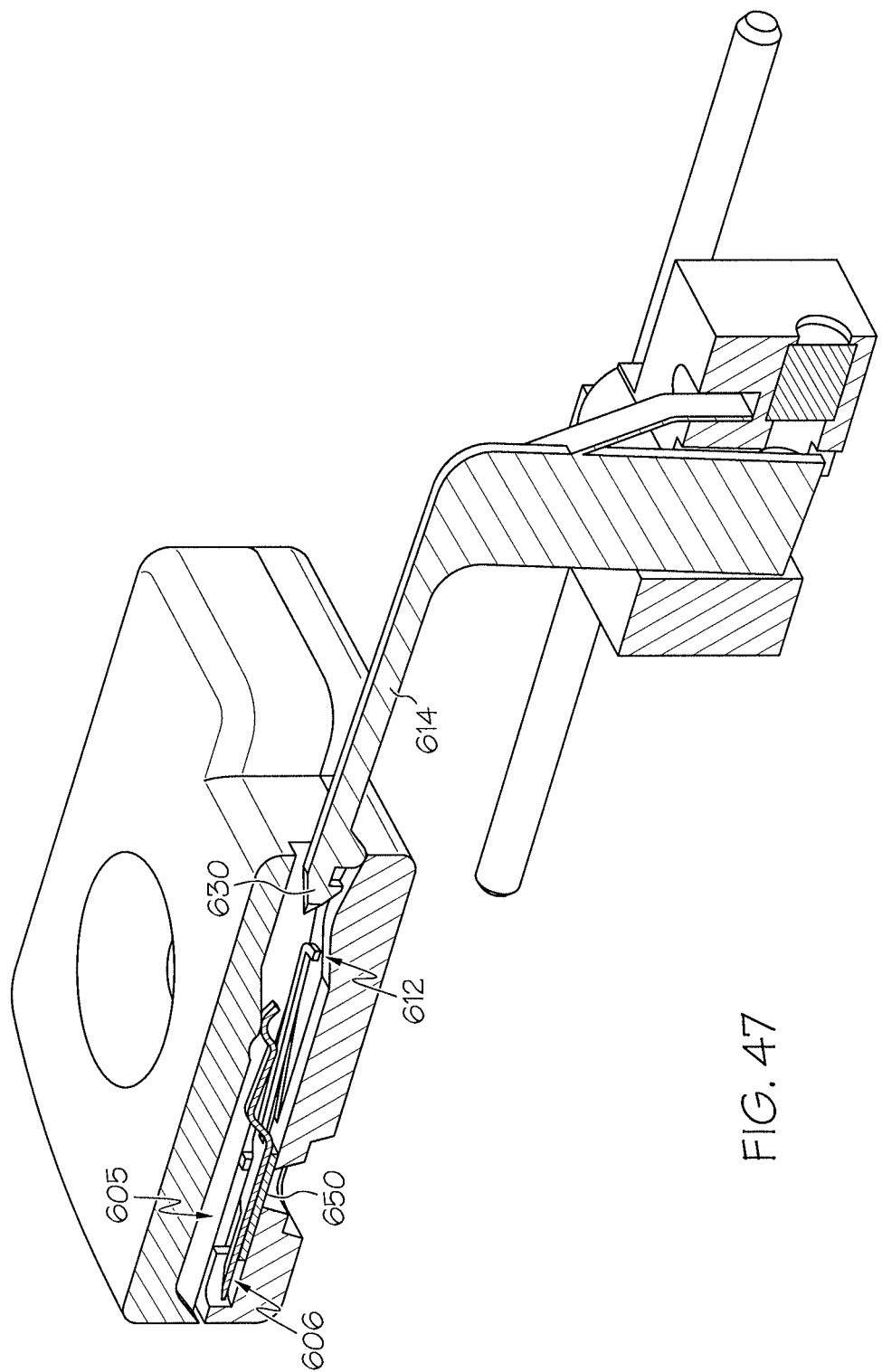
FIG. 47 illustrates the lancet housing assembly of FIG. 41 in operation.
Figure 48:
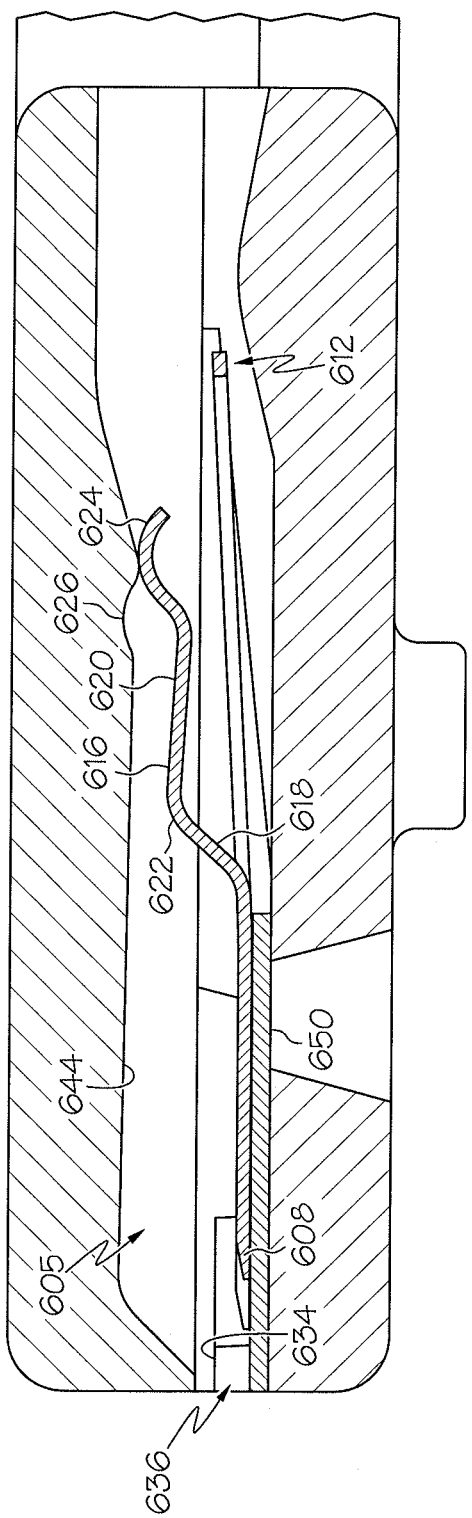
FIG. 48 illustrates the lancet housing assembly of FIG. 41 in operation.

Referring to FIG. 46, during retraction, the skin penetrating end 608 of the lancet structure 606 is pulled back into the lancet compartment 605. The pulling force applied by the drive member 614 is sufficient to pull the hump-shaped portion 624 past the notch 626 to allow the skin penetrating end 608 to clear the support surface 634 at the opening 636 and fall downward toward a reagent material 650 to transfer an amount of bodily fluid to the reagent material. Unhooking of the engagement structure 612 occurs as the lancet structure falls toward the reagent material 650 and the guide projection 638 moves up the ramp surface 642. FIGS. 47 and 48 illustrate the lancet structure 606 in its final, released state with the lancet structure 606 in contact with the reagent material 650 and the skin penetrating end 608 offset from the opening 636.

Figure 49:
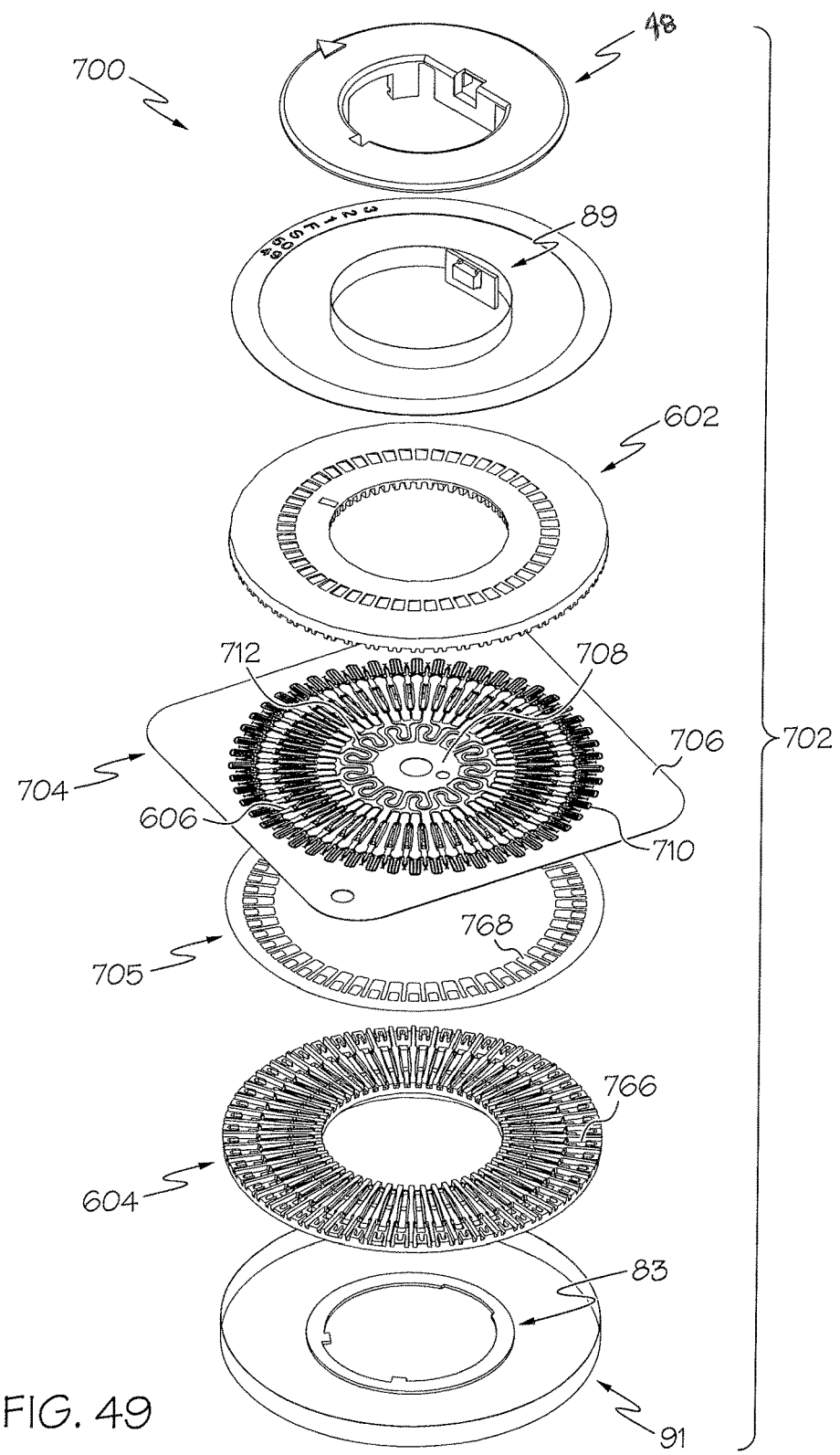
FIG. 49 illustrates an embodiment of a lancet housing pre-assembly.

Referring to FIG. 49, methods and pre-assembled components 702 for use in assembling a lancet housing pre-assembly 700 including the lancet structures 606 are illustrated. The pre-assembled components 702 include the center hub 48, the upper disk member 602 and the lower disk member 604 that together form the lancet compartments 605, foil rings 89 and 91 and the snap ring 83 that is used in connecting the upper disk member 602 and the lower disk member 604 using the center hub 48 in a manner similar to that described above at FIGS. 4-7.

Figure 50:
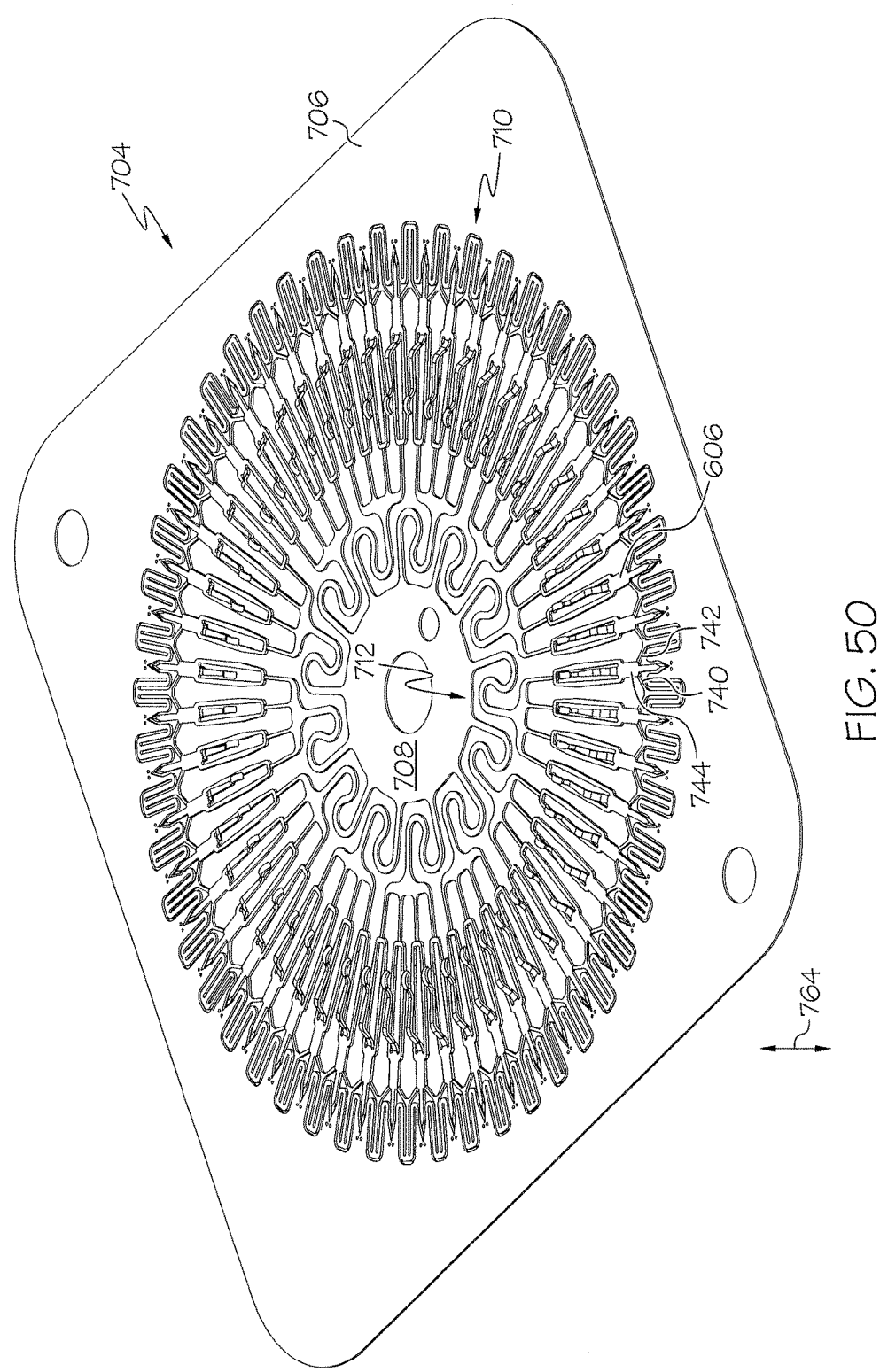
FIG. 50 illustrates an embodiment of a lancet sheet for providing lancet structures.

Located between the upper disk member 602 and the lower disk member 604 are a lancet sheet 704 and a reagent component sheet 705. Referring to FIG. 50, the lancet sheet 704 includes an outer ledge 706, an inner ledge 708 and an array of interconnected lancet structures 606 that are connected to both the outer ledge 706 and the inner ledge 708. The lancet structures 606 are formed of material (e.g., stainless steel) that forms the rest of the lancet sheet 704 including the outer ledge 706 and the inner ledge 708. For example, any suitable etching or laser cutting process may be used to form the lancet structures 606 in the lancet sheet 704.

Figure 51:
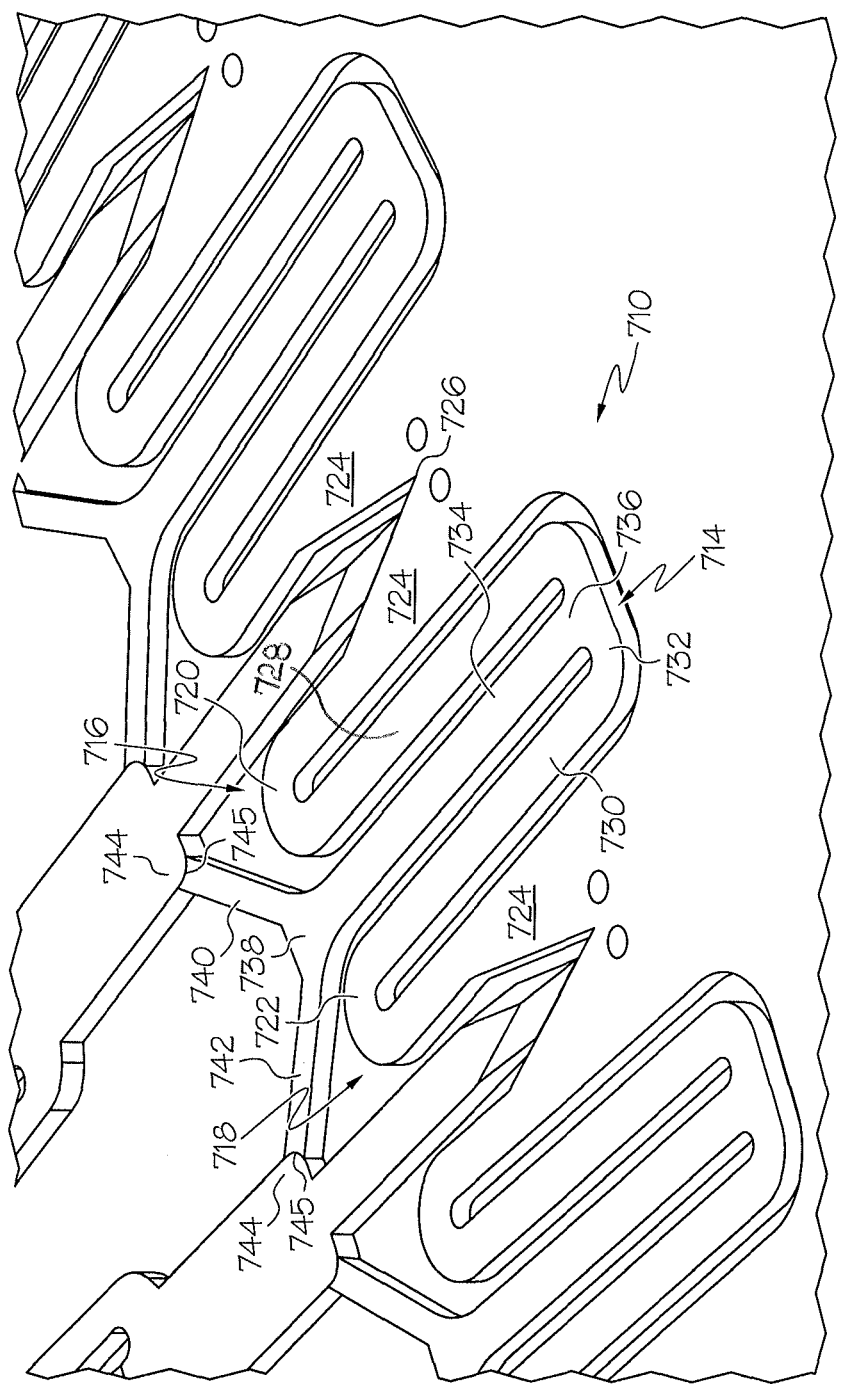
FIG. 51 illustrates a detail view of the lancet sheet of FIG. 50.

The lancet structures 606 are connected to the outer ledge 706 by an array of outer spring components 710 and to the inner ledge 708 by an array of inner spring components 712. Generally, the outer and inner spring components 710 and 712 facilitate flexing of their corresponding outer ledge 706 and inner ledge 708 and the release of the lancet structures 606 from the lancet sheet 700 during assembly. Referring to FIG. 51 the outer spring components 710 are illustrated in detail and each includes an attachment spring arm 714 and outer ledge attachment arms 716 and 718. The attachment spring arm 714 is U-shaped and is connected to each of the outer ledge attachment arms 716 and 718 at bends 720 and 722. In some embodiments, the outer ledge attachment arms 716 and 718 each have a portion 724 of increased width that attaches to the outer ledge 706. The portions 724 of increased width can provide the outer ledge attachment arms 716 and 718 with greater rigidity compared to the attachment spring arm 714. As can be seen, the lancet structure 606 extends into a notch 726 formed between adjacent portions 724.

The attachment spring arm 714 includes a first radially extending leg 728 (extending substantially parallel to an elongated axis of the lancet structures 606) and a second radially extending leg 730 with a transverse leg 732 extending between the legs 728 and 730. A lancet attachment arm 734 is connected at one end 736 to the transverse leg 732 and at an opposite end 738 to adjacent lancet structures 606. The lancet attachment arm 734 acts as a moment arm that can increase the torque applied at the connection between the lancet attachment arm 734 and the lancet structure 606. The lancet attachment arm 734 includes breakable fingers 740 and 742 that attach the lancet attachment arm 734 to the lancet structures 606 at shoulders 744. In some embodiments, the breakable fingers 740 and 742 may include a line of weakness 745 that is formed into the breakable fingers 740 and 742. For example, the line of weakness 745 may be a partially etched or laser scored region of the breakable fingers 740 and 742 where the breakable fingers 740 and 742 meet the lancet structures 606. As will be described in greater detail below, the outer spring components 710 allow the outer ledge 706 to move relative to the lancet structures 606 to break the outer ledge 706 from the lancet structures 606 at the connection between the breakable fingers 740 and 742 and the lancet structures 606.

Figure 52:
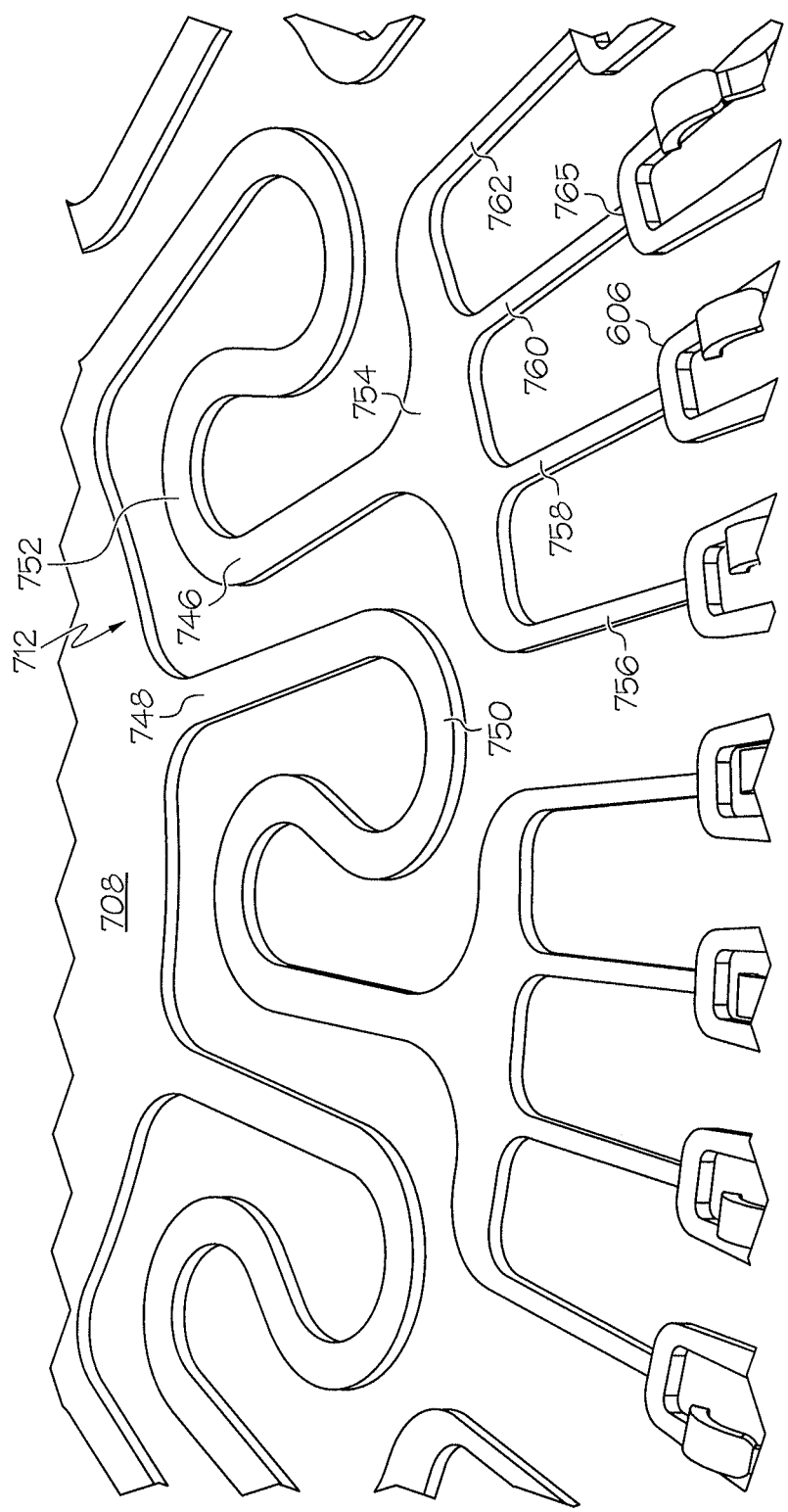
FIG. 52 illustrates another detail view of the lancet sheet of FIG. 50.

Referring to FIG. 52, the inner spring components 712 are illustrated in detail and each includes an attachment spring arm 746. The attachment spring arm 746 is wave-shaped and is connected to the inner ledge 708 at end 748 through bends 750 and 752. At an opposite end 754, the attachment spring arm 746 is attached to multiple lancet structures 606 by breakable fingers 756, 758, 760 and 762. In some embodiments, two or more (such as four) breakable fingers 756, 758, 760 and 762 may be connected to a single attachment spring arm 746, with each breakable finger 756, 758, 760 and 762 being connected to a respective lancet structure 606. In some embodiments, the breakable fingers 756, 758, 760 and 762 may include a line of weakness 765 that is formed into the breakable fingers 756, 758, 760 and 762. For example, the line of weakness 765 may be a partially etched or laser scored region of the breakable fingers 756, 758, 760 and 762 where the breakable fingers 756, 758, 760 and 762 meet the lancet structures 606. As will be described in greater detail below, the inner spring components 712 allow the inner ledge 708 to move relative to the lancet structures 606 to break the inner ledge 708 from the lancet structures 606 at the connection between the breakable fingers 756, 758, 760 and 762 and the lancet structures 606.

Figure 53:
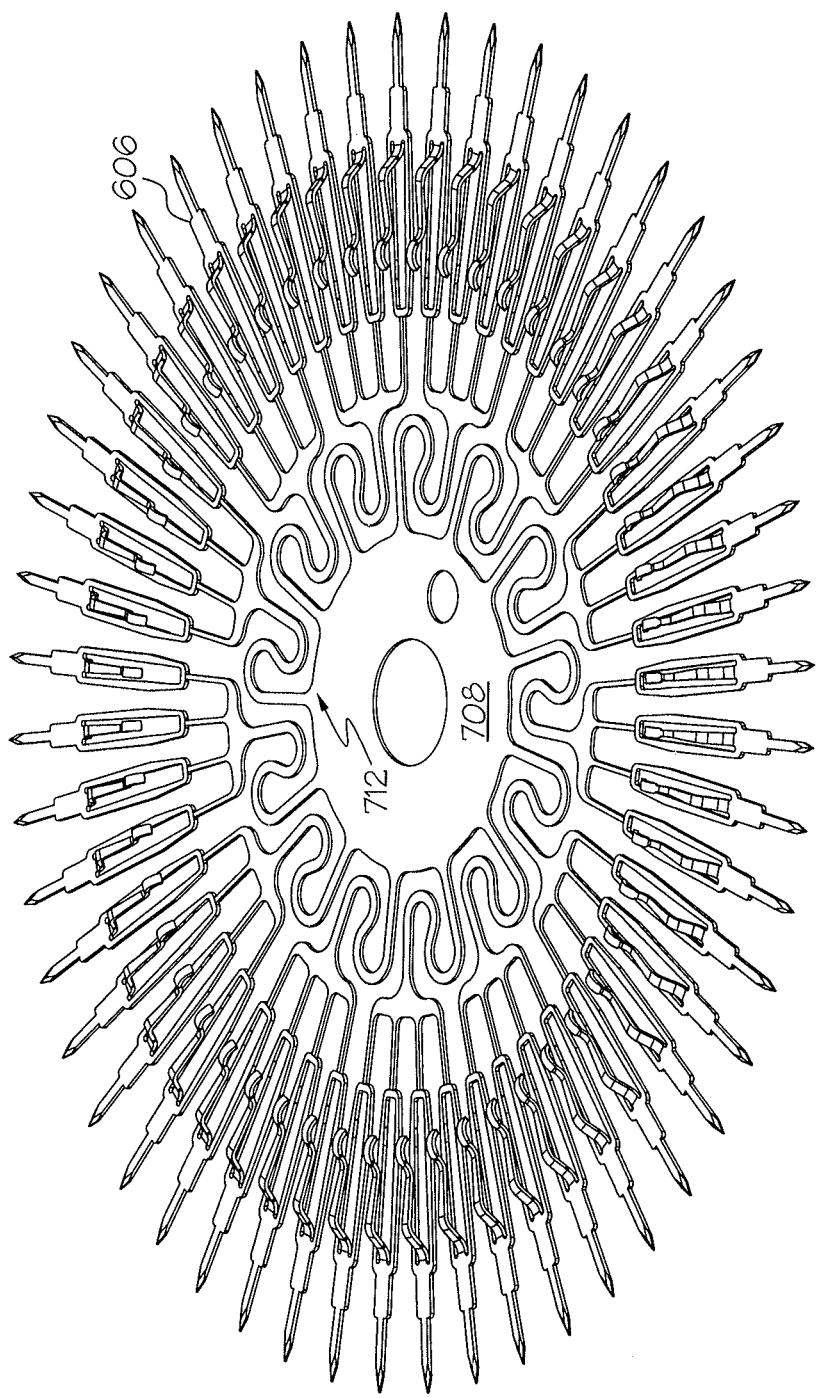
FIG. 53 illustrates the lancet sheet of FIG. 50 with an outer ledge removed.
Figure 54:
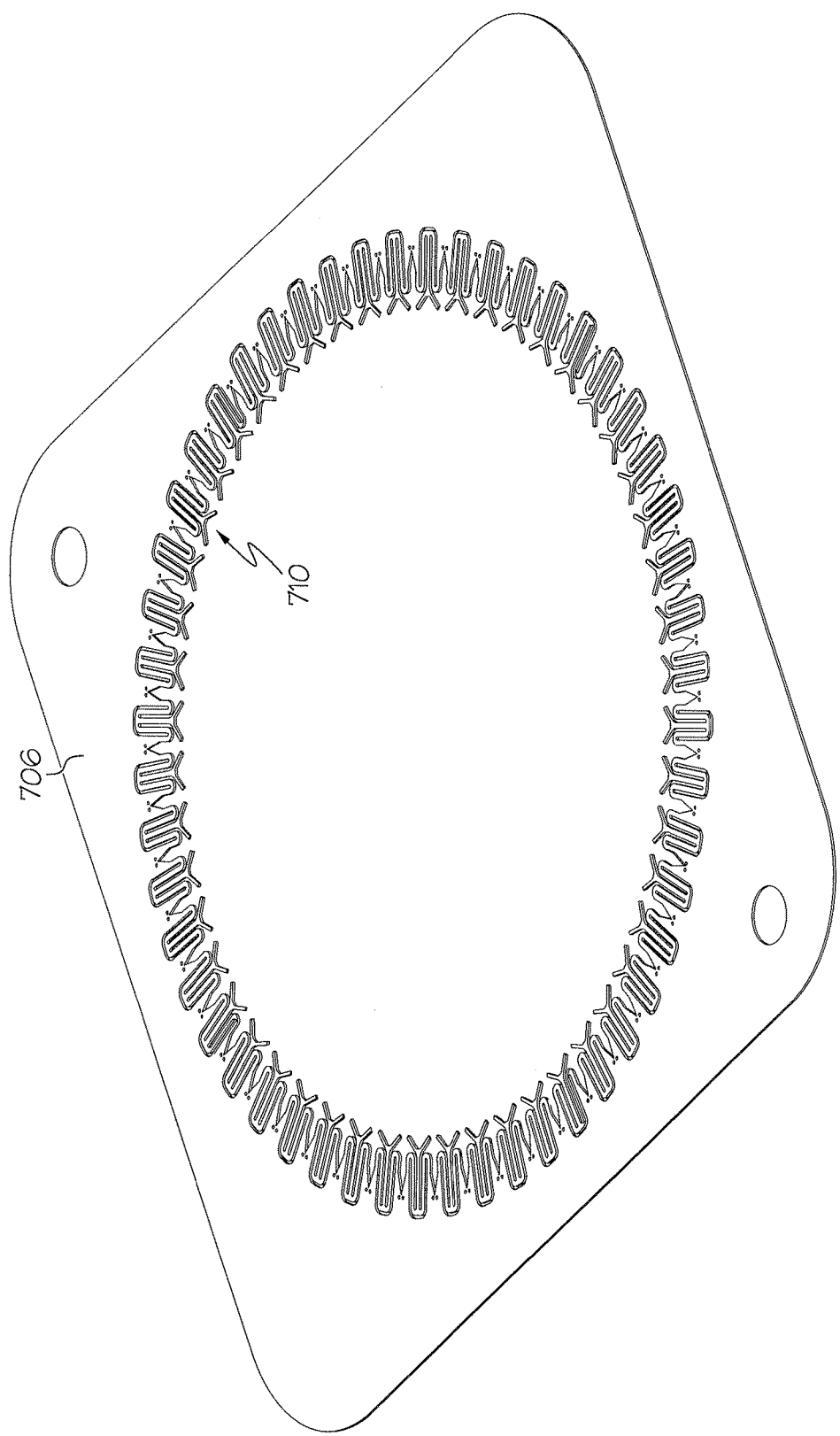
FIG. 54 illustrates the removed outer ledge of FIG. 50.

Referring back to FIG. 50, to remove the outer ledge 706, the outer ledge 706 may be flexed out of the plane of the lancet sheet 700 in the direction of arrows 764 while the inner ledge 708 and lancet structures 606 are held in a fixed position, e.g., by a clamped fixture. Thus, in this example, the outer ledge 706 flexes relative to the inner ledge 708. Rapid flexing of the outer ledge 706 relative to the inner ledge 708 and the lancet structures 606 causes the breakable fingers 740 and 742 to break away from the shoulders 744 of the lancet structures 606. FIG. 53 illustrates the lancet structures 606 removed from the outer ledge 706 and still interconnected with the inner ledge 708. FIG. 54 illustrates the outer ledge 706 removed from the lancet structures 606 with the spring components 710 remaining connected thereto.

Referring to FIG. 49, once the outer ledge 706 of the lancet sheet 700 is removed, the lancet structures 606 of FIG. 50 may be positioned within the lancet compartment halves 766 of the lower disk member 604. In some embodiments, the lancet structures 606 may be placed within the lancet compartment halves 766 after the reagent components 768 from the reagent component sheet 705 in a similar flexing fashion. Once the lancet structures 606 are located in the lancet compartment halves 766, the lower disk member 604 may be assembled to the upper disk member 602, for example by welding the upper and lower disk members 602 and 604 together.

Figure 55:
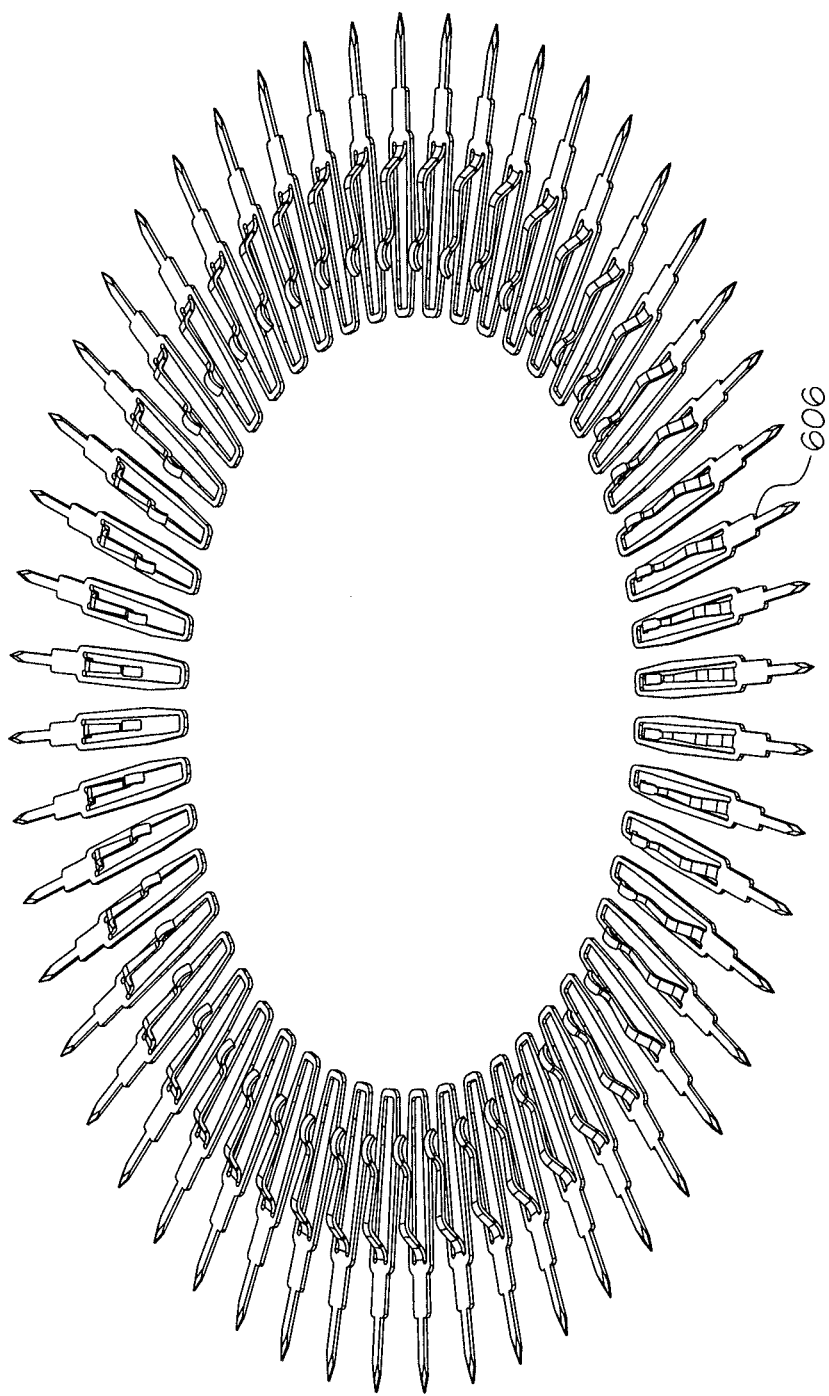
FIG. 55 illustrates lancet structures released from the lancet sheet of FIG. 50.
Figure 56:
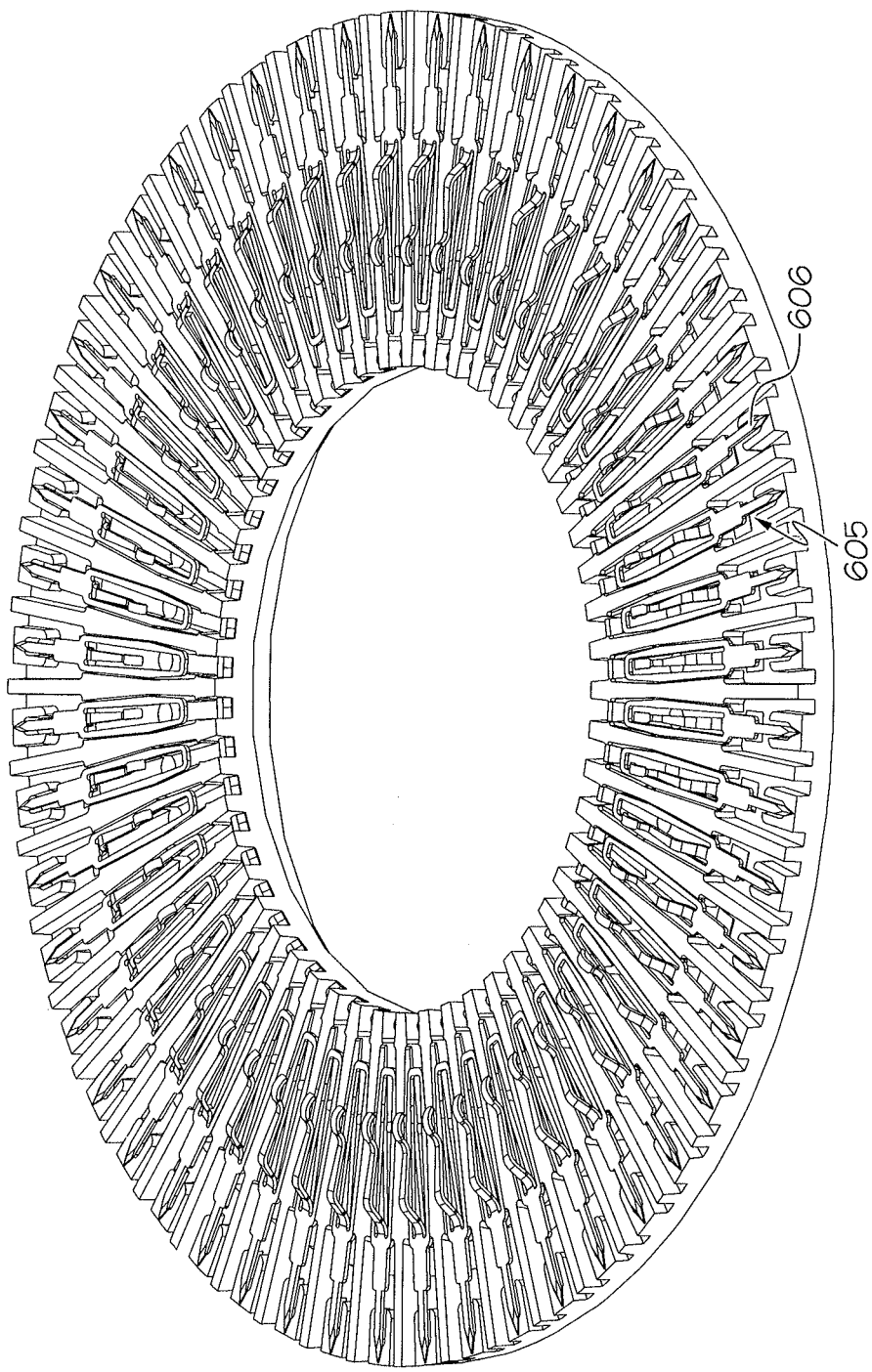
FIG. 56 illustrates the released lancet structures of FIG. 55 within lancet compartments.

Referring again to FIG. 50, to remove the inner ledge 708, the inner ledge 708 may be flexed out of the plane of the lancet sheet 700 in the direction of arrows 764 while the lancet structures 606 are held in a fixed position within the lancet compartments 605. In some embodiments, the lancet structures 606 may be held stationary or fixed using any suitable clamping structure, such as pins. Thus, in this example, the inner ledge 708 flexes relative to the lancet structures 606. Rapid flexing of the inner ledge 708 relative to the lancet structures 606 causes the breakable fingers 756, 758, 760 and 762 to break away from the lancet structures 606. FIG. 55 illustrates the lancet structures 606 in isolation, removed from the outer ledge 706 and the inner ledge 708. FIG. 56 illustrates the removed lancet structures 606 within the lancet compartments 605 with the upper disk member 602 removed.

The above-described lancet structure placement process allows each lancet structure 606 of the lancet sheet 700 to be simultaneously placed within individual lancet compartments 605, for example, without handling the lancet structures 606 individually. The lancet structures 606 can be removed from the outer ledge 706 and the inner ledge 708 simultaneously by flexing the outer ledge 706 and the inner ledge 708 relative to the lancet structures 606.

The above-described medical diagnostic devices include a number of features that allow for improved comfort and ease of use for a patient. In general, the medical diagnostic devices may include a lancet housing assembly in the form of a cartridge or disk that is used to house multiple lancet structures for use in the medical diagnostic devices, a lancet actuator assembly for extending and retracting the lancet structures and a speed control mechanism that engages the lancet actuator assembly for adjusting the speed at which the lancet structure is extended and/or retracted by the lancet actuator assembly. A depth adjustment mechanism may also be provided that allows for adjustment of an initial position of the lancet structure prior to its use, which can adjust the penetration depth of the lancet structure during use.

The following are numbered embodiments of the present invention:

1. A method of assembling a lancet housing assembly comprising multiple lancets for use in a portable handheld medical diagnostic device for sampling bodily fluids from a skin site of a patient, the method comprising:
   forming a plurality of the lancet structures in a lancet sheet, the lancet sheet having a removable ledge for releasing the lancet structures; and
   flexing the removable ledge of the lancet sheet for releasing the lancet structures from the removable ledge.

2. The method of embodiment 1 further comprising forming a plurality of spring components in the lancet sheet that connect the lancet structures to the removable ledge.

3. The method of embodiment 2, wherein the spring components are formed to include an attachment spring arm connected to the lancet structure and an outer ledge attachment arm connecting the attachment spring arm to the removable ledge.

4. The method of embodiment 2, wherein the spring components are formed to include a lancet attachment arm connecting the attachment spring arm to the lancet structure.

5. The method of embodiment 4, wherein the spring components are formed such that the lancet attachment arm includes a breakable finger connected to the lancet structure such that the step of flexing the removable ledge breaks the breakable finger from the lancet structure.

6. The method of embodiment 5, wherein the breakable finger is a first breakable finger and the lancet structure is a first lancet structure, the lancet attachment arm formed to include a second breakable finger connected to a second, adjacent lancet structure such that the step of flexing the removable ledge breaks the first breakable finger from the first lancet structure and the second breakable finger from the second lancet structure.

7. The method of embodiment 1, wherein the removable ledge is an outer removable ledge, the lancet sheet further comprising an inner removable ledge for releasing the lancet structures.

8. The method of embodiment 7 further comprising flexing the inner removable ledge of the lancet sheet for releasing the lancet structures from the inner removable ledge.

9. The method of embodiment 8, wherein the step of flexing the outer removable ledge occurs prior to the step of flexing the inner removable ledge such that the lancet structures remain connected to the inner removable ledge after the outer removable ledge is removed from the lancet structures.

10. The method of embodiment 9 further comprising locating the lancet structures within a plurality of lancet compartments of the lancet housing assembly prior to the step of flexing the inner removable ledge for releasing the lancet structures from the inner removable ledge.

11. A lancet sheet providing multiple lancets for a lancet housing assembly for use in a portable handheld medical diagnostic device for sampling bodily fluids from a skin site of a patient, the lancet sheet comprising:
- a removable ledge formed of material forming the lancet sheet;
- a plurality of lancet structures formed of material forming the lancet sheet, the plurality of lancet structures comprising a skin penetrating end and a blood transport portion adjacent the skin penetrating end, wherein the skin penetrating end is shaped and sized to penetrate the patient's skin at the skin site to provide an amount of blood; and
- a plurality of spring components formed of material that forms the lancet sheet that releasably connect the plurality of lancet structures to the removable ledge.

12. The lancet sheet of embodiment 11, wherein the plurality of spring components comprise:
- an attachment spring arm connected to a lancet structure of the plurality of lancet structures; and
- a ledge attachment arm that connects the attachment spring arm to the removable ledge.

13. The lancet sheet of embodiment 12, wherein the attachment spring arm is connected to the lancet structure by a lancet attachment arm, wherein the lancet attachment arm is connected at a first end of the attachment spring arm, the attachment spring arm being connected at a second opposite end to the ledge attachment arm.

14. The lancet structure of embodiment 13, wherein the lancet attachment arm is connected to the lancet structure by a breakable finger.

15. The lancet structure of embodiment 14, wherein the breakable finger comprises a line of weakness.

16. A lancet housing pre-assembly for forming a lancet housing assembly comprising multiple lancet structures for use in a portable handheld medical diagnostic device for sampling bodily fluids from a skin site of a patient, the lancet housing pre-assembly comprising:
- an upper disk member;
- a lower disk member that connects to the upper disk member for forming a plurality of lancet compartments therebetween for housing a plurality of lancet structures;
- a lancet sheet providing the plurality of lancets for the lancet housing assembly, the lancet sheet comprising:
  - a removable ledge formed of material forming the lancet sheet;
  - a plurality of lancet structures formed of material forming the lancet sheet, the plurality of lancet structures comprising a skin penetrating end and a blood transport portion adjacent the skin penetrating end, wherein the skin penetrating end is shaped and sized to penetrate the patient's skin at the skin site to provide an amount of blood; and
  - a plurality of spring components formed of material that forms the lancet sheet that releasably connects the plurality of lancet structures to the removable ledge.

17. The lancet housing pre-assembly of embodiment 16, wherein the plurality of spring components comprise:
- an attachment spring arm connected to a lancet structure of the plurality of lancet structures; and
- a ledge attachment arm that connects the attachment spring arm to the removable ledge.

18. The lancet housing pre-assembly of embodiment 17, wherein the attachment spring arm is connected to the lancet structure by a lancet attachment arm, wherein the lancet attachment arm is connected at a first end of the attachment spring arm, the attachment spring arm being connected at a second opposite end to the ledge attachment arm.

19. The lancet housing pre-assembly of embodiment 18, wherein the lancet attachment arm is connected to the lancet structure by a breakable finger.

20. The lancet housing pre-assembly of embodiment 19, wherein the breakable finger comprises a line of weakness.

The above description and drawings are only to be considered illustrative of exemplary embodiments, which achieve the features and advantages of the present invention. Modification and substitutions to specific process steps, system, and setup can be made without departing from the spirit and scope of the present invention. Accordingly, the invention is not to be considered as being limited by the foregoing description and drawings, but is only limited by the scope of the appended claims.

The invention claimed is:

1. A lancet sheet providing multiple lancets for a lancet housing assembly for use in a portable handheld medical diagnostic device for sampling bodily fluids from a skin site of a patient, the lancet sheet comprising:
- a first removable ledge and a second removable ledge, each formed of material forming the lancet sheet;
- a plurality of lancet structures formed of material forming the lancet sheet, the plurality of lancet structures comprising a skin penetrating end and a blood transport portion adjacent the skin penetrating end, wherein the skin penetrating end is shaped and sized to penetrate the patient's skin at the skin site to provide an amount of blood; and
- a plurality of spring components formed of material that forms the lancet sheet that releasably connect the plurality of lancet structures to the first and the second removable ledges, wherein the first and the second removeable ledges are connected to the plurality of lancet structures via the plurality of spring components so as to be able to be flexed relative to a plane of the lancet sheet and configured to be broken from the plurality of lancet structures when the first and the second removeable ledges are flexed relative to the plurality of lancet structures.

2. The lancet sheet of claim 1, wherein the plurality of spring components comprise:
- an attachment spring arm connected to a lancet structure of one of the plurality of lancet structures; and
- a ledge attachment arm that connects the attachment spring arm to one of the first or the second removable ledges.

3. The lancet sheet of claim 2, wherein the attachment spring arm is connected to the lancet structure by a lancet attachment arm, wherein the lancet attachment arm is connected at a first end of the attachment spring arm, the attachment spring arm being connected at a second opposite end to the ledge attachment arm.

4. The lancet sheet of claim 3, wherein the lancet attachment arm is connected to the lancet structure by a breakable finger.

5. The lancet sheet of claim 4, wherein the breakable finger comprises a line of weakness.

6. A lancet housing pre-assembly for forming a lancet housing assembly comprising multiple lancet structures for use in a portable handheld medical diagnostic device for sampling bodily fluids from a skin site of a patient, the lancet housing pre-assembly comprising:
   an upper disk member;
   a lower disk member that connects to the upper disk member for forming a plurality of lancet compartments therebetween for housing a plurality of lancet structures; and
   the lancet sheet of claim 1.

7. The lancet housing pre-assembly of claim 6, wherein the plurality of spring components comprise:
   an attachment spring arm connected to a lancet structure of one of the plurality of lancet structures; and
   a ledge attachment arm that connects the attachment spring arm to one of the first or the second removable ledges.

8. The lancet housing pre-assembly of claim 7, wherein the attachment spring arm is connected to the lancet structure by a lancet attachment arm, wherein the lancet attachment arm is connected at a first end of the attachment spring arm, the attachment spring arm being connected at a second opposite end to the ledge attachment arm.

9. The lancet housing pre-assembly of claim 8, wherein the lancet attachment arm is connected to the lancet structure by a breakable finger.

10. The lancet housing pre-assembly of claim 9, wherein the breakable finger comprises a line of weakness.

* * * * *